US008754287B2

(12) United States Patent
MacDonald et al.

(10) Patent No.: US 8,754,287 B2
(45) Date of Patent: Jun. 17, 2014

(54) MICE THAT MAKE HEAVY CHAIN ANTIBODIES

(75) Inventors: Lynn MacDonald, White Plains, NY (US); Sean Stevens, San Francisco, CA (US); Andrew J. Murphy, Croton-on-Hudson, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 204 days.

(21) Appl. No.: 12/965,050

(22) Filed: Dec. 10, 2010

(65) Prior Publication Data

US 2011/0145937 A1     Jun. 16, 2011

Related U.S. Application Data

(60) Provisional application No. 61/285,250, filed on Dec. 10, 2009.

(51) Int. Cl.
*A01K 67/027* (2006.01)
*A01K 67/00* (2006.01)
*C12N 15/85* (2006.01)

(52) U.S. Cl.
CPC ........ *A01K 67/0275* (2013.01); *C12N 15/8509* (2013.01); *A01K 2267/01* (2013.01); *A01K 2227/105* (2013.01); *A01K 67/0278* (2013.01)
USPC .............................................. 800/18; 800/8

(58) Field of Classification Search
USPC ........................................................ 800/18, 8
See application file for complete search history.

(56) References Cited

U.S. PATENT DOCUMENTS

| | | | |
|---|---|---|---|
| 5,759,808 | A | 6/1998 | Casterman |
| 5,800,988 | A | 9/1998 | Casterman |
| 5,840,526 | A | 11/1998 | Casterman |
| 5,874,541 | A | 2/1999 | Casterman |
| 6,005,079 | A | 12/1999 | Casterman |
| 6,015,695 | A | 1/2000 | Casterman |
| 6,080,910 | A | 6/2000 | Schreiber et al. |
| 6,765,087 | B1 | 7/2004 | Casterman |
| 6,838,254 | B1 | 1/2005 | Hamers |
| 7,241,733 | B2 | 7/2007 | Heavner |
| 7,541,513 | B2 | 6/2009 | Bruggeman |
| 7,722,871 | B2 | 5/2010 | Casterman |
| 7,786,047 | B2 | 8/2010 | Casterman |
| 7,790,367 | B2 | 9/2010 | Casterman |
| 7,794,981 | B2 | 9/2010 | Hamers |
| 2004/0137570 | A1 | 7/2004 | Grosveld |
| 2004/0142432 | A1 | 7/2004 | Grosveld |
| 2009/0042254 | A1 | 2/2009 | Retallack |
| 2009/0271880 | A1 | 10/2009 | Grosveld |
| 2009/0285805 | A1 | 11/2009 | Grosveld |
| 2009/0307787 | A1 | 12/2009 | Grosveld |
| 2010/0122358 | A1 | 5/2010 | Bruggemann |
| 2010/0197897 | A1 | 8/2010 | Grosveld |
| 2010/0216974 | A1 | 8/2010 | Grosveld |
| 2011/0004948 | A1 | 1/2011 | Grosveld |
| 2011/0004949 | A1 | 1/2011 | Grosveld |

FOREIGN PATENT DOCUMENTS

| | | |
|---|---|---|
| WO | 2004/049794 A2 | 6/2004 |
| WO | 2008/122886 A2 | 10/2008 |
| WO | 2009/013620 A2 | 1/2009 |

OTHER PUBLICATIONS

JAX mice Database. Printout from http://jaxmice.jax.org/strain/002288.html, printed Aug. 23, 2013. pp. 1-2.*
Zou, X. et al. Heavy chain-only antibodies are spontaneously produced in light chain-deficient mice. Journal of Experimental Medicine (Dec. 24, 2007) 204(13):3271-3283. Supplemental Material (2 pages): Figure S1 abd Table S1.
Geraldes, P. et al. Ig heavy chain promotes mature B cell survival in the absence of light chain. Journal of Immunology (2007) 179:1659-1666.
International Search Report for PCT/US2010/059845 dated Mar. 17, 2011, 4 Pages.
Written Opinion of the International Searching Authority for PCT/US2010/059845 dated Mar. 17, 2011, 6 Pages.
Ward, S et al. Binding activities of a repertoire of single immunoglobulin variable domains secreted from *Escherichia coli*. Nature (Oct. 12, 1989) 341:544-546.
Kitamura, D. et al. A B cell-deficient mouse by targeted disruption of the membrane exon of the immunoglobulin m chain gene. Nature (Apr. 4, 1991)350:423-426.
Davies, J. et al. Single antibody domains as small recognition units: design and in vitro antigen selection of camelized, human VH domains with improved proteins stability. Protein Engineering (1996) 9(6):531-537.
Riechmann, L. Rearrangement of the Former VL Interface in the Solution Structure of a Camelised, Single Antibody VH Domain. Journal of Molecular Biology (1996) 259:957-969.
Nieba, L. et al. Disrupting the hyrdophobic patches at the antibody variable/constant domain interface: Improved in vivo folding and physical characterization of an engineered scFv fragment. Protein Engineering (1997) 10(4):435-444.
Nguyen, V.K. et al. Loss of splice consensus signal is responsible for the removal of the entire CH1 domain of the functional camel IgG2A heavy-chain antibodies. Molecular Immunology (1999) 36:515-524.

(Continued)

*Primary Examiner* — Marcia S Noble
(74) *Attorney, Agent, or Firm* — Chaote Hall & Stewart LLP; Kevin J. Pobursky; Tor E. Smeland

(57) ABSTRACT

Genetically modified non-human animals and methods and compositions for making and using them are provided, wherein the genetic modification comprises a deletion in an immunoglobulin constant region CH1 gene (optionally a deletion in a hinge region) of an IgG, IgA, IgD, and/or IgE, and wherein the mouse is capable of expressing a functional IgM. Genetically modified mice are described, including mice having a functional IgM gene and modified to have a deletion of a CH1 domain and a hinge region in a heavy chain constant domain that is not an IgM, e.g., in an IgG heavy chain constant domain. Genetically modified mice that make human variable/mouse constant chimeric heavy chain antibodies (antibodies that lack a light chain), fully mouse heavy chain antibodies, or fully human heavy chain antibodies are provided.

14 Claims, 13 Drawing Sheets

(56) References Cited

OTHER PUBLICATIONS

Riechmann, L. et al. Single domain antibodies: comparison of camel VH and camelised human VH domains. Journal of Immunological Methods (1999) 231:25-38.

Harmsen, M. et al. Llama heavy-chain V regions consist of at least four distinct subfamilies revealing novel sequence features. Molecular Immunology (2000) 37:579-590.

Ewert, S. et al. Biophysical Properties of Camelid VHH Domains Compared to Those of Human VH3 Doamins. Biochemistry (2002) 41:3628-3636.

Nguyen, V.K. et al. Heavy-chain only antibodies derived from dromedary are secreted and displayed by mouse B cells. Immunology (2003) 109:93-101.

To, R. et al. Isolation of Monomeric Human VHS by a Phage Selection. Journal of Biological Chemistry (2005) 280 (50):41395-41403.

Zou, X. et al. Expression of a Dromedary Heavy Chain-Only Antibody and B Cell Development in the Mouse. Journal of Immunology (2005) 175:3769-3779.

Bruggemann, M. et al. Heavy-Chain-Only Antibody Expression and B-Cell Development in the Mouse. Critical Reviews in Immunology (2006) 26(5):377-390.

Janssens, R. et al. Generation of heavy-chain-only antibodies in mice. PNAS (Oct. 10, 2006) 103 (41):15130-15135: including 7 additional pages of supporting information (Figures 7, 8, 9 and Supporting Methods).

Masuda, K. et al. The role of interface framework residues in determining antibody VH/VL interaction strength and antigen-binding affinity. The FEBS Journal (2006) 273:2184-2194.

Barthelemy, P.A. et al. Comprehensive Analysis of the Factors Contributing to the Stability and Solubility of Autonomous Human VH Domains. Journal of Biological Chemistry (2008) 283(6):3639-3654.

Zou, X. et al. Removal of the BiP-retention domain in Cm permits surface deposition and developmental progression without L-chain. Molecular Immunology (2008) 45:3573-3579.

Matheson, L.S. et al. Light chain deficient mice produce novel multimeric heavy-chain-only IgA by faulty class switching. International Immunology (2009) 21(8):957-986.

Wang, N. et al. Conserved amino acid networks involved in antibody variable domain interactions. Proteins (2009) 76:99-114.

Hamers-Casterman, C. et al. Naturally occuring antibodies devoid of light chains. Nature (Jun. 3, 1993) 363:446-448.

Azwai, S.M. et al. Immunoglobulins of Camel (*Camelus dromedarius*) Colostrum. Journal of Comparative Pathology (1996) 114:273-282.

Ghahroudi, M.A. et al. Selection of identification of single domain antibody fragments from camel heavy-chain antibodies. FEBS Letters (1997) 414:521-526.

Conrath, K.E. et al. Beta-Lactamase inhibitors Derived from Single-Domain Antibody Fragments Elicited in the Camelidae. Antimicrobial Agents and Chemotherapy (Oct. 2001) 45(10):2807-2812.

Muyldermans, S. Single domain camel antibodies: current status. Reviews in Molecular Biotechnology (2001) 74:277-302.

Muyldermans, S. et al. Recognition of antigens by single-domain antibody fragments: the superfluous luxury of paired domains. Trends in Biochemical Sciences (Apr. 2001) 26(4):230-235.

Wernery, U. Camelid Immunoglobulins and Their Importance for the New-Born—A Review. Journal of Veterinary Medicine (2001) 48:561-568.

Dumoulin, M. et al. Single-domain antibody fragments with high conformational stability. Protein Science (2002) 11:500-515.

Holt, L.J. et al. Domain antibodies: proteins for therapy. Trends in Biotechnology (Nov. 2003) 21(11):484-490.

Muyldermans, S. et al. Camel antibodies and single-domain antibodies. Published online Mar. 19, 2003 at http://ultr.vub.ac.be/ULTR/camel_antibodies.html, 2 Pages.

Omidfar, K. et al. Production of a Novel Camel Single-Domain Antibody Specific for the Type III Mutant EGFR. Tumor Biology (2004) 25:296-305.

Omidfar, K. et al. Production and Characterization of a New Antibody for the Mutant EGF Receptor, EGFRvill, in *Camelus bactrianus*. Tumor Biology (2004) 25:179-187.

De Haard, H.J.W. et al. Llama Antibodies against a Lactococcal Protein Located at the Tip of the Phage Tail Prevent Phage Infection. Journal of Bacteriology (Jul. 2005) 187(13):4531-4541.

Harmsen, M.M. et al. Properties, production, and applications of camelid single-domain antibody fragments. Applied Microbiology and Biotechnlogy (2007) 77:13-22.

Dalton, M. When a Llama is Laid Back, It's Not the Only Beneficiary. Published Online Feb. 17, 2009 at http://www.wsj.com, 3 Pages.

Giersberg, M.M. et al. Covalent dimerization of camelidae anti-humna TNF-alpha single domain antibodies by the constant kappa light chain domain improves neutralizing activity. Biotechnology and Bioengineering (May 2010) 106(1):161-166. (Submitted as preprint publication, pp. 1-20).

Moran, Nuala, "Mouse platforms jostle for slice of humanized antibody market," Nature Biotechnology, vol. 31(4): 267-268, 2013.

* cited by examiner

|    | FR1 | CDR1 | FR2 | CDR2 | |
|----|-----|------|-----|------|---|
| B1 | EVQLQQSGAELVRPGSSVKMSCKTS | GYTFTSYG. | INWVKQRPGQGLEWIGY | IYIGNGYT.. | EYNEKFK |
| B2 | EVQLQQSGrELVKPGASVmISCtAS | GYTFiDYf. | iNWmKrSHGqSLEWIGD | INPNNGGs.. | nYNQKFK |
| B3 | QVQLQQPGAELVKPGASVKLSCKAS | GYTFTSYW. | MQWVKQRPGQGLEWIGE | IDPSDSYT.. | NYNQKFK |
| B5 | EVQLQQSGAEiVKsGASVKLSCTAS | GFNmKDYf. | iHWVKQRTEQGLEWIGR | IDPEDGkT.. | KYAPKFQ |
| D2 | DVQLQESGPGLVKPSQSLSLTCSVT | GYSITSGYY | WNWIRQFPGNKLEWMGY | ISYDGrN... | NYNPSLK |
| D5 | EVQLQQSGAELVRPGASVKLSCTAS | GFNIKDYY. | iHWVKkRPEQGLEWIGR | IDPEDGDT.. | EYAPKFQ |
| D6 | EVQLQQSGTELVKPGASaKLSCTAS | GFNvKDYf. | MHWVKQkTEQGLEWIGR | IVPEDGET.. | KsAPKFQ |
| E2 | EVKLVESGGGLVQSGRSLRLSCATS | GFTFSDFY. | MEWVRQAPGKGLEWIAt | SRNKlNDYTp | EfSASVK |
| E8 | QVQLQQPGAELVKPGASVKLSCKAS | GYTFTSYW. | MHWVKQRPGRGLEWIGR | IDPNSGGT.. | KYNEKlK |
| E10 | EVQLQQSGPELVKPGASVKISCKAS | GYSFTGYY. | MNWVKQSPEKSLEWIGE | INPSTGGT.. | TYNQKFK |
| F6 | EVQLVESGGDLVePGGSLKLSCAAS | GFTFSSYG. | MSWVRQTPDKRLEWVAT | ISSGGSYT.. | YYPDSVK |

|    | CDR3 | | FR4 | CH2 |
|----|------|---|-----|-----|
| B1 | GKATLTSDTSSSTAYMQLSSLTSEDSAIYFr | ARGRrvGPY......YFDY | WGQGTTLTVSS | VPEVSSVFI |
| B2 | GKATLTVDKSSSTAYMdLRSLTSEDSAVYYC | AKLGRD......WYFDV | WGtGTTVTVSS | VPEVSSVFI |
| B3 | GKATLTVDTSSSTAYMQLSSLTpEDSAVYYC | ARCRY......YFDY | WGQGTTLTVSS | VPEVSSVFI |
| B5 | GKATITADTSSNTAYLhLSSLTSEDTAVYYC | ARGGLGREE..YYAvDY | WGQGTSVTVSS | VPEVSSVFI |
| D2 | NRISITRDTSKNQFFLKLNSVTTEDTATYYC | AIHTVVGD....YvMDY | WGQGTSVTVSS | VPEVSSVFI |
| D5 | GKATMTADTSSNTAYLQLSSLTSEDiAVYYC | TTSRpF......YFDY | WGQGTTLTVSS | VPEVSSVFI |
| D6 | drtTIrtDTSSNTShLQLnSLTSEDTAVYYC | ARPNPP.........Y | WGQGTLVTVSv | VPEVSSVFI |
| E2 | GRFIVSRDTSQnILYLQMNALRpEDTAIYYC | ARAcSdYDR..YYAMDY | WGQGTSVTVSS | VPEVSSVFI |
| E8 | nKATLTVDKPSSSTAYMQLSSLTSEDSAVYYC | AREEINYYGSTYgAMDY | WGQGTSVTVSS | VPEVSSVFI |
| E10 | AKATLTVDKSSSTAYMQLKSLTSEDSAVYYC | AGG.........YWYFDV | WGtGTTVTVSS | VPEVSSVFI |
| F6 | GRFTISRDNAKNTLYLQMSSLKSEDTAMYYC | ARHDYYGSSYG.WYFDV | WGtGTTVTVSS | VPEVSSVFI |

Figure 12

| | FR1 | CDR1 | FR2 | CDR2 | |
|---|---|---|---|---|---|
| A8 | QVQLVQSGAEVKKPGASVKVSCKAS | GYTFTSYD. | INWVRQATGQGLEWMGW | MNPNSGkT.. | GYAQKFQ |
| C2 | QVQLVQSGAEmKKPGASVKVSCKAS | GYTFTSYG. | ISWVRQAPGQGLEWMGW | ISAYNGNT.. | yYAQnLQ |
| D9 | QVQLVQSGAEmKKPGASVKVSCKAS | GYTFTSYG. | ISWVRQAPGQGLEWMGW | ISAYNGNT.. | yYAQnLQ |
| C4 | QVQLVQSGAEVKKPGASVKVSCKAS | GYTFTSYG. | ISWVRQAPGQGLEWMGW | ISAYNGNT.. | NYAQKLQ |
| H8 | QVQLlQSGAEVKKPGASVKVSyKAS | dYTFTSYG. | ISWVRQAPGQGLEWMGW | ISAYNGNT.. | NYAQnLQ |
| A5 | QVQLVQSGAEVKKPGSSVKVSCKAS | GGTFSSYA. | ISWVRQAPGQGLEWMGG | IIPIFGTA.. | NYAQKFQ |
| A2 | QVQLVQSGAEVKKPGSSVKVSCKAS | GGTFSSYA. | ISWVRQAPGQGLEWMGG | IIPIFGTA.. | NYAQKFQ |

| | FR3 | CDR3 | FR4 | HINGE |
|---|---|---|---|---|
| A8 | GRVaMTRkTSISTAYMELSSLRSEDTAVYYC | AReDYSNYgd..........FDY | WGQGTLVTVSS | VPRDCGC |
| C2 | GRVTMTTDTSTSaAfMdLRSDDTAVYYC | ARdgYStSsl...........DY | WGQGTLVTVSS | VPRDCGC |
| D9 | GRVTMTTDTSTSaAfMdLRSDDTAVYYC | ARdgYStSsl...........DY | WGQGTLVTVSS | VPRDCGC |
| C4 | GRVTMTTDTSTSTAYMELRSDDTAVYYC | ARddMITFGGVIanYYYYGMDV | WGQGTTVTVtS | VPRDCGC |
| H8 | GRVTMTTDTSTSTAYMELRSDDsAVYYC | AReeLEl............FDY | WGQGTLVTVSS | VPRDCGC |
| A5 | GRVTITTDESTSTAYMELSSLRSEDTAVYYC | ARdgYStSsl...........DY | WGQGTLVTVSS | VPRDCGC |
| A2 | GRVTITTDESTSTAYMELSSLRSEDTAVYYC | AvIAVAGT......YYYYGMDV | WGQGTTVTVSl | VPRDCGC |

SEQUENCE LISTING

```
<160> NUMBER OF SEQ ID NOS: 64

<210> SEQ ID NO 1
<211> LENGTH: 21
<212> TYPE: DNA
<213> ORGANISM: Artificial Sequence
<220> FEATURE:
<223> OTHER INFORMATION: synthetic

<400> SEQUENCE: 1
tcaccatgga ctggacctgg a                                              21

<210> SEQ ID NO 2
<211> LENGTH: 40
<212> TYPE: DNA
<213> ORGANISM: Artificial Sequence
<220> FEATURE:
<223> OTHER INFORMATION: synthetic

<400> SEQUENCE: 2
cccatcaact cacactcttg tccaggggcc tgtcgaaacc                           40

<210> SEQ ID NO 3
<211> LENGTH: 40
<212> TYPE: DNA
```

```
<213> ORGANISM: Artificial Sequence
<220> FEATURE:
<223> OTHER INFORMATION: synthetic

<400> SEQUENCE: 3
ctggtttcga caggcccctg gacaagagtg tgagttgatg                            40

<210> SEQ ID NO 4
<211> LENGTH: 33
<212> TYPE: DNA
<213> ORGANISM: Artificial Sequence
<220> FEATURE:
<223> OTHER INFORMATION: synthetic

<400> SEQUENCE: 4
acgttccgga tgaggagacg gtgaccaggg ttc                                   33

<210> SEQ ID NO 5
<211> LENGTH: 1449
<212> TYPE: DNA
<213> ORGANISM: Artificial Sequence
<220> FEATURE:
<223> OTHER INFORMATION: synthetic

<400> SEQUENCE: 5
atggactgga cctggaggat ccttttcttg gtggcagcag ccacaggagc ccactcccag      60
gtgcagctgg tgcagtctgg ggctgaggtg aagaagcctg ggcctcagt gaaggtctcc      120 tgcaaggctt ctggatacac cttcaccggc tactatatgc actgggtgcg acaggcccct    180
ggacaagggc ttgagtggat gggatggatc aaccctaaca gtggtggcac aaactatgca    240
cagaagtttc agggcagggt caccatgacc ggggacacgt ccatcagcac agcctacatg    300
gagctgagca ggctgagatc tgacgacacg gccgtgtatt actgtgcgag aggctcctta    360
tattgtacta atggtgtatg ctttgactac tggggccagg gaaccctggt caccgtctcc    420
tcaaagcttt ccaaaacaac accccatca gtctatccac tggcccctgg gtgtggagat     480
acaactggtt cctccgtgac tctgggatgc ctggtcaagg gctacttccc tgagtcagtg    540
actgtgactt ggaactctgg atccctgtcc agcagtgtgc acaccttccc agctctcctg    600
cagtctggac tctacactat gagcagctca gtgactgtcc cctccagcac ttggccaagt    660
cagaccgtca cctgcagcgt tgctcaccca gccagcagca ccacggtgga caaaaaactt    720
gtccggagcg agcccagcgg gcccatttca caatcaacc cctgtcctcc atgcaaggag    780
tgtcacaaat gcccagctcc taacctcgag ggtggaccat ccgtcttcat cttccctcca    840
aatatcaagg atgtactcat gatctccctg acacccaagg tcacgtgtgt ggtggtggat    900
gtgagcgagg atgacccaga cgtccagatc agctggtttg tgaacaacgt ggaagtacac    960
acagctcaga cacaaaccca tagagaggat tacaacagta ctatccgggt ggtcagcacc   1020
ctccccatcc agcaccagga ctggatgagt ggcaaggagt tcaaatgcaa ggtcaacaac   1080
aaagacctcc catcacccat cgagagaacc atctcaaaaa ttaaagggct agtcagagct   1140
ccacaagtat acatcttgcc gccaccagca gagcagttgt ccaggaaaga tgtcagtctc   1200
acttgcctgg tcgtgggctt caacccggta gacatcagtg tggagtggac cagcaatggg   1260
catacagagg agaactacaa ggacaccgca ccagtcctgg actctgacgg ttcttacttc   1320
atatatagca agctcaatat gaaaacaagc aagtgggaga aacagattc cttctcatgc   1380 aacgtgagac acgagggtct gaaaaattac tacctgaaga gaccatctc ccggtctccg    1440 ggtaaatga                                                           1449
```

<210> SEQ ID NO 6
<211> LENGTH: 482
<212> TYPE: PRT
<213> ORGANISM: Artificial Sequence
<220> FEATURE:
<223> OTHER INFORMATION: synthetic

<400> SEQUENCE: 6

```
Met Asp Trp Thr Trp Arg Ile Leu Phe Leu Val Ala Ala Thr Gly
 1               5                  10                  15

Ala His Ser Gln Val Gln Leu Val Gln Ser Gly Ala Glu Val Lys Lys
                 20                  25                  30

Pro Gly Ala Ser Val Lys Val Ser Cys Lys Ala Ser Gly Tyr Thr Phe
             35                  40                  45

Thr Gly Tyr Tyr Met His Trp Val Arg Gln Ala Pro Gly Gln Gly Leu
     50                  55                  60

Glu Trp Met Gly Trp Ile Asn Pro Asn Ser Gly Gly Thr Asn Tyr Ala
 65                  70                  75                  80

Gln Lys Phe Gln Gly Arg Val Thr Met Thr Gly Asp Thr Ser Ile Ser
                 85                  90                  95

Thr Ala Tyr Met Glu Leu Ser Arg Leu Arg Ser Asp Asp Thr Ala Val
            100                 105                 110

Tyr Tyr Cys Ala Arg Gly Ser Leu Tyr Cys Thr Asn Gly Val Cys Phe
        115                 120                 125

Asp Tyr Trp Gly Gln Gly Thr Leu Val Thr Val Ser Ser Lys Leu Ser
    130                 135                 140

Lys Thr Thr Pro Pro Ser Val Tyr Pro Leu Ala Pro Gly Cys Gly Asp
145                 150                 155                 160

Thr Thr Gly Ser Ser Val Thr Leu Gly Cys Leu Val Lys Gly Tyr Phe
                165                 170                 175

Pro Glu Ser Val Thr Val Thr Trp Asn Ser Gly Ser Leu Ser Ser Ser
            180                 185                 190

Val His Thr Phe Pro Ala Leu Leu Gln Ser Gly Leu Tyr Thr Met Ser
        195                 200                 205

Ser Ser Val Thr Val Pro Ser Ser Thr Trp Pro Ser Gln Thr Val Thr
    210                 215                 220

Cys Ser Val Ala His Pro Ala Ser Ser Thr Thr Val Asp Lys Lys Leu
225                 230                 235                 240

Val Arg Ser Glu Pro Ser Gly Pro Ile Ser Thr Ile Asn Pro Cys Pro
                245                 250                 255

Pro Cys Lys Glu Cys His Lys Cys Pro Ala Pro Asn Leu Glu Gly Gly
            260                 265                 270

Pro Ser Val Phe Ile Phe Pro Pro Asn Ile Lys Asp Val Leu Met Ile
        275                 280                 285

Ser Leu Thr Pro Lys Val Thr Cys Val Val Asp Val Ser Glu Asp
    290                 295                 300

Asp Pro Asp Val Gln Ile Ser Trp Phe Val Asn Asn Val Glu Val His
305                 310                 315                 320

Thr Ala Gln Thr Gln Thr His Arg Glu Asp Tyr Asn Ser Thr Ile Arg
                325                 330                 335

Val Val Ser Thr Leu Pro Ile Gln His Gln Asp Trp Met Ser Gly Lys
            340                 345                 350

Glu Phe Lys Cys Lys Val Asn Asn Lys Asp Leu Pro Ser Pro Ile Glu
        355                 360                 365

Arg Thr Ile Ser Lys Ile Lys Gly Leu Val Arg Ala Pro Gln Val Tyr
```

```
                370              375             380
Ile Leu Pro Pro Pro Ala Glu Gln Leu Ser Arg Lys Asp Val Ser Leu
385                 390                 395                 400

Thr Cys Leu Val Val Gly Phe Asn Pro Gly Asp Ile Ser Val Glu Trp
                405                 410                 415

Thr Ser Asn Gly His Thr Glu Glu Asn Tyr Lys Asp Thr Ala Pro Val
                420                 425                 430

Leu Asp Ser Asp Gly Ser Tyr Phe Ile Tyr Ser Lys Leu Asn Met Lys
                435                 440                 445

Thr Ser Lys Trp Glu Lys Thr Asp Ser Phe Ser Cys Asn Val Arg His
                450                 455                 460

Glu Gly Leu Lys Asn Tyr Tyr Leu Lys Lys Thr Ile Ser Arg Ser Pro
465                 470                 475                 480

Gly Lys

<210> SEQ ID NO 7
<211> LENGTH: 1449
<212> TYPE: DNA
<213> ORGANISM: Artificial Sequence
<220> FEATURE:
<223> OTHER INFORMATION: synthetic

<400> SEQUENCE: 7
atggactgga cctggaggat ccttttcttg gtggcagcag ccacaggagc ccactcccag     60
gtgcagctgg tgcagtctgg ggctgaggtg aagaagcctg ggcctcagt gaaggtctcc    120 tgcaaggctt ctggatacac cttcaccggc tactatatgc actggtttcg acaggcccct    180
ggacaagagt gtgagttgat gggatggatc aaccctaaca gtggtggcac aaactatgca    240
cagaagtttc agggcagggt caccatgacc ggggacacgt ccatcagcac agcctacatg    300
gagctgagca ggctgagatc tgacgacacg gccgtgtatt actgtgcgag aggctcctta    360
tattgtacta tggtgtatg ctttgactac tggggccagg gaaccctggt caccgtctcc    420
tcaaagcttt ccaaaacaac accccatca gtctatccac tggcccctgg gtgtggagat    480
acaactggtt cctccgtgac tctgggatgc ctggtcaagg gctacttccc tgagtcagtg    540
actgtgactt ggaactctgg atccctgtcc agcagtgtgc acaccttccc agctctcctg    600
cagtctggac tctacactat gagcagctca gtgactgtcc cctccagcac ttggccaagt    660
cagaccgtca cctgcagcgt tgctcaccca gccagcagca ccacggtgga caaaaaactt    720
gtccggagcg agcccagcgg gcccatttca caatcaacc cctgtcctcc atgcaaggag    780
tgtcacaaat gcccagctcc taacctcgag ggtggaccat ccgtcttcat cttccctcca    840
aatatcaagg atgtactcat gatctccctg acacccaagg tcacgtgtgt ggtggtggat    900
gtgagcgagg atgacccaga cgtccagatc agctggtttg tgaacaacgt ggaagtacac    960
acagctcaga cacaaaccca tagagaggat tacaacagta ctatccgggt ggtcagcacc   1020
ctccccatcc agcaccagga ctggatgagt ggcaaggagt tcaaatgcaa ggtcaacaac   1080
aaagacctcc catcacccat cgagagaacc atctcaaaaa ttaaagggct agtcagagct   1140
ccacaagtat acatcttgcc gccaccagca gagcagttgt ccaggaaaga tgtcagtctc   1200
acttgcctgg tcgtgggctt caaccctgga gacatcagtg tggagtggac cagcaatggg   1260
catacagagg agaactacaa ggacaccgca ccagtcctgg actctgacgg ttcttacttc   1320
atatatagca agctcaatat gaaaacaagc aagtgggaga aaacagattc cttctcatgc   1380
aacgtgagac acgagggtct gaaaaattac tacctgaaga agaccatctc ccggtctccg   1440
```

-continued ggtaaatga 1449

<210> SEQ ID NO 8
<211> LENGTH: 482
<212> TYPE: PRT
<213> ORGANISM: Artificial Sequence
<220> FEATURE:
<223> OTHER INFORMATION: synthetic

<400> SEQUENCE: 8

```
Met Asp Trp Thr Trp Arg Ile Leu Phe Leu Val Ala Ala Thr Gly
  1               5                  10                  15

Ala His Ser Gln Val Gln Leu Val Gln Ser Gly Ala Glu Val Lys Lys
                 20                  25                  30

Pro Gly Ala Ser Val Lys Val Ser Cys Lys Ala Ser Gly Tyr Thr Phe
             35                  40                  45

Thr Gly Tyr Tyr Met His Trp Phe Arg Gln Ala Pro Gly Gln Glu Cys
         50                  55                  60

Glu Leu Met Gly Trp Ile Asn Pro Asn Ser Gly Gly Thr Asn Tyr Ala
 65                  70                  75                  80

Gln Lys Phe Gln Gly Arg Val Thr Met Thr Gly Asp Thr Ser Ile Ser
                 85                  90                  95

Thr Ala Tyr Met Glu Leu Ser Arg Leu Arg Ser Asp Asp Thr Ala Val
            100                 105                 110

Tyr Tyr Cys Ala Arg Gly Ser Leu Tyr Cys Thr Asn Gly Val Cys Phe
        115                 120                 125

Asp Tyr Trp Gly Gln Gly Thr Leu Val Thr Val Ser Ser Lys Leu Ser
    130                 135                 140

Lys Thr Thr Pro Pro Ser Val Tyr Pro Leu Ala Pro Gly Cys Gly Asp
145                 150                 155                 160

Thr Thr Gly Ser Ser Val Thr Leu Gly Cys Leu Val Lys Gly Tyr Phe
                165                 170                 175

Pro Glu Ser Val Thr Val Thr Trp Asn Ser Gly Ser Leu Ser Ser Ser
            180                 185                 190

Val His Thr Phe Pro Ala Leu Leu Gln Ser Gly Leu Tyr Thr Met Ser
        195                 200                 205

Ser Ser Val Thr Val Pro Ser Ser Thr Trp Pro Ser Gln Thr Val Thr
    210                 215                 220

Cys Ser Val Ala His Pro Ala Ser Ser Thr Thr Val Asp Lys Lys Leu
225                 230                 235                 240

Val Arg Ser Glu Pro Ser Gly Pro Ile Ser Thr Ile Asn Pro Cys Pro
                245                 250                 255

Pro Cys Lys Glu Cys His Lys Cys Pro Ala Pro Asn Leu Glu Gly Gly
            260                 265                 270

Pro Ser Val Phe Ile Phe Pro Pro Asn Ile Lys Asp Val Leu Met Ile
        275                 280                 285

Ser Leu Thr Pro Lys Val Thr Cys Val Val Val Asp Val Ser Glu Asp
    290                 295                 300

Asp Pro Asp Val Gln Ile Ser Trp Phe Val Asn Asn Val Glu Val His
305                 310                 315                 320

Thr Ala Gln Thr Gln Thr His Arg Glu Asp Tyr Asn Ser Thr Ile Arg
                325                 330                 335

Val Val Ser Thr Leu Pro Ile Gln His Gln Asp Trp Met Ser Gly Lys
            340                 345                 350

Glu Phe Lys Cys Lys Val Asn Asn Lys Asp Leu Pro Ser Pro Ile Glu
        355                 360                 365
```

Arg Thr Ile Ser Lys Ile Lys Gly Leu Val Arg Ala Pro Gln Val Tyr
    370                 375                 380

Ile Leu Pro Pro Pro Ala Glu Gln Leu Ser Arg Lys Asp Val Ser Leu
385                 390                 395                 400

Thr Cys Leu Val Val Gly Phe Asn Pro Gly Asp Ile Ser Val Glu Trp
                405                 410                 415

Thr Ser Asn Gly His Thr Glu Glu Asn Tyr Lys Asp Thr Ala Pro Val
            420                 425                 430

Leu Asp Ser Asp Gly Ser Tyr Phe Ile Tyr Ser Lys Leu Asn Met Lys
            435                 440                 445

Thr Ser Lys Trp Glu Lys Thr Asp Ser Phe Ser Cys Asn Val Arg His
    450                 455                 460

Glu Gly Leu Lys Asn Tyr Tyr Leu Lys Lys Thr Ile Ser Arg Ser Pro
465                 470                 475                 480

Gly Lys

<210> SEQ ID NO 9
<211> LENGTH: 1149
<212> TYPE: DNA
<213> ORGANISM: Artificial Sequence
<220> FEATURE:
<223> OTHER INFORMATION: synthetic

<400> SEQUENCE: 9
atggactgga cctggaggat cctttcttg gtggcagcag ccacaggagc ccactcccag        60
gtgcagctgg tgcagtctgg ggctgaggtg aagaagcctg ggcctcagt gaaggtctcc       120 tgcaaggctt ctggatacac cttcaccggc tactatatgc actgggtgcg acaggcccct      180
ggacaagggc ttgagtggat gggatggatc aaccctaaca gtggtggcac aaactatgca      240
cagaagtttc agggcagggt caccatgacc ggggacacgt ccatcagcac agcctacatg      300
gagctgagca ggctgagatc tgacgacacg gccgtgtatt actgtgcgag aggctcctta      360
tattgtacta atggtgtatg ctttgactac tggggccagg gaaccctggt caccgtctcc      420
tcatccggag agcccagcgg gcccatttca acaatcaacc cctgtcctcc atgcaaggag      480
tgtcacaaat gcccagctcc taacctcgag ggtggaccat ccgtcttcat cttccctcca      540
aatatcaagg atgtactcat gatctccctg acacccaagg tcacgtgtgt ggtggtggat      600
gtgagcgagg atgacccaga cgtccagatc agctggtttg tgaacaacgt ggaagtacac      660
acagctcaga cacaaaccca tagagaggat tacaacagta ctatccgggt ggtcagcacc      720
ctccccatcc agcaccagga ctggatgagt ggcaaggagt tcaaatgcaa ggtcaacaac      780
aaagacctcc catcacccat cgagagaacc atctcaaaaa ttaaagggct agtcagagct      840
ccacaagtat acatcttgcc gccaccagca gagcagttgt ccaggaaaga tgtcagtctc      900
acttgcctgg tcgtgggctt caaccctgga gacatcagtg tggagtggac cagcaatggg      960
catacagagg agaactacaa ggacaccgca ccagtcctgg actctgacgg ttcttacttc     1020
atatatagca agctcaatat gaaaacaagc aagtgggaga aaacagattc cttctcatgc     1080
aacgtgagac acgagggtct gaaaaattac tacctgaaga agaccatctc ccggtctccg     1140
ggtaaatga                                                             1149

<210> SEQ ID NO 10
<211> LENGTH: 382
<212> TYPE: PRT
<213> ORGANISM: Artificial Sequence
<220> FEATURE:

<223> OTHER INFORMATION: synthetic

<400> SEQUENCE: 10

```
Met Asp Trp Thr Trp Arg Ile Leu Phe Leu Val Ala Ala Thr Gly
  1               5                  10                  15

Ala His Ser Gln Val Gln Leu Val Gln Ser Gly Ala Glu Val Lys Lys
             20                  25                  30

Pro Gly Ala Ser Val Lys Val Ser Cys Lys Ala Ser Gly Tyr Thr Phe
         35                  40                  45

Thr Gly Tyr Tyr Met His Trp Val Arg Gln Ala Pro Gly Gln Gly Leu
     50                  55                  60

Glu Trp Met Gly Trp Ile Asn Pro Asn Ser Gly Thr Asn Tyr Ala
 65                  70                  75                  80

Gln Lys Phe Gln Gly Arg Val Thr Met Thr Gly Asp Thr Ser Ile Ser
             85                  90                  95

Thr Ala Tyr Met Glu Leu Ser Arg Leu Arg Ser Asp Asp Thr Ala Val
            100                 105                 110

Tyr Tyr Cys Ala Arg Gly Ser Leu Tyr Cys Thr Asn Gly Val Cys Phe
        115                 120                 125

Asp Tyr Trp Gly Gln Gly Thr Leu Val Thr Val Ser Ser Gly Glu
    130                 135                 140

Pro Ser Gly Pro Ile Ser Thr Ile Asn Pro Cys Pro Pro Cys Lys Glu
145                 150                 155                 160

Cys His Lys Cys Pro Ala Pro Asn Leu Glu Gly Gly Pro Ser Val Phe
                165                 170                 175

Ile Phe Pro Pro Asn Ile Lys Asp Val Leu Met Ile Ser Leu Thr Pro
            180                 185                 190

Lys Val Thr Cys Val Val Asp Val Ser Glu Asp Asp Pro Asp Val
        195                 200                 205

Gln Ile Ser Trp Phe Val Asn Asn Val Glu Val His Thr Ala Gln Thr
    210                 215                 220

Gln Thr His Arg Glu Asp Tyr Asn Ser Thr Ile Arg Val Val Ser Thr
225                 230                 235                 240

Leu Pro Ile Gln His Gln Asp Trp Met Ser Gly Lys Glu Phe Lys Cys
                245                 250                 255

Lys Val Asn Asn Lys Asp Leu Pro Ser Pro Ile Glu Arg Thr Ile Ser
            260                 265                 270

Lys Ile Lys Gly Leu Val Arg Ala Pro Gln Val Tyr Ile Leu Pro Pro
        275                 280                 285

Pro Ala Glu Gln Leu Ser Arg Lys Asp Val Ser Leu Thr Cys Leu Val
    290                 295                 300

Val Gly Phe Asn Pro Gly Asp Ile Ser Val Glu Trp Thr Ser Asn Gly
305                 310                 315                 320

His Thr Glu Glu Asn Tyr Lys Asp Thr Ala Pro Val Leu Asp Ser Asp
                325                 330                 335

Gly Ser Tyr Phe Ile Tyr Ser Lys Leu Asn Met Lys Thr Ser Lys Trp
            340                 345                 350

Glu Lys Thr Asp Ser Phe Ser Cys Asn Val Arg His Glu Gly Leu Lys
        355                 360                 365

Asn Tyr Tyr Leu Lys Lys Thr Ile Ser Arg Ser Pro Gly Lys
    370                 375                 380
```

<210> SEQ ID NO 11
<211> LENGTH: 1149
<212> TYPE: DNA

<210> SEQ ID NO 11
<211> LENGTH: 1149
<212> TYPE: DNA
<213> ORGANISM: Artificial Sequence
<220> FEATURE:
<223> OTHER INFORMATION: synthetic

<400> SEQUENCE: 11

```
atggactgga cctggaggat ccttttcttg gtggcagcag ccacaggagc ccactcccag    60
gtgcagctgg tgcagtctgg ggctgaggtg aagaagcctg ggcctcagt gaaggtctcc    120
tgcaaggctt ctggatacac cttcaccggc tactatatgc actggtttcg acaggcccct   180
ggacaagagt gtgagttgat gggatggatc aaccctaaca gtggtggcac aaactatgca   240
cagaagtttc agggcagggt caccatgacc ggggacacgt ccatcagcac agcctacatg   300
gagctgagca ggctgagatc tgacgacacg gccgtgtatt actgtgcgag aggctcctta   360
tattgtacta atggtgtatg ctttgactac tggggccagg gaaccctggt caccgtctcc   420
tcatccggag agcccagcgg gcccatttca acaatcaacc cctgtcctcc atgcaaggag   480
tgtcacaaat gcccagctcc taacctcgag ggtggaccat ccgtcttcat cttccctcca   540
aatatcaagg atgtactcat gatctccctg acacccaagg tcacgtgtgt ggtggtggat   600
gtgagcgagg atgacccaga cgtccagatc agctggtttg tgaacaacgt ggaagtacac   660
acagctcaga cacaaaccca tagagaggat tacaacagta ctatccgggt ggtcagcacc   720
ctccccatcc agcaccagga ctggatgagt ggcaaggagt tcaaatgcaa ggtcaacaac   780
aaagacctcc catcacccat cgagagaacc atctcaaaaa ttaaagggct agtcagagct   840
ccacaagtat acatcttgcc gccaccagca gagcagttgt ccaggaaaga tgtcagtctc   900
acttgcctgg tcgtgggctt caaccctgga gacatcagtg tggagtggac cagcaatggg   960
catacagagg agaactacaa ggacaccgca ccagtcctgg actctgacgg ttccttacttc  1020
atatatagca agctcaatat gaaaacaagc aagtgggaga aaacagattc cttctcatgc   1080
aacgtgagac acgagggtct gaaaaattac tacctgaaga gaccatctc ccggtctccg    1140
ggtaaatga                                                            1149
```

<210> SEQ ID NO 12
<211> LENGTH: 382
<212> TYPE: PRT
<213> ORGANISM: Artificial Sequence
<220> FEATURE:
<223> OTHER INFORMATION: synthetic

<400> SEQUENCE: 12

```
Met Asp Trp Thr Trp Arg Ile Leu Phe Leu Val Ala Ala Ala Thr Gly
  1               5                  10                  15

Ala His Ser Gln Val Gln Leu Val Gln Ser Gly Ala Glu Val Lys Lys
             20                  25                  30

Pro Gly Ala Ser Val Lys Val Ser Cys Lys Ala Ser Gly Tyr Thr Phe
         35                  40                  45

Thr Gly Tyr Tyr Met His Trp Phe Arg Gln Ala Pro Gly Gln Glu Cys
     50                  55                  60

Glu Leu Met Gly Trp Ile Asn Pro Asn Ser Gly Gly Thr Asn Tyr Ala
 65                  70                  75                  80

Gln Lys Phe Gln Gly Arg Val Thr Met Thr Gly Asp Thr Ser Ile Ser
                 85                  90                  95

Thr Ala Tyr Met Glu Leu Ser Arg Leu Arg Ser Asp Asp Thr Ala Val
            100                 105                 110

Tyr Tyr Cys Ala Arg Gly Ser Leu Tyr Cys Thr Asn Gly Val Cys Phe
        115                 120                 125
```

Asp Tyr Trp Gly Gln Gly Thr Leu Val Thr Val Ser Ser Gly Glu
    130                 135                 140

Pro Ser Gly Pro Ile Ser Thr Ile Asn Pro Cys Pro Pro Cys Lys Glu
145                 150                 155                 160

Cys His Lys Cys Pro Ala Pro Asn Leu Glu Gly Gly Pro Ser Val Phe
                165                 170                 175

Ile Phe Pro Pro Asn Ile Lys Asp Val Leu Met Ile Ser Leu Thr Pro
                180                 185                 190

Lys Val Thr Cys Val Val Val Asp Val Ser Glu Asp Pro Asp Val
    195                 200                 205

Gln Ile Ser Trp Phe Val Asn Asn Val Glu Val His Thr Ala Gln Thr
    210                 215                 220

Gln Thr His Arg Glu Asp Tyr Asn Ser Thr Ile Arg Val Val Ser Thr
225                 230                 235                 240

Leu Pro Ile Gln His Gln Asp Trp Met Ser Gly Lys Glu Phe Lys Cys
                245                 250                 255

Lys Val Asn Asn Lys Asp Leu Pro Ser Pro Ile Glu Arg Thr Ile Ser
                260                 265                 270

Lys Ile Lys Gly Leu Val Arg Ala Pro Gln Val Tyr Ile Leu Pro Pro
    275                 280                 285

Pro Ala Glu Gln Leu Ser Arg Lys Asp Val Ser Leu Thr Cys Leu Val
    290                 295                 300

Val Gly Phe Asn Pro Gly Asp Ile Ser Val Glu Trp Thr Ser Asn Gly
305                 310                 315                 320

His Thr Glu Glu Asn Tyr Lys Asp Thr Ala Pro Val Leu Asp Ser Asp
                325                 330                 335

Gly Ser Tyr Phe Ile Tyr Ser Lys Leu Asn Met Lys Thr Ser Lys Trp
                340                 345                 350

Glu Lys Thr Asp Ser Phe Ser Cys Asn Val Arg His Glu Gly Leu Lys
            355                 360                 365

Asn Tyr Tyr Leu Lys Lys Thr Ile Ser Arg Ser Pro Gly Lys
    370                 375                 380

<210> SEQ ID NO 13
<211> LENGTH: 19
<212> TYPE: DNA
<213> ORGANISM: Artificial Sequence
<220> FEATURE:
<223> OTHER INFORMATION: synthetic

<400> SEQUENCE: 13
caacacaagt gcgatgcac                                              19

<210> SEQ ID NO 14
<211> LENGTH: 21
<212> TYPE: DNA
<213> ORGANISM: Artificial Sequence
<220> FEATURE:
<223> OTHER INFORMATION: synthetic

<400> SEQUENCE: 14
gattagcctc catgcctact c                                           21

<210> SEQ ID NO 15
<211> LENGTH: 21
<212> TYPE: DNA
<213> ORGANISM: Artificial Sequence
<220> FEATURE:
<223> OTHER INFORMATION: synthetic

<400> SEQUENCE: 15
gatgatcatg tgggtagacc t                                          21

<210> SEQ ID NO 16
<211> LENGTH: 20
<212> TYPE: DNA
<213> ORGANISM: Artificial Sequence
<220> FEATURE:
<223> OTHER INFORMATION: synthetic

<400> SEQUENCE: 16
tctatgctat ctcagtgcta                                            20

<210> SEQ ID NO 17
<211> LENGTH: 49
<212> TYPE: DNA
<213> ORGANISM: Artificial Sequence
<220> FEATURE:
<223> OTHER INFORMATION: synthetic

<400> SEQUENCE: 17
tgacagtgta atcacatata cttttcttg tagtcccaga agtatcatc              49

<210> SEQ ID NO 18
<211> LENGTH: 384
<212> TYPE: DNA
<213> ORGANISM: Artificial Sequence
<220> FEATURE:
<223> OTHER INFORMATION: synthetic

<400> SEQUENCE: 18
gaggtccagc ttcagcagtc tggagctgag ctggtgaggc ctgggtcctc agtgaagatg    60
tcctgcaaga cttctggata tacattcaca agctacggta taaactgggt gaagcagagg   120
cctggacagg gcctggaatg gattggatat atttatattg gaaatggtta tactgagtac   180
aatgagaagt tcaagggcaa ggccacactg acttcagaca catcctccag cacagcctac   240
atgcagctca gcagcctgac atctgaggac tctgcaatct atttccgtgc aagaggacgg   300
gtcggcccgt actactttga ctactggggc caaggcacca ctctcacagt ctcctcagtc   360
ccagaagtat catctgtctt catc                                         384

<210> SEQ ID NO 19
<211> LENGTH: 128
<212> TYPE: PRT
<213> ORGANISM: Artificial Sequence
<220> FEATURE:
<223> OTHER INFORMATION: synthetic

<400> SEQUENCE: 19

Glu Val Gln Leu Gln Gln Ser Gly Ala Glu Leu Val Arg Pro Gly Ser
1               5                   10                  15

Ser Val Lys Met Ser Cys Lys Thr Ser Gly Tyr Thr Phe Thr Ser Tyr
            20                  25                  30

Gly Ile Asn Trp Val Lys Gln Arg Pro Gly Gln Gly Leu Glu Trp Ile
        35                  40                  45

Gly Tyr Ile Tyr Ile Gly Asn Gly Tyr Thr Glu Tyr Asn Glu Lys Phe
    50                  55                  60

Lys Gly Lys Ala Thr Leu Thr Ser Asp Thr Ser Ser Ser Thr Ala Tyr
65                  70                  75                  80

Met Gln Leu Ser Ser Leu Thr Ser Glu Asp Ser Ala Ile Tyr Phe Arg
                85                  90                  95

Ala Arg Gly Arg Val Gly Pro Tyr Tyr Phe Asp Tyr Trp Gly Gln Gly
            100                 105                 110

Thr Thr Leu Thr Val Ser Ser Val Pro Glu Val Ser Ser Val Phe Ile
            115                 120                 125

<210> SEQ ID NO 20
<211> LENGTH: 381
<212> TYPE: DNA
<213> ORGANISM: Artificial Sequence
<220> FEATURE:
<223> OTHER INFORMATION: synthetic

<400> SEQUENCE: 20
gaggtccagc tgcaacagtc tggacgtgag ctggtcaagc ctggggcttc agtgatgata    60
tcttgtacgg cttctggata cacgttcatt gactacttca aaactggat gaagcggagc    120 catggacaga gccttgagtg gattggagat attaatccta caatggtgg ttctaactac    180 aaccagaagt tcaagggcaa ggccacattg actgtagaca gtcctccag acagcctac    240 atggatctcc gcagcctgac atctgaagac tctgcagtct attactgtgc aaaactggga    300
cgggactggt acttcgatgt ctggggcaca gggaccacgg tcaccgtctc ctcagtccca    360
gaagtatcat ctgtcttcat c    381

<210> SEQ ID NO 21
<211> LENGTH: 127
<212> TYPE: PRT
<213> ORGANISM: Artificial Sequence
<220> FEATURE:
<223> OTHER INFORMATION: synthetic

<400> SEQUENCE: 21

Glu Val Gln Leu Gln Gln Ser Gly Arg Glu Leu Val Lys Pro Gly Ala
  1               5                  10                  15

Ser Val Met Ile Ser Cys Thr Ala Ser Gly Tyr Thr Phe Ile Asp Tyr
             20                  25                  30

Phe Ile Asn Trp Met Lys Arg Ser His Gly Gln Ser Leu Glu Trp Ile
         35                  40                  45

Gly Asp Ile Asn Pro Asn Asn Gly Gly Ser Asn Tyr Asn Gln Lys Phe
     50                  55                  60

Lys Gly Lys Ala Thr Leu Thr Val Asp Lys Ser Ser Thr Ala Tyr
 65                  70                  75                  80

Met Asp Leu Arg Ser Leu Thr Ser Glu Asp Ser Ala Val Tyr Tyr Cys
             85                  90                  95

Ala Lys Leu Gly Arg Asp Trp Tyr Phe Asp Val Trp Gly Thr Gly Thr
            100                 105                 110

Thr Val Thr Val Ser Ser Val Pro Glu Val Ser Ser Val Phe Ile
            115                 120                 125

<210> SEQ ID NO 22
<211> LENGTH: 375
<212> TYPE: DNA
<213> ORGANISM: Artificial Sequence
<220> FEATURE:
<223> OTHER INFORMATION: synthetic

<400> SEQUENCE: 22
caggtccaac tgcagcagcc tggggctgag cttgtgaagc ctggggcttc agtgaagctg    60
tcctgcaagg cttctggcta caccttcacc agctactgga tgcagtgggt aaaacagagg    120
cctggacagg gccttgagtg gatcggagag attgatcctt ctgatagcta tactaactac    180

```
aatcaaaagt tcaagggcaa ggccacattg actgtagaca catcctccag cacagcctac    240
atgcagctca gcagcctgac acctgaggac tctgcggtct attactgtgc aagatgtagg    300
tactactttg actactgggg ccaaggcacc actctcacag tctcctcagt cccagaagta    360
tcatctgtct tcatc                                                     375
```

```
<210> SEQ ID NO 23
<211> LENGTH: 125
<212> TYPE: PRT
<213> ORGANISM: Artificial Sequence
<220> FEATURE:
<223> OTHER INFORMATION: synthetic

<400> SEQUENCE: 23
```

```
Gln Val Gln Leu Gln Gln Pro Gly Ala Glu Leu Val Lys Pro Gly Ala
 1               5                  10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Lys Ala Thr Leu Thr Val Asp Thr Ser Ser Ser Thr Ala Tyr
65                  70                  75                  80

Met Gln Leu Ser Ser Leu Thr Pro Glu Asp Ser Ala Val Tyr Tyr Cys
                85                  90                  95

Ala Arg Cys Arg Tyr Tyr Phe Asp Tyr Trp Gly Gln Gly Thr Thr Leu
           100                 105                 110

Thr Val Ser Ser Val Pro Glu Val Ser Ser Val Phe Ile
       115                  120                 125
```

```
<210> SEQ ID NO 24
<211> LENGTH: 393
<212> TYPE: DNA
<213> ORGANISM: Artificial Sequence
<220> FEATURE:
<223> OTHER INFORMATION: synthetic

<400> SEQUENCE: 24
```

```
gaggttcagt tgcagcagtc tggggcagag attgtgaagt caggggcctc agtcaagttg     60
tcctgcacag cttctggctt caacatgaaa gactacttta tccactgggt gaagcagagg    120
actgaacagg gcctggagtg gattggaagg cttgatcctg aggatggtaa aactaaatat    180
gccccgaaat tccagggcaa ggccactata acagcagaca catcctccaa cacagcctac    240
ctgcacctca gcagcctgac atctgaggac actgccgtct attactgtgc tagagggggga   300 ctgggacgtg aggaatacta tgctgtggac tactgggtc aaggaacctc agtcaccgtc    360
tcctcagtcc cagaagtatc atctgtcttc atc                                 393
```

```
<210> SEQ ID NO 25
<211> LENGTH: 131
<212> TYPE: PRT
<213> ORGANISM: Artificial Sequence
<220> FEATURE:
<223> OTHER INFORMATION: synthetic

<400> SEQUENCE: 25
```

```
Glu Val Gln Leu Gln Gln Ser Gly Ala Glu Ile Val Lys Ser Gly Ala
 1               5                  10                  15

Ser Val Lys Leu Ser Cys Thr Ala Ser Gly Phe Asn Met Lys Asp Tyr
```

```
                    20                  25                  30
Phe Ile His Trp Val Lys Gln Arg Thr Glu Gln Gly Leu Glu Trp Ile
                35                  40                  45
Gly Arg Leu Asp Pro Glu Asp Gly Lys Thr Lys Tyr Ala Pro Lys Phe
            50                  55                  60
Gln Gly Lys Ala Thr Ile Thr Ala Asp Thr Ser Ser Asn Thr Ala Tyr
65                  70                  75                  80
Leu His Leu Ser Ser Leu Thr Ser Glu Asp Thr Ala Val Tyr Tyr Cys
                85                  90                  95
Ala Arg Gly Gly Leu Gly Arg Glu Glu Tyr Tyr Ala Val Asp Tyr Trp
            100                 105                 110
Gly Gln Gly Thr Ser Val Thr Val Ser Ser Val Pro Glu Val Ser Ser
            115                 120                 125
Val Phe Ile
    130
```

```
<210> SEQ ID NO 26
<211> LENGTH: 387
<212> TYPE: DNA
<213> ORGANISM: Artificial Sequence
<220> FEATURE:
<223> OTHER INFORMATION: synthetic

<400> SEQUENCE: 26
gatgtacagc ttcaggagtc aggacctggc ctcgtgaaac cttctcagtc tctgtctctc      60
acctgctctg tcactggcta ctccatcacc agtggttatt actggaactg gatccggcag     120
tttccaggaa acaaactgga atggatgggc tacataagct acgatggtag aataactac      180
aacccatctc tcaaaaatcg aatctccatc actcgtgaca catctaagaa ccagtttttc     240
ctgaagttga attctgtgac tactgaggac acagccacat attactgtgc aatccatacg     300
gtagtagggg actatgttat ggactactgg ggtcaaggaa cctcagtcac cgtctcctca     360
gtcccagaag tatcatctgt cttcatc                                         387
```

```
<210> SEQ ID NO 27
<211> LENGTH: 129
<212> TYPE: PRT
<213> ORGANISM: Artificial Sequence
<220> FEATURE:
<223> OTHER INFORMATION: synthetic

<400> SEQUENCE: 27

Asp Val Gln Leu Gln Glu Ser Gly Pro Gly Leu Val Lys Pro Ser Gln
1               5                   10                  15
Ser Leu Ser Leu Thr Cys Ser Val Thr Gly Tyr Ser Ile Thr Ser Gly
                20                  25                  30
Tyr Tyr Trp Asn Trp Ile Arg Gln Phe Pro Gly Asn Lys Leu Glu Trp
            35                  40                  45
Met Gly Tyr Ile Ser Tyr Asp Gly Arg Asn Asn Tyr Asn Pro Ser Leu
        50                  55                  60
Lys Asn Arg Ile Ser Ile Thr Arg Asp Thr Ser Lys Asn Gln Phe Phe
65                  70                  75                  80
Leu Lys Leu Asn Ser Val Thr Thr Glu Asp Thr Ala Thr Tyr Tyr Cys
                85                  90                  95
Ala Ile His Thr Val Val Gly Asp Tyr Val Met Asp Tyr Trp Gly Gln
            100                 105                 110
Gly Thr Ser Val Thr Val Ser Ser Val Pro Glu Val Ser Ser Val Phe
        115                 120                 125
```

Ile

<210> SEQ ID NO 28
<211> LENGTH: 378
<212> TYPE: DNA
<213> ORGANISM: Artificial Sequence
<220> FEATURE:
<223> OTHER INFORMATION: synthetic

<400> SEQUENCE: 28

```
gaggttcagc tgcagcagtc tggggcagag cttgtgaggc caggggcctc agtcaagttg      60
tcctgcacag cttctggctt caacattaaa gactactata tacactgggt gaagaagagg     120
cctgaacagg gcctgagtg gattggaagg attgatcctg aggatggtga tactgagtat     180
gccccgaagt tccagggcaa ggccactatg actgcagaca catcctccaa cacagcctac     240
cttcagctca gcagcctgac atctgaggac attgccgtct attactgtac tacatctagg     300
ccttttattt ttgactactg gggccaaggc accactctca cagtctcctc agtcccagaa     360
gtatcatctg tcttcatc                                                   378
```

<210> SEQ ID NO 29
<211> LENGTH: 126
<212> TYPE: PRT
<213> ORGANISM: Artificial Sequence
<220> FEATURE:
<223> OTHER INFORMATION: synthetic

<400> SEQUENCE: 29

```
Glu Val Gln Leu Gln Gln Ser Gly Ala Glu Leu Val Arg Pro Gly Ala
 1               5                  10                  15
Ser Val Lys Leu Ser Cys Thr Ala Ser Gly Phe Asn Ile Lys Asp Tyr
            20                  25                  30
Tyr Ile His Trp Val Lys Lys Arg Pro Glu Gln Gly Leu Glu Trp Ile
        35                  40                  45
Gly Arg Ile Asp Pro Glu Asp Gly Asp Thr Glu Tyr Ala Pro Lys Phe
    50                  55                  60
Gln Gly Lys Ala Thr Met Thr Ala Asp Thr Ser Ser Asn Thr Ala Tyr
65                  70                  75                  80
Leu Gln Leu Ser Ser Leu Thr Ser Glu Asp Ile Ala Val Tyr Tyr Cys
                85                  90                  95
Thr Thr Ser Arg Pro Phe Tyr Phe Asp Tyr Trp Gly Gln Gly Thr Thr
            100                 105                 110
Leu Thr Val Ser Ser Val Pro Glu Val Ser Ser Val Phe Ile
        115                 120                 125
```

<210> SEQ ID NO 30
<211> LENGTH: 369
<212> TYPE: DNA
<213> ORGANISM: Artificial Sequence
<220> FEATURE:
<223> OTHER INFORMATION: synthetic

<400> SEQUENCE: 30

```
gaggttcagc tgcagcagtc tgggacagaa cttgtgaagc caggggcctc agccaagttg      60
tcctgcacag cttctggctt caacgttaaa gactactttg tgcactgggt gaagcagaag     120
actgaacagg gcctgagtg gattggaagg attgttcctg aggatggtga aactaagtct     180
gccccgaaat tccaggacag gaccactata agaacagaca catcctccaa cacatctcac     240
ctacaactca acagcctgac atctgaggac actgccgtct attactgtgc tagacctaac     300
```

```
cccccttact ggggccaagg gactctggtc actgtctctg tagtcccaga agtatcatct    360
gtcttcatc                                                             369

<210> SEQ ID NO 31
<211> LENGTH: 123
<212> TYPE: PRT
<213> ORGANISM: Artificial Sequence
<220> FEATURE:
<223> OTHER INFORMATION: synthetic

<400> SEQUENCE: 31

Glu Val Gln Leu Gln Gln Ser Gly Thr Glu Leu Val Lys Pro Gly Ala
1               5                   10                  15

Ser Ala Lys Leu Ser Cys Thr Ala Ser Gly Phe Asn Val Lys Asp Tyr
            20                  25                  30

Phe Met His Trp Val Lys Gln Lys Thr Glu Gln Gly Leu Glu Trp Ile
        35                  40                  45

Gly Arg Ile Val Pro Glu Asp Gly Glu Thr Lys Ser Ala Pro Lys Phe
    50                  55                  60

Gln Asp Arg Thr Thr Ile Arg Thr Asp Thr Ser Ser Asn Thr Ser His
65                  70                  75                  80

Leu Gln Leu Asn Ser Leu Thr Ser Glu Asp Thr Ala Val Tyr Tyr Cys
                85                  90                  95

Ala Arg Pro Asn Pro Pro Tyr Trp Gly Gln Gly Thr Leu Val Thr Val
            100                 105                 110

Ser Val Val Pro Glu Val Ser Ser Val Phe Ile
        115                 120

<210> SEQ ID NO 32
<211> LENGTH: 399
<212> TYPE: DNA
<213> ORGANISM: Artificial Sequence
<220> FEATURE:
<223> OTHER INFORMATION: synthetic

<400> SEQUENCE: 32
gaggtgaaac tggtggaatc tgaggaggc ttggttcagt ctgggcgttc tctgagactc    60
tcctgtgcaa cttctgggtt caccttcagt gatttctaca tggagtgggt ccgccaagct   120
ccagggaagg gactggagtg gattgctaca agtagaaaca aacttaatga ttatacacca   180
gaattcagtg catctgtgaa gggtcgattc atcgtctcca gagacacttc ccaaaacatc   240
ctctaccttc agatgaatgc cctgagacct gaggacactg ccatttatta ctgtgcaaga   300
gcctgtagtg actacgaccg ttactatgct atggactatt ggggtcaagg aacctcagtc   360
accgtctcct cagtcccaga agtatcatct gtcttcatc                          399

<210> SEQ ID NO 33
<211> LENGTH: 133
<212> TYPE: PRT
<213> ORGANISM: Artificial Sequence
<220> FEATURE:
<223> OTHER INFORMATION: synthetic

<400> SEQUENCE: 33

Glu Val Lys Leu Val Glu Ser Gly Gly Gly Leu Val Gln Ser Gly Arg
1               5                   10                  15

Ser Leu Arg Leu Ser Cys Ala Thr Ser Gly Phe Thr Phe Ser Asp Phe
            20                  25                  30

Tyr Met Glu Trp Val Arg Gln Ala Pro Gly Lys Gly Leu Glu Trp Ile
```

```
                35                   40                    45
Ala Thr Ser Arg Asn Lys Leu Asn Asp Tyr Thr Pro Glu Phe Ser Ala
 50                   55                    60

Ser Val Lys Gly Arg Phe Ile Val Ser Arg Asp Thr Ser Gln Asn Ile
 65                   70                    75                   80

Leu Tyr Leu Gln Met Asn Ala Leu Arg Pro Glu Asp Thr Ala Ile Tyr
                 85                   90                    95

Tyr Cys Ala Arg Ala Cys Ser Asp Tyr Asp Arg Tyr Tyr Ala Met Asp
                100                  105                   110

Tyr Trp Gly Gln Gly Thr Ser Val Thr Val Ser Ser Val Pro Glu Val
                115                  120                   125

Ser Ser Val Phe Ile
    130

<210> SEQ ID NO 34
<211> LENGTH: 399
<212> TYPE: DNA
<213> ORGANISM: Artificial Sequence
<220> FEATURE:
<223> OTHER INFORMATION: synthetic

<400> SEQUENCE: 34
caggtccaac tgcagcagcc tggggctgag cttgtgaagc ctggggcttc agtgaagctg     60
tcctgcaagg cttctggcta caccttcacc agctactgga tgcactgggt gaagcagagg    120
cctggacgag gccttgagtg gattggaagg attgatccta atagtggtgg tactaagtac    180
aatgagaagc tcaagaacaa ggccacactg actgtagaca aaccctccag cacagcctac    240
atgcagctca gcagcctgac atctgaggac tctgcggtct attattgtgc aagagaggag    300
ataaattact acggtagtac ctacggtgct atggactact ggggtcaagg aacctcagtc    360
accgtctcct cagtcccaga agtatcatct gtcttcatc                           399

<210> SEQ ID NO 35
<211> LENGTH: 133
<212> TYPE: PRT
<213> ORGANISM: Artificial Sequence
<220> FEATURE:
<223> OTHER INFORMATION: synthetic

<400> SEQUENCE: 35

Gln Val Gln Leu Gln Gln Pro Gly Ala Glu Leu Val Lys Pro Gly Ala
  1               5                    10                   15

Ser Val Lys Leu Ser Cys Lys Ala Ser Gly Tyr Thr Phe Thr Ser Tyr
                 20                   25                    30

Trp Met His Trp Val Lys Gln Arg Pro Gly Arg Gly Leu Glu Trp Ile
                 35                   40                    45

Gly Arg Ile Asp Pro Asn Ser Gly Gly Thr Lys Tyr Asn Glu Lys Leu
 50                   55                    60

Lys Asn Lys Ala Thr Leu Thr Val Asp Lys Pro Ser Ser Thr Ala Tyr
 65                   70                    75                   80

Met Gln Leu Ser Ser Leu Thr Ser Glu Asp Ser Ala Val Tyr Tyr Cys
                 85                   90                    95

Ala Arg Glu Glu Ile Asn Tyr Tyr Gly Ser Thr Tyr Gly Ala Met Asp
                100                  105                   110

Tyr Trp Gly Gln Gly Thr Ser Val Thr Val Ser Ser Val Pro Glu Val
                115                  120                   125

Ser Ser Val Phe Ile
    130
```

<210> SEQ ID NO 36
<211> LENGTH: 375
<212> TYPE: DNA
<213> ORGANISM: Artificial Sequence
<220> FEATURE:
<223> OTHER INFORMATION: synthetic

<400> SEQUENCE: 36

```
gaggtccagc tgcagcagtc tggacctgag ctggtgaagc ctggggcttc agtgaagata      60
tcctgcaagg cttctggtta ctcattcact ggctactaca tgaactgggt gaagcaaagt     120
cctgaaaaga gccttgagtg gattggagag attaatccta gcactggtgg tactacctac     180
aaccagaagt tcaaggccaa ggccacattg actgtagaca atcctccag cacagcctac      240
atgcagctca agagcctgac atctgaggac tctgcagtct attactgtgc aggtggttac     300
tggtacttcg atgtctgggg cacagggacc acggtcaccg tctcctcagt cccagaagta     360
tcatctgtct tcatc                                                      375
```

<210> SEQ ID NO 37
<211> LENGTH: 125
<212> TYPE: PRT
<213> ORGANISM: Artificial Sequence
<220> FEATURE:
<223> OTHER INFORMATION: synthetic

<400> SEQUENCE: 37

```
Glu Val Gln Leu Gln Gln Ser Gly Pro Glu Leu Val Lys Pro Gly Ala
 1               5                  10                  15
Ser Val Lys Ile Ser Cys Lys Ala Ser Gly Tyr Ser Phe Thr Gly Tyr
            20                  25                  30
Tyr Met Asn Trp Val Lys Gln Ser Pro Glu Lys Ser Leu Glu Trp Ile
        35                  40                  45
Gly Glu Ile Asn Pro Ser Thr Gly Gly Thr Thr Tyr Asn Gln Lys Phe
    50                  55                  60
Lys Ala Lys Ala Thr Leu Thr Val Asp Lys Ser Ser Ser Thr Ala Tyr
65                  70                  75                  80
Met Gln Leu Lys Ser Leu Thr Ser Glu Asp Ser Ala Val Tyr Tyr Cys
                85                  90                  95
Ala Gly Gly Tyr Trp Tyr Phe Asp Val Trp Gly Thr Gly Thr Thr Val
            100                 105                 110
Thr Val Ser Ser Val Pro Glu Val Ser Ser Val Phe Ile
        115                 120                 125
```

<210> SEQ ID NO 38
<211> LENGTH: 396
<212> TYPE: DNA
<213> ORGANISM: Artificial Sequence
<220> FEATURE:
<223> OTHER INFORMATION: synthetic

<400> SEQUENCE: 38

```
gaggtgcagc tggtggagtc tgggggagac ttagtggagc tggagggtc cctgaaactc       60
tcctgtgcag cctctggatt cactttcagt agctatggca tgtcttgggt tcgccagact     120
ccagacaaga ggctggagtg gtcgcaacc attagtagtg gtggtagtta cacctactat      180
ccagacagtg tgaaggggcg attcaccatc tccagagaca atgccaagaa caccctgtac    240
ctgcaaatga gcagtctgaa gtctgaggac acagccatgt attactgtgc aagacatgat    300
tactacggta gtagctacgg gtggtacttc gatgtctggg gcacagggac cacggtcacc    360
```
gtctcctcag tcccagaagt atcatctgtc ttcatc            396

<210> SEQ ID NO 39
<211> LENGTH: 132
<212> TYPE: PRT
<213> ORGANISM: Artificial Sequence
<220> FEATURE:
<223> OTHER INFORMATION: synthetic

<400> SEQUENCE: 39

Glu Val Gln Leu Val Glu Ser Gly Gly Asp Leu Val Glu Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Trp Val
        35                  40                  45

Ala Thr Ile Ser Ser Gly Gly Ser Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Asp Tyr Tyr Gly Ser Ser Tyr Gly Trp Tyr Phe Asp Val
            100                 105                 110

Trp Gly Thr Gly Thr Thr Val Thr Val Ser Ser Val Pro Glu Val Ser
        115                 120                 125

Ser Val Phe Ile
    130

<210> SEQ ID NO 40
<211> LENGTH: 24
<212> TYPE: DNA
<213> ORGANISM: Artificial Sequence
<220> FEATURE:
<223> OTHER INFORMATION: synthetic

<400> SEQUENCE: 40
cgatgggggc agggaaagct gcac            24

<210> SEQ ID NO 41
<211> LENGTH: 16
<212> TYPE: DNA
<213> ORGANISM: Artificial Sequence
<220> FEATURE:
<223> OTHER INFORMATION: synthetic

<400> SEQUENCE: 41
gtaaaacgac ggccag            16

<210> SEQ ID NO 42
<211> LENGTH: 17
<212> TYPE: DNA
<213> ORGANISM: Artificial Sequence
<220> FEATURE:
<223> OTHER INFORMATION: synthetic

<400> SEQUENCE: 42
caggaaacag ctatgac            17

<210> SEQ ID NO 43
<211> LENGTH: 21
<212> TYPE: DNA

```
<213> ORGANISM: Artificial Sequence
<220> FEATURE:
<221> NAME/KEY: variation
<222> LOCATION: (14)...(14)
<223> OTHER INFORMATION: s = c or g
<220> FEATURE:
<223> OTHER INFORMATION: synthetic

<400> SEQUENCE: 43
tcaccatgga ctgsacctgg a                                              21

<210> SEQ ID NO 44
<211> LENGTH: 22
<212> TYPE: DNA
<213> ORGANISM: Artificial Sequence
<220> FEATURE:
<221> NAME/KEY: variation
<222> LOCATION: (17)...(17)
<223> OTHER INFORMATION: y = c or t
<220> FEATURE:
<223> OTHER INFORMATION: synthetic

<400> SEQUENCE: 44
ccatggacac actttgytcc ac                                             22

<210> SEQ ID NO 45
<211> LENGTH: 23
<212> TYPE: DNA
<213> ORGANISM: Artificial Sequence
<220> FEATURE:
<223> OTHER INFORMATION: synthetic

<400> SEQUENCE: 45
tcaccatgga gtttgggctg agc                                            23

<210> SEQ ID NO 46
<211> LENGTH: 25
<212> TYPE: DNA
<213> ORGANISM: Artificial Sequence
<220> FEATURE:
<221> NAME/KEY: variation
<222> LOCATION: (14)...(14)
<223> OTHER INFORMATION: y = c or t
<220> FEATURE:
<223> OTHER INFORMATION: synthetic

<400> SEQUENCE: 46
agaacatgaa acayctgtgg ttctt                                          25

<210> SEQ ID NO 47
<211> LENGTH: 20
<212> TYPE: DNA
<213> ORGANISM: Artificial Sequence
<220> FEATURE:
<223> OTHER INFORMATION: synthetic

<400> SEQUENCE: 47
atggggtcaa ccgccatcct                                                20

<210> SEQ ID NO 48
<211> LENGTH: 23
<212> TYPE: DNA
<213> ORGANISM: Artificial Sequence
<220> FEATURE:
<223> OTHER INFORMATION: synthetic

<400> SEQUENCE: 48
acaatgtctg tctccttcct cat                                            23
```

<210> SEQ ID NO 49
<211> LENGTH: 21
<212> TYPE: DNA
<213> ORGANISM: Artificial Sequence
<220> FEATURE:
<223> OTHER INFORMATION: synthetic

<400> SEQUENCE: 49
gcaaggctta caaccacaat c    21

<210> SEQ ID NO 50
<211> LENGTH: 381
<212> TYPE: DNA
<213> ORGANISM: Artificial Sequence
<220> FEATURE:
<223> OTHER INFORMATION: synthetic

<400> SEQUENCE: 50
caggtgcagc tggtgcagtc tgggctgag gtgaagaagc ctggggcctc agtgaaggtc    60
tcctgcaagg cttctggata caccttcacc agttatgata tcaactgggt gcgacaggcc   120
actggacaag gcttgagtg gatgggatgg atgaaccca atagtggtaa gacaggctat    180
gcacagaagt tccagggcag agtcgccatg accaggaaaa cctccataag cacagcctac   240
atggagctga gcagcctgag atctgaggac acggccgtgt attactgtgc gagagaggac   300
tacagtaact acggggactt tgactactgg ggccaggaa ccctggtcac cgtctcctca   360
gtgcccaggg attgtggttg t    381

<210> SEQ ID NO 51
<211> LENGTH: 127
<212> TYPE: PRT
<213> ORGANISM: Artificial Sequence
<220> FEATURE:
<223> OTHER INFORMATION: synthetic

<400> SEQUENCE: 51

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Asp Ile Asn Trp Val Arg Gln Ala Thr Gly Gln Gly Leu Glu Trp Met
            35                  40                  45

Gly Trp Met Asn Pro Asn Ser Gly Lys Thr Gly Tyr Ala Gln Lys Phe
        50                  55                  60

Gln Gly Arg Val Ala Met Thr Arg Lys Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Tyr Ser Asn Tyr Gly Asp Phe Asp Tyr Trp Gly Gln
            100                 105                 110

Gly Thr Leu Val Thr Val Ser Ser Val Pro Arg Asp Cys Gly Cys
        115                 120                 125

<210> SEQ ID NO 52
<211> LENGTH: 378
<212> TYPE: DNA
<213> ORGANISM: Artificial Sequence
<220> FEATURE:
<223> OTHER INFORMATION: synthetic

<400> SEQUENCE: 52

```
caggttcagc tggtgcagtc tggagctgag atgaagaagc ctggggcctc agtgaaggtc      60
tcctgcaagg cttctggtta cacctttacc agctatggta tcagctgggt gcgacaggcc     120
cctggacaag gcttgagtg atgggatgg atcagcgctt acaatggtaa cacatactat      180
gcacagaacc tccagggcag agtcaccatg accacagaca catccacgag cgcagccttc     240
atggacctga ggagcctgag atctgacgac acggccgtgt attactgtgc gagagatggg     300
tatagtacct cgtccttaga ctactggggc cagggaaccc tggtcaccgt ctcctcagtg     360
cccagggatt gtggttgt                                                   378
```

<210> SEQ ID NO 53
<211> LENGTH: 126
<212> TYPE: PRT
<213> ORGANISM: Artificial Sequence
<220> FEATURE:
<223> OTHER INFORMATION: synthetic

<400> SEQUENCE: 53

```
Gln Val Gln Leu Val Gln Ser Gly Ala Glu Met Lys Lys Pro Gly Ala
 1               5                  10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Tyr Tyr Ala Gln Asn Leu
    50                  55                  60

Gln Gly Arg Val Thr Met Thr Thr Asp Thr Ser Thr Ser Ala Ala Phe
65                  70                  75                  80

Met Asp Leu Arg Ser Leu Arg Ser Asp Asp Thr Ala Val Tyr Tyr Cys
                85                  90                  95

Ala Arg Asp Gly Tyr Ser Thr Ser Ser Leu Asp Tyr Trp Gly Gln Gly
            100                 105                 110

Thr Leu Val Thr Val Ser Ser Val Pro Arg Asp Cys Gly Cys
        115                 120                 125
```

<210> SEQ ID NO 54
<211> LENGTH: 378
<212> TYPE: DNA
<213> ORGANISM: Artificial Sequence
<220> FEATURE:
<223> OTHER INFORMATION: synthetic

<400> SEQUENCE: 54

```
caggttcagc tggtgcagtc tggagctgag atgaagaagc ctggggcctc agtgaaggtc      60
tcctgcaagg cttctggtta cacctttacc agctatggta tcagctgggt gcgacaggcc     120
cctggacaag gcttgagtg atgggatgg atcagcgctt acaatggtaa cacatactat      180
gcacagaacc tccagggcag agtcaccatg accacagaca catccacgag cgcagccttc     240
atggacctga ggagcctgag atctgacgac acggccgtgt attactgtgc gagagatggg     300
tatagtacct cgtccttaga ctactggggc cagggaaccc tggtcaccgt ctcctcagtg     360
cccagggatt gtggttgt                                                   378
```

<210> SEQ ID NO 55
<211> LENGTH: 126
<212> TYPE: PRT
<213> ORGANISM: Artificial Sequence
<220> FEATURE:
<223> OTHER INFORMATION: synthetic -continued

```
<400> SEQUENCE: 55

Gln Val Gln Leu Val Gln Ser Gly Ala Glu Met Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Tyr Tyr Ala Gln Asn Leu
    50                  55                  60

Gln Gly Arg Val Thr Met Thr Thr Asp Thr Ser Thr Ser Ala Ala Phe
65                  70                  75                  80

Met Asp Leu Arg Ser Leu Arg Ser Asp Thr Ala Val Tyr Tyr Cys
                85                  90                  95

Ala Arg Asp Gly Tyr Ser Ser Ser Leu Asp Tyr Trp Gly Gln Gly
            100                 105                 110

Thr Leu Val Thr Val Ser Ser Val Pro Arg Asp Cys Gly Cys
        115                 120                 125

<210> SEQ ID NO 56
<211> LENGTH: 408
<212> TYPE: DNA
<213> ORGANISM: Artificial Sequence
<220> FEATURE:
<223> OTHER INFORMATION: synthetic

<400> SEQUENCE: 56
caggttcagc tggtgcagtc tggagctgag gtgaagaagc ctggggcctc agtgaaggtc      60
tcctgcaagg cttctggtta cacctttacc agctatggta tcagctgggt gcgacaggcc     120
cctggacaag gcttgagtg atgggatgg atcagcgctt acaatggtaa cacaaactat      180
gcacagaagc tccagggcag agtcaccatg accacagaca catccacgag cacagcctac     240
atggagctga ggagcctgag atctgacgac acggccgtgt attactgtgc gagagatgat     300
atgattacgt ttgggggagt tatcgccaac tactactact acggtatgga cgtctggggc     360
caagggacca cggtcaccgt cacctcagtg cccaggatt gtggttgt                    408

<210> SEQ ID NO 57
<211> LENGTH: 136
<212> TYPE: PRT
<213> ORGANISM: Artificial Sequence
<220> FEATURE:
<223> OTHER INFORMATION: synthetic

<400> SEQUENCE: 57

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Thr Ala Val Tyr Tyr Cys
                85                  90                  95

Ala Arg Asp Asp Met Ile Thr Phe Gly Gly Val Ile Ala Asn Tyr Tyr
            100                 105                 110
```

Tyr Tyr Gly Met Asp Val Trp Gly Gln Gly Thr Thr Val Thr Val Thr
                115                 120                 125

Ser Val Pro Arg Asp Cys Gly Cys
    130                 135

<210> SEQ ID NO 58
<211> LENGTH: 372
<212> TYPE: DNA
<213> ORGANISM: Artificial Sequence
<220> FEATURE:
<223> OTHER INFORMATION: synthetic

<400> SEQUENCE: 58
caggttcagt tgctgcagtc tggagctgag gtgaagaagc ctggggcctc agtgaaggtc      60
tcctacaagg cttctgatta cacctttacc agctatggta tcagctgggt gcgacaggcc    120
cctggacaag ggcttgagtg gatgggatgg atcagcgctt acaatggtaa cacaaactat    180
gcacagaacc tccagggcag agtcaccatg accacagaca catccacgag cacagcctac    240
atggaactga ggagcctgag atctgacgac tcggccgtgt attactgtgc gagagaggag    300
ctggaacttt ttgactactg gggccaggga accctggtca ccgtctcctc agtgcccagg    360
gattgtggtt gt                                                         372

<210> SEQ ID NO 59
<211> LENGTH: 124
<212> TYPE: PRT
<213> ORGANISM: Artificial Sequence
<220> FEATURE:
<223> OTHER INFORMATION: synthetic

<400> SEQUENCE: 59

Gln Val Gln Leu Leu Gln Ser Gly Ala Glu Val Lys Lys Pro Gly Ala
1               5                   10                  15

Ser Val Lys Val Ser Tyr Lys Ala Ser Asp Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Asn Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Ser Ala Val Tyr Tyr Cys
                85                  90                  95

Ala Arg Glu Glu Leu Glu Leu Phe Asp Tyr Trp Gly Gln Gly Thr Leu
            100                 105                 110

Val Thr Val Ser Ser Val Pro Arg Asp Cys Gly Cys
        115                 120

<210> SEQ ID NO 60
<211> LENGTH: 378
<212> TYPE: DNA
<213> ORGANISM: Artificial Sequence
<220> FEATURE:
<223> OTHER INFORMATION: synthetic

<400> SEQUENCE: 60
caggtccagc tggtgcagtc tggggctgag gtgaagaagc ctgggtcctc ggtgaaggtc      60
tcctgcaagg cttctggagg cacccttcagc agctatgcta tcagctgggt gcgacaggcc    120
cctggacaag ggcttgagtg gatgggaggg atcatcccta tctttggtac agcaaactac    180

```
gcacagaagt tccagggcag agtcacgatt accacggacg aatccacgag cacagcctac    240
atggagctga gcagcctgag atctgaggac acggccgtgt attactgtgc gagagatggg    300
tatagtacct cgtccttaga ctactggggc cagggaaccc tggtcaccgt ctcctcagtg    360
cccagggatt gtggttgt                                                   378
```

<210> SEQ ID NO 61
<211> LENGTH: 126
<212> TYPE: PRT
<213> ORGANISM: Artificial Sequence
<220> FEATURE:
<223> OTHER INFORMATION: synthetic

<400> SEQUENCE: 61

```
Gln Val Gln Leu Val Gln Ser Gly Ala Glu Val Lys Lys Pro Gly Ser
  1               5                  10                  15

Ser Val Lys Val Ser Cys Lys Ala Ser Gly Gly Thr Phe Ser Ser Tyr
             20                  25                  30

Ala Ile Ser Trp Val Arg Gln Ala Pro Gly Gln Gly Leu Glu Trp Met
         35                  40                  45

Gly Gly Ile Ile Pro Ile Phe Gly Thr Ala Asn Tyr Ala Gln Lys Phe
     50                  55                  60

Gln Gly Arg Val Thr Ile Thr Thr Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Gly Tyr Ser Thr Ser Ser Leu Asp Tyr Trp Gly Gln Gly
            100                 105                 110

Thr Leu Val Thr Val Ser Ser Val Pro Arg Asp Cys Gly Cys
            115                 120                 125
```

<210> SEQ ID NO 62
<211> LENGTH: 390
<212> TYPE: DNA
<213> ORGANISM: Artificial Sequence
<220> FEATURE:
<223> OTHER INFORMATION: synthetic

<400> SEQUENCE: 62

```
caggtccagc tggtgcagtc tggggctgag gtgaagaagc ctgggtcctc ggtgaaggtc     60
tcctgcaagg cttctggagg caccttcagc agctatgcta tcagctgggt gcgacaggcc    120
cctggacaag ggcttgagtg gatgggaggg atcatcccta tctttggtac agcaaactac    180
gcacagaagt tccagggcag agtcacgatt accacggacg aatccacgag cacagcctac    240
atggagctga gcagcctgag atctgaggac acggccgtgt attactgtgc ggttatagca    300
gtggctggta cctactacta ctacggtatg gacgtctggg gccaagggac cacggtcacc    360
gtctccttag tgcccaggga ttgtggttgt                                      390
```

<210> SEQ ID NO 63
<211> LENGTH: 130
<212> TYPE: PRT
<213> ORGANISM: Artificial Sequence
<220> FEATURE:
<223> OTHER INFORMATION: synthetic

<400> SEQUENCE: 63

```
Gln Val Gln Leu Val Gln Ser Gly Ala Glu Val Lys Lys Pro Gly Ser
  1               5                  10                  15
```

```
Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Thr Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Val Ile Ala Val Ala Gly Thr Tyr Tyr Tyr Gly Met Asp Val
                100                 105                 110

Trp Gly Gln Gly Thr Thr Val Thr Val Ser Leu Val Pro Arg Asp Cys
        115                 120                 125

Gly Cys
    130

<210> SEQ ID NO 64
<211> LENGTH: 101
<212> TYPE: DNA
<213> ORGANISM: Artificial Sequence
<220> FEATURE:
<223> OTHER INFORMATION: synthetic

<400> SEQUENCE: 64
tgacagtgta atcacatata ctttttcttg tagtgcccag ggattgtggt tgtaagcctt      60
gcatatgtac aggtaagtca gtaggccttt caccctgacc c                        101
```

MICE THAT MAKE HEAVY CHAIN ANTIBODIES

This application claims the benefit of the filing date under 35 USC §119(e), and is a nonprovisional, of U.S. Provisional Patent Application Ser. No. 61/285,250, filed 10 Dec. 2009, which provisional application is hereby incorporated by reference.

FIELD OF INVENTION

The field of invention is genetically modified non-human animals that make heavy chain antibodies, in particular genetically modified animals that comprise a nucleotide sequence deletion in a sequence encoding a CH1 domain (or CH1 domain and hinge region) of an immunoglobulin gamma (IgG) gene but that are capable of expressing an IgM that does not lack a functional CH1 domain, and in particular mice that are capable of making wild-type IgM molecules (i.e., with CH1 domains) but that make heavy chain IgG antibodies devoid of a functional CH1 domain (or CH1 domain and hinge region).

BACKGROUND

In most animals, normal immunoglobulin heavy chains are only well-expressed when coupled with their cognate light chains. In humans, lone heavy chains are found in heavy chain disease that is manifested by dysfunctional heavy chains that lack sequences of the variable heavy, the CH1, or the variable heavy and CH1 domains. Heavy chains devoid of light chains are encountered in certain species of fish and in camels. Such heavy chains lack a functional CH1 domain and have non-human features in their heavy chain variable domains. Attempts have been made to make camelized antibodies by modifying mice to express camelized genes that mimic VHH domains found in camels or certain species of fish, in part by removal of IgM and IgG CH1 domains and conforming the heavy chain variable regions to resemble those of camels and/or certain species of fish. However, camelized antibodies would be expected to induce immune responses in non-camel animals.

There is a need in the art for genetically modified non-human animals that make heavy chain antibodies that have non-camelid VH domains.

BRIEF DESCRIPTION OF THE FIGURES

FIG. 4 illustrates targeting a mouse heavy chain constant region locus to make a genetically modified locus that expresses an IgG1 lacking a CH1 domain, and does not express an IgG2b or an IgG2a.

FIG. 12 shows the protein sequences of eleven independent RT-PCR clones amplified from splenoctye RNA of mice bearing mouse heavy chain gene sequences at a modified endogenous mouse heavy chain locus devoid of IgG1 CH1 and hinge region sequences. B1=SEQ ID NO:19; B2=SEQ ID NO:21; B3=SEQ ID NO:23; B5=SEQ ID NO:25; D2=SEQ ID NO:27; D5=SEQ ID NO:29; D6=SEQ ID NO:31; E2=SEQ ID NO:33; E8=SEQ ID NO:35; E10=SEQ ID NO:37; F6=SEQ ID NO:39. Lower case bases indicate non-germline bases resulting from either mutation and/or N addition during recombination. Dots represent artificial gaps in the sequence for proper alignment of framework (FR) and complementary determining regions (CDR), which are noted above the sequences. The first nine amino acids from the CH2 region of the endogenous IgG1 (CH2) constant region are shown for each clone.

FIG. 13 shows the protein sequences of seven independent RT-PCR clones amplified from splenoctye RNA of mice bearing human heavy chain gene sequences at a modified endogenous mouse heavy chain locus devoid of an IgG1 CH1 region sequence. A8=SEQ ID NO:51; C2=SEQ ID NO:53; D9=SEQ ID NO:55; C4=SEQ ID NO:57; H8=SEQ ID NO:59; A5=SEQ ID NO:61; A2=SEQ ID NO:63. Lower case bases indicate non-germline bases resulting from either mutation and/or N addition during recombination. Dots represent artificial gaps in the sequence for proper alignment of framework (FR) and complementary determining regions (CDR), which are noted above the sequences. The first seven amino acids of the 13 amino acid hinge region of the endogenous IgG1 (HINGE) constant region are shown for each clone.

SUMMARY

Figure 1:
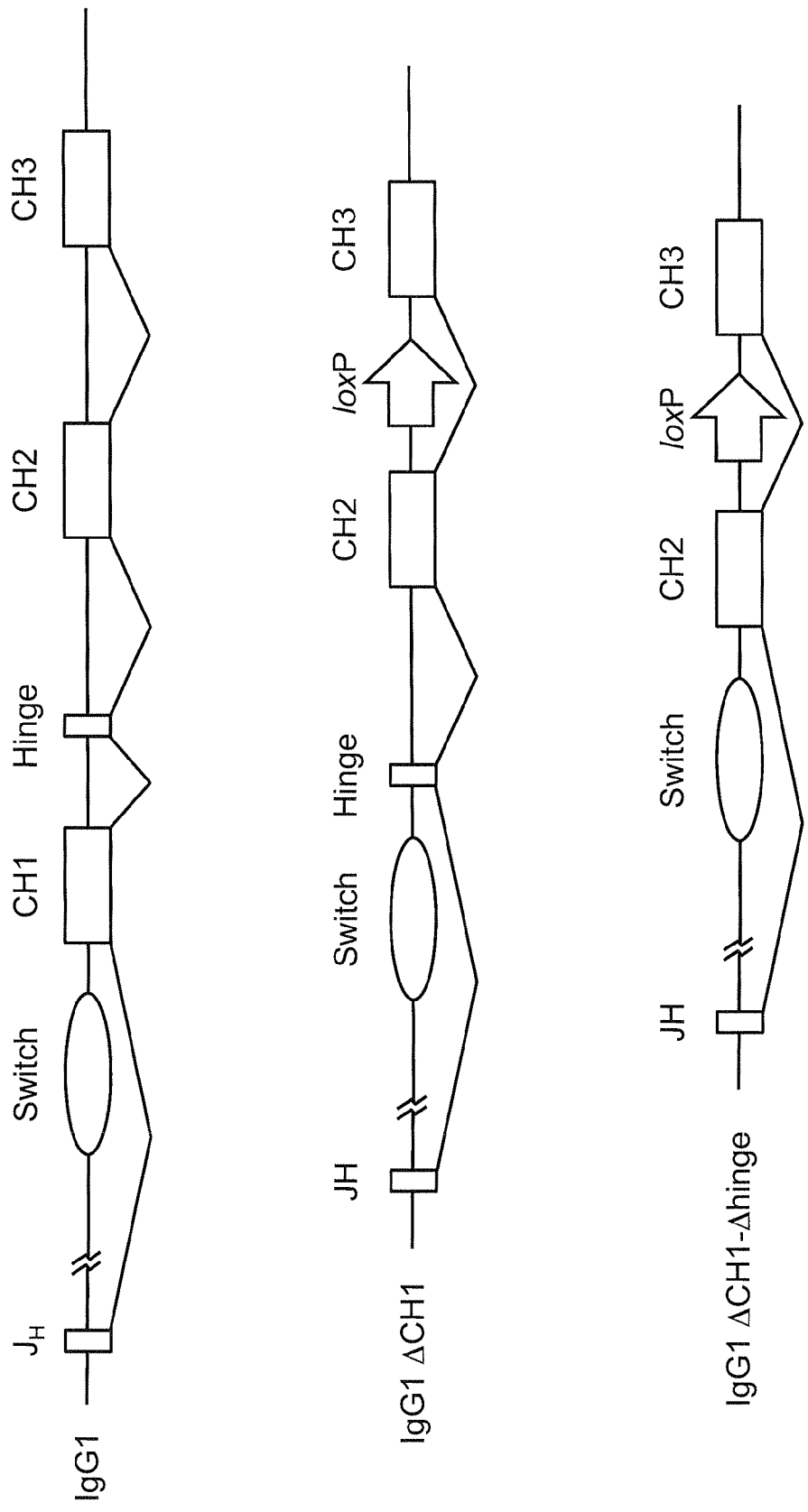
FIG. 1 illustrates a wild-type IgG1 locus in a mouse (IgG1, top), showing the JH region gene segment fusing to a CH1 gene segment, followed by a hinge region, a CH2 gene segment, and a CH3 gene segment; an IgG1 locus targeted with a construct that deletes a CH1 domain (IgG1ΔCH1, middle); and an IgG1 locus targeted with a construct that deletes both a CH1 domain and a hinge region (IgG1ΔCH1-Δhinge, bottom).

Genetically modified cells, non-human embryos, non-human animals and methods and compositions for making and using them are provided, wherein the animals are genetically modified to lack a functional CH1 sequence in an immunoglobulin G (IgG), optionally modified to lack a functional IgG hinge region on the modified IgG, and wherein the cells, embryos, and animals comprise a functional IgM CH1 sequence. In some aspects, the mice comprise a replacement of one or more, or all, endogenous mouse immunoglobulin heavy chain variable region gene segments with one or more human immunoglobulin heavy chain variable region gene segments. In some aspects, all endogenous mouse V, D, and J gene segments are replaced with one or more human V, one or more human D, and one or more human J gene segments.

In one aspect, a genetically modified mouse is provided, wherein the genetic modification comprises a modification of a nucleotide sequence encoding an IgG constant region, wherein the modification results in a loss of function of the CH1 domain of the IgG constant region. In one embodiment, the loss of function modification is a deletion of a nucleotide sequence encoding the CH1 domain, or a deletion within the nucleotide sequence encoding the CH1 domain.

In one embodiment, the IgG is selected from IgG1, IgG2a, IgG2b, and a combination thereof. In one embodiment, the IgG is an IgG1. In one embodiment, the IgG is an IgG1, an IgG2a, and an IgG2b.

In one embodiment, the modification further comprises a deletion of a nucleotide sequence for a hinge region of the IgG that comprises the CH1 modification.

In one embodiment, the genetically modified mouse is selected from a 129 strain, a C57BL/6 strain, and a mix of 129×C57BL/6. In a specific embodiment, the mouse is 50% 129 and 50% C57BL/6.

In one embodiment, the genetically modified mouse is a 129 strain selected from the group consisting of a 129P1, 129P2, 129P3, 129X1, 129S1 (e.g., 129S1/SV, 129S1/SvIm), 129S2, 129S4, 129S5, 129S9/SvEvH, 129S6 (129/SvEvTac), 129S7, 129S8, 129T1, 129T2 (see, e.g., Festing et al. (1999) Revised nomenclature for strain 129 mice, Mammalian Genome 10:836). In one embodiment the genetically modified mouse is a C57BL strain, in a specific embodiment selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, C57BL/Ola. In a specific embodiment, the genetically modified mouse is a mix of an aforementioned 129 strain and an aforementioned C57BL/6 strain. In another specific embodiment, the mouse is a mix of aforementioned 129 strains, or a mix of aforementioned BL/6 strains. In a specific embodiment, the 129 strain of the mix is a 129S6 (129/SvEvTac) strain.

In one embodiment, the mouse comprises one or more unrearranged endogenous mouse heavy chain immunoglobulin variable region (mVR) gene segments operably linked to the modified IgG constant region sequence. In one embodiment, the one or more mVR gene segments are from a mouse VH gene family selected from VH1, VH3, VH5, VH7, VH14, and a combination thereof. In one embodiment, the one or more mVR gene segments are selected from a mVH 1-26, 1-42, 1-50, 1-58, 1-72, 3-6, 5-6, 7-1, 14-2, and a combination thereof.

In one embodiment, the mouse comprises a rearranged gene that encodes an FR1, FR2, and an FR3 in an IgG heavy chain that lacks a functional CH1 region, wherein the FR1, FR2, and FR3 are each independently at least 90%, 95%, 96%, 97%, 98%, or 99% identical to an FR1, FR2, and FR3 derived from a mVH germline sequence selected from a VH1, VH3, VH5, VH7, and VH14 gene family. In one embodiment, the mVH germline sequence is selected from a 1-26, 1-42, 1-50, 1-58, 1-72, 3-6, 5-6, 7-1, and 14-2 sequence.

In one embodiment, the mouse comprises a CDR3 derived from a DH gene segment selected from DH 1-1, 2-14, 3-1, 3-2, 3-3, 4-1, and a combination thereof. In one embodiment, the mouse CDR3 comprises a sequence encoded by a JH that is a JH1, JH2, JH3, or JH4.

In one embodiment, the mouse comprises a rearranged antibody sequence that encodes a CDR3 that is derived from a rearrangement of a DH 1-1, 2-14, 3-1, 3-2, 3-3, 4-1, and a JH1, JH2, JH3, or JH4.

In one embodiment, the mouse comprises a rearranged gene that encodes an FR4 in an IgG heavy chain that lacks a functional CH1 region, wherein the FR4 is at least 90%, 95%, 96%, 97%, 98%, or 99% identical to an FR4 encoded by a rearrangement of a DH1-1, 2-14, 3-1, 3-2, 3-3, or 4-1 with a JH1, JH2, JH3, or JH4.

In one embodiment, the mouse comprises an unrearranged human heavy chain immunoglobulin variable region (hVR) gene segment at an endogenous mouse heavy chain variable region locus. In one embodiment, the mouse comprises an unrearranged hVR gene segment operably linked to the modified IgG constant region sequence at an endogenous mouse heavy chain variable region locus. In one embodiment, the hVR gene segments are from a human VH gene family selected from VH1, VH3, VH4, and a combination thereof. In one embodiment, the one or more hVR gene segments are selected from 1-2, 1-8, 1-18, 1-46, 1-69, 3-21, 3-72, and 4-59. In a specific embodiment, the one or more hVR gene segments are selected from 1-8, 1-18, and 1-69.

In one embodiment, all or substantially all mouse heavy chain V gene segments are replaced by one or more human heavy chain V gene segments. In one embodiment, all mouse heavy chain V and D gene segments are replaced by one or more human heavy chain V and D gene segments. In one embodiment, all mouse heavy chain V, D, and J gene segments are replaced with one or more human heavy cahin V, one or more human heavy chain D, and one or more human heavy chain J gene segments. In these embodiments, the human heavy chain V and/or D and/or J gene segments are at the mouse endogenous heavy chain locus and are operably linked to the mouse constant region gene(s) or modified mouse constant region gene(s).

In one embodiment, the mouse comprises a nucleotide sequence that encodes a FR1, FR2, and FR3 sequence of an IgG heavy chain that lacks a functional CH1 region, that is at least 80% identical to an FR1, FR2, and FR3 from a human germline nucleotide sequence of a 1-8, 1-18, or 1-69 human immunoglobulin heavy chain variable region gene segment; wherein the FR1+FR2+FR3 sequence of the modified mouse is optimally aligned with the recited human germline sequence without regard to the sequence of the CDRs of the mouse and human sequences (i.e., optimally aligning the FRs while not considering the identities of amino acids of any CDRs in the comparison). In specific embodiments, the FR1, FR2, and FR3 are about 85%, 90%, 95%, 96%, 97%, 98%, or 99% identical to a human germline nucleotide sequence of a FR1+FR2+FR3 of a heavy chain variable region gene segment that is a 1-8, 1-18, or 1-69 gene segment.

In one embodiment, the mouse further comprises a FR4 that is at least 80% identical to a FR4 formed by a human D6-19/J6 rearrangement, a D6-7/J4 rearrangement, a D4-4/J4 rearrangement, a D6-6/J2 rearrangement, a D3-16/J6 rearrangement, a D6-6/J4 rearrangement, and a D1-7/J4 rearrangement. In specific embodiments, the FR4 is about 85%, 90%, 95%, 96%, 97%, 98%, or 99% identical to an FR4 formed by the aforementioned D/J rearrangement.

In one embodiment, the mouse comprises a nucleotide sequence encoding a FR1 whose amino acid sequence differs by no more than 1, no more than 2, no more than 3, no more than 4, or no more than 5 amino acids from a FR1 encoded by a germline sequence of human heavy chain variable region gene segment selected from V1-8, V1-18, and V1-69. In a specific embodiment, the nucleotide sequence encoding the FR1 is a rearranged sequence operably linked to a sequence encoding an IgG constant region that lacks a functional CH1 sequence.

In one embodiment, the mouse comprises a nucleotide sequence encoding a FR2 whose amino acid sequence differs by no more than 1, no more than 2, no more than 3, no more than 4, or no more than 5 amino acids from a FR2 encoded by a germline sequence of human heavy chain variable region gene segment selected from V1-8, V1-18, and V1-69. In a specific embodiment, the nucleotide sequence encoding the FR2 is a rearranged sequence operably linked to a sequence encoding an IgG constant region that lacks a functional CH1 sequence.

In one embodiment, the mouse comprises a nucleotide sequence encoding a FR3 whose amino acid sequence differs by no more than 1, no more than 2, no more than 3, no more than 4, no more than 5, no more than 6, no more than 7, no more than 8, no more than 9, no more than 10, or no more than 11 amino acids from a FR3 encoded by a germline sequence of human heavy chain variable region gene segment selected from V1-8, V1-18, and V1-69. In a specific embodiment, the nucleotide sequence encoding the FR3 is a rearranged sequence operably linked to a sequence encoding an IgG constant region that lacks a functional CH1 sequence.

In one embodiment, the mouse comprises a nucleotide sequence encoding a FR4 whose amino acid sequence differs by no more than 1, no more than 2, or no more than 3 amino acids from a FR4 amino acid sequence encoded by a rearrangement of a human D6-19/J6, a D6-7/J4, a D4-4/J4, a D6-6/J2, a D3-16/J6, a D6-6/J4, and a D1-7/J4. In a specific embodiment, the nucleotide sequence encoding the FR4 is a rearranged sequence operably linked to a sequence encoding an IgG constant region that lacks a functional CH1 sequence.

In one embodiment, the mouse comprises a nucleotide sequence encoding a heavy chain CDR3 derived from a human heavy chain D region gene segment (hDH). In one embodiment, the hDH is selected from D1-7, D3-16, D4-4, D6-6, D6-7, and D6-19.

In one embodiment, the mouse comprises a nucleotide sequence encoding a heavy chain CDR3 derived from a human heavy chain joining gene segment (JH). In a specific embodiment, the JH is selected from J2, J4, and J6.

In one embodiment, the mouse comprises a heavy chain CDR3 encoded by a nucleotide sequence derived from a human DH and a human JH rearrangement. In a specific embodiment, the CDR3 is derived from a D1-7/J4, D3-16/J6, D4-4/J4, D6-6/J2, D6-6/J4, D6-7/J4, or a D6-19/J6 rearrangement.

In one embodiment, the mouse comprises a replacement of an endogenous mVR gene segment with an hVR gene segment. In a specific embodiment, the replacement of the mVR gene segment with the hVR gene segment is on the same allele as the modified heavy chain constant region. In another specific embodiment, the replacement of the mVR gene segment with the hVR gene segment is on a different allele than the modified heavy chain constant region.

In one embodiment, 90-100% of mVR gene segments are replaced with at least one hVR gene segment. In a specific embodiment, all or substantially all of the endogenous mVR gene segments are replaced with at least one hVR gene segment. In one embodiment, the replacement is with at least 18, at least 39, or at least 80 or 81 hVR gene segments. In one embodiment, the replacement is with at least 12 functional hVR gene segments, at least 25 functional hVR gene segments, or at least 43 functional hVR gene segments.

In one embodiment, the genetically modified mouse comprises a transgene that comprises at least one unrearranged hVR gene segment, at least one unrearranged human D segment, at least one unrearranged human J segment, and at least one human heavy chain constant sequence. In one embodiment, the endogenous mouse heavy chain variable region and kappa light chain variable region loci are functionally silenced. In a specific embodiment, the mouse is capable of trans-switching to produce a chimeric human/mouse antibody comprising a human heavy chain variable domain contiguous with a mouse IgG sequence that lacks a functional CH1 domain and, optionally, lacks a hinge region of the IgG that lacks the functional CH1 domain. In a specific embodiment, the transgene further comprises an IgG sequence that lacks a CH1 domain, and optionally comprises an IgM having a functional CH1 domain. In a further specific embodiment, the IgG sequence lacks a hinge region.

In one embodiment, the mouse comprises a first heavy chain variable region allele and a second heavy chain variable region allele, wherein the first allele and the second allele are both from the same mouse strain. In one embodiment, the first allele is from a first mouse strain and the second allele is from a second mouse strain. In one embodiment, one allele of the first and the second alleles comprises a replacement of an mVR with at least one hVR. In another embodiment, both alleles comprise a replacement of an mVR with at least on hVR.

In one aspect, a genetically modified mouse is provided, wherein the mouse expresses an IgM that comprises a CH1 domain, and the mouse expresses an IgG that lacks a functional CH1 domain or that expresses an IgG that lacks both a functional CH1 domain and that lacks a functional hinge region.

In one embodiment, the IgG is an IgG1.

In one embodiment, the mouse expresses four IgGs that are: a modified IgG1 and a wild-type IgG3, IgG2a, and IgG2b. In another embodiment, the mouse expresses no more than two IgGs that are: a modified IgG1 and a wild-type IgG3. In a specific embodiment the mouse expresses heavy chain isotypes that are: a wild-type IgM, a wild-type IgD, a wild-type IgG3, a modified IgG1, a wild-type IgG2a, a wild-type IgG2b, a wild-type IgA, and a wild-type IgE. In another specific embodiment, the mouse expresses heavy chain isotypes that are: a wild-type IgM, a wild-type IgD, a wild-type IgG3, a modified IgG1, a wild-type IgA, and a wild-type IgE. In various embodiments, the modification of the IgG1 comprises a deletion of a CH1 domain and, optionally, a deletion of a hinge region.

In one embodiment, the mouse is from a strain selected from 129, C56BL/6, a mixed 129×C57BL/6.

In one aspect, a mouse that expresses a heavy chain antibody is provided, wherein the heavy chain antibody consists essentially of a dimeric heavy chain, wherein the heavy chain lacks a functional CH1 domain or lacks both a functional CH1 domain and a functional hinge region, the heavy chain comprises a mammalian heavy chain variable domain that comprises a sequence that is not identical to a mammalian heavy chain variable domain encoded by a germline variable region gene, and the heavy chain comprises a human or mouse CH2 domain and a human or mouse CH3 domain, wherein the mouse expresses a wild-type human or mouse IgM.

In one embodiment, the mouse comprises a functional immunoglobulin light chain gene locus.

In one embodiment, wherein the mammalian heavy chain variable domain is a human or mouse heavy chain variable domain.

In one embodiment, the heavy chain antibody consists essentially of a dimeric heavy chain lacking a functional CH1 domain and lacking a functional hinge region, wherein the heavy chain comprises a human variable domain that comprises at least one somatic mutation and comprises a CH2 domain and a CH3 domain. In a specific embodiment, the CH2 domain and the CH3 domain are independently selected from mouse and human domains. In a specific embodiment, both the CH2 and the CH3 domain are human; in another embodiment, both the CH2 and the CH3 domain are mouse.

In one aspect, a heavy chain antibody is provided, wherein the heavy chain antibody comprises a heavy chain comprising a non-camelid variable domain and a heavy chain constant region lacking a CH1 domain.

In one embodiment, the heavy chain antibody further lacks a hinge region.

In one embodiment, the heavy chain antibody comprises a constant region that consists essentially of a hinge region, a CH2 domain, and a CH3 domain. In another embodiment, the heavy chain antibody comprises a constant region that consists essentially of a CH2 domain and a CH3 domain.

In one embodiment, the non-camelid variable domain is a somatically mutated human or mouse heavy chain variable domain obtained from an IgM- or an IgG-encoding nucleotide sequence of a B cell from a mouse or a genetically modified mouse comprising a human heavy chain variable region gene segment. In a specific embodiment, the mouse comprises a humanized heavy chain variable region gene segment. In another embodiment, the mouse comprises a replacement of the endogenous mouse heavy chain variable region gene segment locus with at least one human variable region gene segment. In another embodiment, the mouse comprises a replacement of the endogenous mouse heavy chain locus with at least one human variable gene segment, at least one human D gene segment, and at least one human J gene segment. In a specific embodiment, the endogenous mouse immunoglobulin variable region locus is all or substantially all replaced with a human immunoglobulin variable region locus comprising a plurality of human V, D, and J gene segments.

In one embodiment, the non-camelid variable domain is a human or a mouse variable domain. In another embodiment, the non-camelid variable domain is a human or a mouse variable domain comprising one or more camelizing modifications. In a specific embodiment, the camelizing modification is selected from L11S, V37F, G44E, L45C, L45R, and W47G (Kabat numbering). In a specific embodiment, the camelizing modification is selected from V37F, G44E, and L45C. In a specific embodiment, the heavy chain variable domain comprises a complementarity determining region 3 (CDR3) that comprises two cysteines.

In one embodiment, the heavy chain antibody comprises a dimer of a first heavy chain comprising a first heavy chain variable domain and a second heavy chain comprising a second heavy chain variable domain, wherein each of the first and the second heavy chains lacks a CH1 domain (or lacks a CH1 domain and a hinge region). In one embodiment, the human variable domain of the first heavy chain of the dimer binds a first epitope, and the human variable domain of the second heavy chain of the dimer binds a second epitope, wherein the first and the second epitope are not identical. In a specific embodiment, the heavy chain variable domains of the first and the second heavy chains comprise human heavy chain variable domains and/or human heavy chain FR regions as described herein.

In one aspect, a genetically modified non-human cell is provided, wherein the genetic modification comprises a deletion of an IgG CH1 domain and the cell expresses a functional IgM. In a specific embodiment, the cell comprises an IgM gene comprising a sequence encoding a CH1 domain.

In one embodiment, the cell is selected from a non-human ES cell, a pluripotent cell, and a totipotent cell. In a specific embodiment, the non-human ES cell is selected from a mouse ES cell and a rat ES cell.

In one aspect, a genetically modified non-human embryo is provided, wherein the genetic modification comprises a modification as described herein. In one embodiment, the genetic modification comprises a deletion of an IgG CH1 domain and the non-human embryo expresses a functional IgM. In a specific embodiment, the non-human embryo comprises an IgM gene comprising a CH1 domain.

In one embodiment, the non-human embryo is a mouse embryo or a rat embryo.

In one aspect, a non-human embryo comprising a donor cell is provided, wherein the donor cell is genetically modified, and wherein the genetic modification is a modification as described herein. In one embodiment, the genetic modification comprises a deletion of an IgG CH1 domain and the cell comprises an IgM gene comprising a CH1 domain.

In one embodiment, the non-human embryo is a mouse embryo or a rat embryo, and the donor cell is a mouse ES cell or a rat ES cell, respectively.

In one aspect, a DNA construct is provided, wherein the DNA construct comprises (a) a mouse homology arm homologous to a first sequence 5' and immediately adjacent to the start of an IgG CH1 region; (b) a marker or drug selection cassette; and, (c) a homology arm homologous to a second sequence 3' and immediately adjacent to the end of an IgG CH1 region or, alternatively, a homology arm homologous to a second sequence 3' and immediately adjacent to the end of an IgG hinge region.

In one aspect, a method for making an antibody that lacks a CH1 domain is provided, comprising: (a) immunizing a non-human animal as described herein that lacks a functional CH1 domain in an IgG or lacks a functional CH1 domain and lacks a functional hinge region in the IgG, wherein the mouse expresses an IgM that comprises a functional CH1 domain; (b) maintaining the non-human animal under conditions sufficient for the non-human animal to make an antibody; (c) identifying an antibody made by the mouse that lacks a functional CH1 domain or that lacks a functional hinge region; and, (d) isolating from the mouse the antibody, a cell that makes the antibody, or a nucleotide sequence that encodes a sequence of the antibody.

In one embodiment, the non-human animal comprises a functional immunoglobulin light chain gene locus.

In one aspect, a method for humanizing a mouse heavy chain antibody is provided, comprising immunizing a genetically modified mouse that makes heavy chain antibodies with an antigen of interest, allowing the mouse to mount an immune response, identifying a mouse VH region of the mouse that is encoded in a B cell of the mouse, wherein the B cell specifically binds the antigen of interest, and humanizing the VH region.

In one embodiment, the genetically modified mouse that makes heavy chain antibodies is a mouse as described herein. In one embodiment, the mouse comprises at least one mVR gene segment operably linked to a heavy chain constant locus that comprises an intact IgM gene and that comprises an IgG gene that lacks a CH1 domain or that lacks a CH1 domain and lacks a hinge domain. In one embodiment, the IgG gene is an IgG1 gene. In one embodiment, the IgG gene is selected from IgG1, IgG2A, IgG2B, IgG3, and a combination thereof.

In one embodiment, the method further comprises cloning a nucleotide sequence encoding the humanized VH region onto a nucleotide sequence of a human immunoglobulin constant region.

In one embodiment, the mouse mVR gene segment is from a mouse VH gene family selected from VH1 and VH14, and the humanization comprises replacing a mouse framework of VH1 or VH14 with a framework from a human VH1 gene. In one embodiment, the human VH1 gene is selected from 1-2, 1-3, 1-8, 1-17, 1-18, 1-24, 1-45, 1-46, 1-58, and 1-69. In specific embodiments, the mVR gene is a 1-58 gene and the human gene is a 1-18 gene; the mVR gene is a 1-26 gene and the human gene is a 1-2 gene; the mVR gene is a 1-50 gene and the human gene is a 1-46 gene; the mVR gene is a 1-17 gene and the human gene is a 1-2 gene; the mVR gene is a 1-42 gene and the human gene is a 1-2 gene; the mVR is a 14-1 gene and the human gene is a 1-2 gene; or the mVR is a 14-2 gene and the human gene is a 1-2 gene.

In one embodiment, the mVR gene segment is from a mouse VH gene selected from a VH4, VH5, VH6, VH7, VH10, VH11, and VH13 gene, and the humanization comprises replacing a mouse framework with a framework from a human VH3 gene. In one embodiment, the human VH3 gene is selected from 3-7, 3-9, 3-11, 3-13, 3-15, 3-16, 3-20, 3-21, 3-23, 3-30, 3-33, 3-35, 3-38, 3-43, 3-48, 3-49, 3-53, 3-64, 3-66, 3-72, 3-73, and 3-74. In a specific embodiment, the mVR gene is a 7-1 gene and the human gene is a 3-72 gene; the mVR gene is a 3-6 gene and the human gene is a 4-59 gene; the mVR gene is a 5-6 gene and the human gene is a 3-21 gene.

In one embodiment, the mVR gene segment is from a mouse VH gene family selected from VH3 and VH12, and the humanization comprises replacing a mouse framework with a framework from a human VH4 gene. In one embodiment, the human VH4 gene is selected from 4-4, 4-28, 4-31, 4-34, 4-39, 4-59, and 4-61.

In one embodiment, the mVR gene segment is from a mouse VH4 gene family, and the humanization comprises replacing a mouse VH4 framework with a framework from a human VH6 gene. In one embodiment, the human VH6 gene is 6-1.

In one embodiment, the mVR gene segment is from a mouse VH9 gene family, and the humanization comprises replacing a mouse VH9 framework with a framework from a human VH gene of the human VH7 family. In one embodiment, the human VH gene is selected from 7-4-1 and 7-81.

In one embodiment, the humanization further comprises making one or more conservative or non-conservative substitutions, one or more deletions, and/or one or more insertions in a mouse CDR such that the mouse CDR corresponds more closely to a human CDR.

In one embodiment, the humanization further comprises making one or more conservative or nonconservative substitutions, one or more deletions, and/or one or more insertions in a human framework such that the human framework corresponds more closely to the mouse framework.

In one aspect, a genetically modified mouse is provided that comprises a functional immunoglobulin light chain gene, wherein the mouse expresses a heavy chain antibody that lacks a light chain and that lacks a CH1 region or that lacks a CH1 region and a hinge region.

In one embodiment, the mouse comprises an immunoglobulin gene that lacks a sequence encoding a CH1 region, or lacks a sequence encoding a hinge and a CH1 region. In one embodiment, the immunoglobulin gene that lacks the sequence is one or more heavy chain constant genes. In a specific embodiment, the immunoglobulin gene that lacks the sequence is selected from an IgG1, IgG2a, IgG2b, and IgG3 gene. In a specific embodiment, the mouse comprises an IgM gene with a CH1 region, and/or a hinge region, and/or a CH1 region and hinge region.

In one embodiment, the antibody is expressed in response to an antigen, and the antibody specifically binds the antigen.

In one embodiment, the antibody comprises a mouse VH domain. In a specific embodiment, the mouse VH domain comprises a mouse VH gene segment selected from 1-26, 1-42, 1-50, 1-58, 1-72, 3-6, 5-6, 7-1, 14-1, and 14-2.

In one embodiment, the antibody comprises a human VH domain. In a specific embodiment, the human VH domain comprises a sequence derived from a human VH gene segment selected from 1-2, 1-18, 1-46, 3-21, 3-72, and 4-59.

In one aspect, a genetically modified mouse is provided that expresses a binding protein that consists essentially of two IgG1 heavy chains that each lack a CH1 domain, wherein the mouse expresses an IgM that comprises a CH1 region, and wherein the mouse is incapable of expressing from its genome an mRNA that comprises a nucleotide sequence encoding a CH1 domain of an IgG1.

In one embodiment, the immunoglobulin heavy chains that each lack a CH1 domain consist essentially of, from N-terminal to C-terminal, a human or mouse heavy chain immunoglobulin variable region, optionally a hinge region, a mouse CH2 region, and a mouse CH3 region. In a specific embodiment, the heavy chain immunoglobulin variable region is a human variable region, a hinge region is present, and the mouse comprises a functional immunoglobulin light chain gene locus.

In one aspect, a mouse is provided that expresses a heavy chain antibody that lacks a light chain and that lacks a CH1 region in whole or in part, wherein the mouse expresses a B cell receptor on a B cell, wherein the B cell receptor on its surface displays a binding molecule that comprises an immunoglobulin heavy chain variable domain fused directly to an immunoglobulin hinge region or fused directly to a CH2 region, wherein the binding molecule lacks a CH1 region. In one embodiment, the binding molecule comprises an IgG1 CH2 and CH3 region.

In one aspect, a method for making a heavy chain antibody is provided, comprising immunizing a mouse with an antigen of interest, wherein the mouse comprises an IgG gene that lacks a sequence encoding a CH1 region, wherein the mouse comprises an intact IgM constant region gene, allowing the mouse to mount an immune response against the antigen of interest, and isolating from the mouse a cell or protein that specifically recognizes the antigen of interest, wherein the cell or protein comprises a heavy chain antibody that lacks a CH1 domain and that lacks a cognate light chain and that specifically binds the antigen of interest.

In one embodiment, the mouse comprises a functional light chain gene. In one embodiment, the mouse comprises a functional light chain gene selected from lambda, kappa, and a combination thereof.

In one embodiment, the mouse comprises a replacement of all or substantially all mouse heavy chain V, D, J gene segments with one or more human V, D, J gene segments.

In one embodiment, the IgG gene that lacks the sequence encoding a CH1 is selected from an IgG1, IgG2a, IgG2b, IgG3, and a combination thereof.

In one embodiment, the IgG gene that lacks the CH1 sequence is IgG1, and the mouse lacks a gene encoding IgG2a, IgG2b, IgG3, or a combination thereof. In one embodiment, the IgG gene that lacks the CH1 sequence is IgG2a, and the mouse lacks a gene encoding IgG1, IgG2b, IgG3, or a combination thereof. In one embodiment, the IgG gene that lacks the CH1 sequence is IgG2b, and the mouse lacks a gene encoding IgG1, IgG2a, IgG3, or a combination thereof. In one embodiment, the IgG gene that lacks the CH1 sequence is IgG3, and the mouse lacks a gene encoding IgG1, IgG2a, IgG2b, or a combination thereof.

In one embodiment, the mouse comprises a B cell that bears on its surface a B cell receptor, wherein the B cell receptor comprises a rearranged heavy chain VDJ that binds the antigen of interest, and wherein the B cell receptor comprises an IgM that comprises a CH1 region, and wherein the IgM comprises a light chain. In one embodiment, the light chain is VJ rearranged. In a specific embodiment, the light chain is a kappa or a lambda light chain that is cognate with the rearranged heavy chain VDJ that binds the antigen of interest.

In one aspect, a mouse heavy chain antibody, human heavy chain antibody, or chimeric human/mouse heavy chain antibody made in a mouse according to the invention is provided.

In one aspect, a mouse heavy chain antibody, human heavy chain antibody, chimeric human/mouse heavy chain antibody, or humanized heavy chain antibody made using a heavy chain variable region nucleotide sequence or fragment thereof made in a mouse according to the invention is provided.

Other embodiments are described and will become apparent to those skilled in the art from a review of the ensuing detailed description.

DETAILED DESCRIPTION

The invention is not limited to particular methods, and experimental conditions described, as such methods and conditions may vary. The terminology used herein is for the purpose of describing particular embodiments only, and is not intended to be limiting, since the scope of the present invention will be limited only by the claims.

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, particular methods and materials are now described. All publications mentioned herein are incorporated herein by reference in their entirety.

CH1 Domains and Antibody Production

Genetically modified non-human animals are provided that make antibodies that lack a CH1 domain, including heavy chain antibodies, i.e., antibodies that lack light chains. The genetically modified non-human animals comprise a genetic modification that includes a lack of a functional immunoglobulin heavy chain domain (a CH1 domain), e.g., an IgG1 CH1 domain, and in some embodiments a further modification comprising a deletion of a hinge region in the immunoglobulin heavy chain that lacks the functional CH1 domain, wherein the non-human animal expresses a functional IgM. Other modifications include rendering isotypes other than IgG1 and IgM to be nonfunctional, e.g., making deletions in genes, or deletions of genes, for IgD, IgG3, IgG2a, IgG2b, IgA, and IgE. Genetically modified non-human embryos, cells, and targeting constructs for making the non-human animals, non-human embryos, and cells are also provided.

Efforts at making genetically modified cells that can make heavy chain antibodies (i.e., antibodies that lack a light chain) have focused on mimicking heavy chain antibodies in other species, e.g., in camelids and certain fish. This approach has been used to genetically modify a mouse ES cell to delete CH1 domains in immunoglobulin constant region genes of IgMs and IgGs, and also to introduce heavy chain variable regions into the ES cell that are camelid, or camelized VHH or VHH-like). The deletion of IgM and IgG CH1 domains is undertaken presumably to prevent formation of endogenous, natural antibodies to compete with camelized antibody formation from a genetically modified locus. The addition of VHH gene segments is undertaken presumably to mimic heavy chain antibody formation in combination with the CH1 deletion. Heavy chain antibodies from such animals will contain the VHH gene segment. VHH gene segments are presumably thought to be necessary for the proper expression of a heavy chain antibody, since in vitro studies indicate that non-camelid VH domains do not satisfactorily form expressible heavy chain antibodies when present in heavy chains lacking a CH1 domain.

In camelids, however (and in some cartilaginous fish), genes are present that include CH1 domains, or CH1-like domains. VHH-containing antibodies that lack CH1 domains are believed to result from RNA splicing or from rearrangement of DNA sequences that can encode a CH1 region. Thus, even camelids have retained DNA sequences encoding CH1 regions. Because humans (under some circumstances) can make heavy chain antibodies lacking a CH1 region in whole or in part (e.g., in human heavy chain disease), it might be possible to compel non-camelids, such as mice, to form heavy chains lacking a CH1 region under a given set of circumstances. This approach relies upon not disturbing the germline structure of a CH, but instead rendering the animal's light chain locus nonfunctional. This approach assumes that with a nonfunctional light chain locus those heavy chains that require a cognate light chain for expression (e.g., full-length heavy chains having CH1 regions) are not made due to the lack of any kappa or lambda light chain, such that only those heavy chains that can express and secrete without a light chain (i.e., heavy chains lacking a CH1 region) will be expressed and secreted. The approach relies upon the absence of functional kappa or lambda gene segments that can rearrange to form a functional light chain gene, and on the absence of any functional rearranged light chain gene, and thus requires a genetic manipulation (e.g., a knockout) to destroy functionality of both germline light chain loci. The approach relies upon "natural" processes leading to non-use of the endogenous CH1 nucleotide sequence, and that the "natural" process of CH1 silencing occurs in class switching. There does not appear to be any possibility of using such a process in any animal that contains a functional light chain gene. Furthermore, it appears that the "natural" process includes the synthesis of large amounts of normal RNA, i.e., RNA that includes a region encoding a CH1 region.

Compositions and methods are provided for making a mouse that makes an antibody that lacks an immunoglobulin CH1 domain (and optionally a hinge region), including heavy chain antibodies, and including antibodies that comprise VH domains (e.g., mouse or human VH domains). The methods include selectively rendering an endogenous non-IgM CH1 region to be nonfunctional (e.g., by a deletion of a sequence of a CH1 domain), and employing either unrearranged endogenous mouse variable region (mVR) gene segments or unrearranged human variable region (hVR) gene segments at the endogenous mouse variable region locus to make a chimeric human/mouse antibody in a mouse. The deletion of the CH1 domain is made in one or more IgG genes, but not in an IgM gene. The approach selectively renders one or more IgG CH1 domains nonfunctional while retaining a functional IgM. In addition to a deletion of the one or more IgG CH1 domains, a further embodiment provides for deleting or rendering nonfunctional the hinge region of the IgG(s) in which the CH1 domain is deleted or rendered nonfunctional.

The IgG CH1 deletion approach employs a relatively conservative disruption in natural B cell development in the animal, because not all Ig isotypes of the genetically modified non-human animal will exhibit a nonfunctional CH1 or a deletion of the CH1 domain (and, optionally, hinge). Thus, the CH1 modification does not occur in IgM molecules and thus does not affect those steps in early B cell development that depend on an IgM having a functional CH1. Because the IgM is not modified, animals bearing one or more deletions of the CH1 domain of an IgG (and optionally a hinge region of the IgG), but not an the CH1 domain of an IgM, should be able to process a satisfactorily large repertoire of variable regions in clonal selection steps prior to presentation of the variable domain in the context of an IgG. Thus in various embodiments, any deleterious affect of the genetic modification(s) on the diversity of variable regions available for use in a heavy chain antibody should not negatively impact the pool of variable regions available for selection in an IgG context. Further, where the CH1 sequence that is rendered nonfunctional (e.g., deleted) in the germline is an IgG1, the mouse will lack the ability to make any RNA that encodes a CH1 domain.

Genetically modifying a non-human animal to render a CH1 domain or a CH1 domain and a hinge region of one or more IgG isotypes nonfunctional may result in a mouse that is able to select, from a full or substantially full repertoire of VH regions, a suitable VH region to express in a heavy chain antibody. Selectively modifying IgG isotypes (but not IgM) avoids a potential reduction in the number of VH regions that survive selection due to a lack of a CH1 domain or a lack of a CH1 domain in IgM. Thus, a fuller repertoire of VH regions is available for selection in the context of an IgG (that lacks a CH1 domain or that lacks a CH1 domain and that lacks a hinge region). Thus, selection of a VH domain in a genetically modified mouse in accordance with the invention does not depend, e.g., on which VH domain might help overcome early IgM-dependent B cell developmental hurdles that are due to modified IgM structures. Instead, early IgM-dependent steps should occur as normal, resulting in a large repertoire of heavy chains available for selection as to their suitability to express in the context of an IgG that lacks a CH1 domain or that lacks a CH1 domain and lacks a hinge region.

Thus, in various embodiments, a genetically modified mouse in accordance with the invention should maintain functional IgM expression, which should provide an opportunity for a more natural clonal selection process. For example, with a functional IgM (e.g., an IgM that does not lack a CH1 domain), both surrogate light chain and the cognate light chain will be able to associate through the IgM's CH1 domain and participate in selection processes in early B cell development. In a genetically modified mouse in accordance with the invention, it is believed that class switching to an IgG isotype is the first selection step where any selection of heavy chain variable domains that can be expressed in the context of a constant domain lacking a functional CH1 domain or lacking a functional CH1 domain and a functional hinge is encountered.

IgM in B Cell Development

Although observations in camelids, certain fish, and in pathological conditions reveal that under some circumstances an antibody that lacks a CH1 domain of its heavy chain constant region can be expressed in the absence of a cognate light chain, normal development of antibody-producing B cells generally requires the presence of a CH1 domain. All heavy chain isotypes, including IgM, comprise a CH1 domain. Both the surrogate light chain and a cognate light chain are believed to interact with a given heavy chain through the heavy chain's CH1 domain in the context of an IgM. To the extent that development of heavy chain antibodies depends upon structural integrity or functionality of an IgM isotype heavy chain, disruption of the IgM's structural integrity or function would be undesirable.

Normal development of antibodies requires that antibodies survive throughout a multiplicity of complex selection schemes that result in the survival and ultimate expression of functional and useful antibodies. Disruptions in antibody structure can prove deleterious to the survival and ultimate expression of an antibody to the extent that the structural disruption results in the inability of the antibody to effectively compete and evolve to the satisfaction of one or more of nature's antibody selection schemes.

Early in antibody development, antibody heavy chains undergo a selection process wherein nature chooses, through a variety of selection schemes, suitable heavy chains to undergo further selection to eventually form functional and affinity-matured antibodies. Antibody heavy chains expressed from recombined heavy chain gene segments in progenitor B cells (or, pro-B cells) are normally paired with a surrogate light chain for presentation on the surface of the pro-B cell in an IgM isotype to form a structure (which includes other co-receptors) referred to as a pre-B cell receptor, or pre-BCR. Once the pre-BCR is presented on the cell surface, the pre-BCR is believed to signal its appropriate formation of the complex to the cell, effectively instructing the cell that the heavy chain has passed this early selection step. Thus the cell is informed that the heavy chain may undergo further selection. If the heavy chain contains a defect that is deleterious to the formation of a pre-BCR when presented in the context of an IgM and a surrogate light chain, the cell will undergo apoptosis. If the cell undergoes apoptosis, the usefulness, or contribution to diversity, of the heavy chain variable region of the heavy chain will be lost. Thus, a very early step in antibody selection requires presentation of the heavy chain together with a surrogate light chain in the context of an IgM isotype. The surrogate light chain is believed to interact with IgM at least in part through IgM's CH1 domain. A failure or disruption in antibody structure at this early juncture (e.g., a nonfunctional CH1 domain) can result in clonal selection failure, loss of the pro-B cell that expresses the heavy chain, and loss of the possibility of employing the particular heavy chain variable domain in a useful antibody.

Once the cell bearing the pre-BCR passes this selection step, the next selection step requires that the heavy chain be paired with a cognate light chain (e.g., either kappa or lambda in mice and humans). The paired heavy chain/cognate light chain structure is again presented on the surface of the cell, now a naive pre-B cell, in the context of an IgM isotype through the IgM's CH1 domain. This complex on the surface results in a functional, membrane-bound, B cell receptor (BCR). This BCR is believed to signal to the cell that the heavy chain is suitable for further selection, and that the cell may now commit to expressing this particular light chain and proceed to further B cell maturation steps, including affinity maturation and class switching. If the heavy chain contains a defect that is deleterious to the formation of a BCR when presented in the context of an IgM and its cognate light chain, the cell will undergo apoptosis. If the cell undergoes apoptosis, the usefulness, or contribution to diversity, of the heavy chain variable region of the heavy chain will be lost. Thus, a very early step in antibody selection requires presentation of the heavy chain together with a surrogate light chain in the context of an IgM isotype. Again, a failure or disruption in antibody structure (e.g., a non-functional CH1 domain) at this early juncture can result in clonal selection failure and concomitant loss of the pre-B cell that expresses the heavy chain.

Having survived selection thus far, the pre-B cell that presents the heavy chain paired with its cognate light chain in the IgM context then undergoes a maturation process that ultimately results in class switching and further selection mechanisms in which the heavy chain and cognate light chain are presented on the B cell surface in the context of an IgG isotype. It would be at this step that any selection of IgG heavy chains that lack a CH1 domain or that lack a CH1 domain and a hinge region would occur. In animals according to the invention, it is believed that a normal repertoire of heavy chain variable regions would be available for selection based upon whether the variable domain would survive to be expressed in an IgG heavy chain that lacks a CH1 domain or that lacks a CH1 domain and a hinge region. In contrast, mice that have impaired IgMs would likely not present a full repertoire of heavy chain variable regions, since only those variable regions capable of surviving selection in the context of an impaired IgM would be available for class switching.

Thus, an animal lacking a functional IgM may experience a marked reduction in the ability to make a B cell population following rearrangement of otherwise suitable heavy chain variable gene segments. In such a case, even where an ample supply of heavy chain variable regions is available (i.e., the animal has a suitable number of heavy chain variable region gene segments capable of rearranging), a satisfactory population of B cells that display a desirable degree of diversity may not form because of an IgM impairment that mitigates against survival of a heavy chain during the selection process.

Heavy Chain Antibody Production with a Functional IgM Gene

A suitable number of rearranged heavy chain variable regions that can effectively survive selection when presented during B cell development in the context of an IgM is desirable to be maintained in order to generate sufficient diversity to make antibodies by immunizing a non-human animal with an immunogen of interest. Thus, a genetically modified non-human animal that comprises a nonfunctional CH1 domain or a nonfunctional CH1 domain and a nonfunctional hinge region in an immunoglobulin heavy chain should not comprise a CH1 deletion in both IgM alleles.

In some embodiments, it is not desirable to delete CH1 domains of all Ig isotypes in order to make a heavy chain antibody in a genetically modified animal. Thus, methods and compositions are provided for making a heavy chain antibody in a genetically modified non-human animal by disabling, deleting, or otherwise rendering non-functional a nucleotide sequence encoding a CH1 domain or fragment thereof of an IgG (and in some embodiments also disabling, deleting, or otherwise rendering nonfunctional a hinge region of the IgG) while allowing other isotypes (e.g., IgM) to retain functional CH1 domains. It is believed that functionality of other isotype CH1 domains (other than one or more selected IgG CH1 domains) results in a B cell development process that does not disrupt or substantially disrupt developmental steps in which the heavy chain variable domain is presented in the context of a non-IgG isotype, e.g., in an IgM isotype. Thus disruption of, e.g., IgM-dependent steps during B cell development is relatively minimized. Without limitation as to the invention (which is described by the claims) the inventors propose that minimalizing disruption of early selection steps associated with presentation of the heavy chain variable domain in an IgM context will result in more cells that bear the heavy chain variable regions surviving to undergo class-switching to an IgG isotype and selection in the context of an IgG that lacks a functional CH1 domain or that lacks a functional CH1 domain and lacks a functional hinge region.

Accordingly, a genetically modified non-human animal is provided, along with methods and compositions for making the animal, wherein the genetic modification results in lack of a functional CH1 domain (in a further embodiment lack of a functional hinge region) in an Ig domain that is not an IgM domain. In various embodiments, a sequence encoding CH1 or the CH1 and the hinge region (or a substantially functional portion thereof) are deleted in the genome of the genetically modified animal. The genetically modified non-human animal is useful in making heavy chain antibodies (i.e., antibodies that lack a light chain), including fully human antibodies (in a mouse genetically modified to include human immunoglobulin genes) and chimeric human/mouse antibodies (e.g., in a mouse genetically modified to include human variable region gene segments, D regions, and J regions, or in a mouse having a human transgene capable of trans-switching to a genetically modified IgG isotype that lacks a functional CH1 domain or that lacks a functional CH1 domain and lacks a functional hinge region).

Heavy Chain Antibodies

Antibodies are useful as human therapeutics. Heavy chain antibodies, i.e., antibodies that lack a light chain, are also useful as human therapeutics. Because heavy chain antibodies lack a light chain, they are smaller and thus expected to exhibit better tissue penetration than antibodies that contain light chains, yet have a similar or more favorable pharmacokinetic profile and yet retain similar effector function as compared to a conventional antibody. Because they are smaller, heavy chain antibodies are also capable of administration at a higher dose in a given volume. A frequent method of administering antibodies is by subcutaneous injection, and a reduction in administration volume for a given dosage of antibody can provide benefits to patients and avoid complications and pain due to subcutaneous injections of large volumes.

Another advantage of heavy chain antibodies is the ability to make bispecific antibodies by heterodimerizing heavy chains with specificity for two different epitopes in a single therapeutics. Because heavy chain antibodies lack a light chain, they are particularly suited for making bispecific antibodies since there is no requirement to engineer a common light chain that would not interfere with binding affinity or specificity of either heavy chain but also enable suitable expression of the bispecific antibody.

The genetically modified animals of the invention can be used to make a wide variety of heavy chain antibodies. The genetic modifications described herein can be made, e.g., in any suitable mouse strain. The mouse strain can have any genetic background suitable for making a heavy chain antibody of choice. Some genetic backgrounds that encompass particular embodiments are provided below.

The genetically modified animal can be a mouse comprising a genetic modification in accordance with the invention and one or more unrearranged human variable region gene segments, one or more unrearranged D region gene segments, and one or more unrearranged J region gene segments replacing an endogenous mouse heavy chain variable region locus. In such a mouse, the humanized variable region locus is capable of recombining to form a rearranged variable region gene upstream of endogenous mouse constant domain sequences (wherein one or more of the immunoglobulin constant region genes is modified as described herein). The mouse would thus be capable of making a chimeric human variable/mouse constant heavy chain antibody. Upon exposure to an immunogen of interest, the mouse would be capable of generating a heavy chain antibody in accordance with the invention that is affinity matured and capable of specifically binding an epitope of the immunogen of interest.

The genetically modified animal can be a mouse comprising an endogenous mouse variable region that includes unrearranged endogenous mouse variable region gene segments, unrearranged endogenous mouse D region gene segments, and unrearranged endogenous mouse J region gene segments, wherein the mouse comprises a genetic modification of a mouse heavy chain constant region as described herein. The mouse would thus be capable of making a mouse heavy chain antibody. Upon exposure to an immunogen of interest, the mouse would be capable of generating a heavy chain antibody in accordance with the invention that is affinity matured and capable of specifically binding an epitope of the immunogen of interest.

The genetically modified animal can be a mouse comprising a human transgene that comprises unrearranged human variable region gene segments, unrearranged human D gene segments, and unrearranged human J gene segments, a mu gene, and a sequence that allows for trans-switching. The mouse would further comprise a mouse heavy chain constant region modification as described herein. The mouse would be thus capable of making a fully human IgM antibody, and through trans-switching a chimeric human variable/mouse constant antibody, wherein the constant domain comprises a genetic modification as described herein. Upon exposure to an immunogen of interest, the mouse would be capable of generating a heavy chain antibody in accordance with the invention that is affinity matured and capable of specifically binding an epitope of the immunogen of interest.

In Vitro Expression of Heavy Chain Antibodies

The inventors have established that a normal human or mouse heavy chain variable region (hVR or mVR) can be expressed in an in vitro system in the context of an IgG that lacks a functional CH1 domain. The inventors expressed an hVR from an unrearranged hVR minilocus in a mouse with a wild-type mouse IgM. The expressed hVR was cloned onto an IgG2b lacking a CH1 domain, and the resulting hVR-IgG2bΔCH1 expressed and was secreted by a CHO cell transiently transfected with the hVR-IgG2bΔCH1 construct, effectively establishing that an hVR selected in a mouse having a wild-type IgM can be expressed and secreted by a cell when switched to an IgG lacking a functional CH1 domain, i.e., as a heavy chain antibody.

The inventors constructed an in vitro system to express heavy chains that lack CH1 domains and that have hVRs or human camelized VRs (hVR*s) in CHO cells. The VRs were obtained from a RAG mouse that contained a replacement of the endogenous mouse heavy chain locus with a human heavy chain variable region minilocus (having three human V region gene segments, 6-1, 1-2, and 1-3, all human DH gene segments, and all human JH gene segments). The endogenous mouse immunoglobulin kappa and lambda light chain loci were intact and functional.

Chimeric heavy chain (hVR-mFc) and camelized heavy chain (hVR*-mFc) constructs were made, for expression in CHO cells, using the VR sequences obtained from the mouse bearing the minilocus described above. The chimeric heavy chains were the product of normal V-D-J recombination during B cell development in the mouse to form a functional antibody comprising a chimeric heavy chain (hVR-mFc) and a mouse light chain. hVR-mFc and hVR*-mFc constructs were made both having a CH1 domain and lacking a CH1 domain.

Transient transfection of hVR-mFc and hcVR-mFc constructs in CHO cells showed that in the absence of a CH1 domain, heavy chains having hVRs and hVR*s were expressed and remained soluble in the supernatant. In the presence of a CH1 domain, heavy chains containing either hVRs or hVR*s did not express in supernatant. This observation suggested that such heavy chain antibodies could be made without employing camelid VHH domains, e.g., with human or mouse VH domains, in heavy chain antibodies that lacked a CH1 domain.

Humanized Heavy Chain Antibodies

To produce a humanized version of a heavy chain antibody of the present invention, an animal homozygous for the modification is immunized with an antigen and once a specific immune response of the animal has been established, cells from the spleen of the immunized animal are fused with a suitable immortal cell (e.g., a myeloma cell) to produce hybridoma cells. Alternatively, the antibodies can be obtained directly from B cells of the immunized animal. Supernatants from the hybridoma cells (or, e.g., from isolated B cells) are screened for the presence of antibody by enzyme-linked immunosorbent assay (ELISA) and antibodies specific for the antigen can be selected based on desired characteristics.

Heavy chain variable region (VH) nucleic acids can be isolated from hybridoma and/or B cells using standard molecular biology techniques known in the art (Sambrook, et al. 1989. Molecular Cloning: A Laboratory Manual, Second Edition, Cold Spring Harbor, N.Y.; Ausubel, et al. 1995. Short Protocols in Molecular Biology, 3rd ed., Wiley & Sons). Once the VH nucleic acid sequence has been determined, the deduced amino acid sequence can be obtained and compared to other human VH sequences to identify a group of related VH sequences that have a similar sequence. Related VH sequences can be obtained using antibody databases available to those of skill in the art, e.g., The International ImMunoGeneTics Information System® (IMGT®). This comparison may be performed by alignment of the sequences accomplished either by eye or, alternatively, electronically by employing an alignment program (e.g., CLUSTAL). In this comparison, the complementary determining regions (CDRs) and framework regions (FRs) are identified. CDR and FR residues are determined according to a standard sequence definition (e.g., Kabat et al. 1987, Sequences of Proteins of Immunological Interest, National Institutes of Health, Bethesda Md.; Chothia and Lesk, 1987. J. Mol Biol. 196:901-917). Those skilled in the art will appreciate that there may occasionally exist discrepancies in methods of numbering and determining the CDR and FR regions of an immunoglobulin heavy chain sequence. In such cases, the structural definition is preferred, however, the residues identified by the sequence definition method are considered important FR residues for determination of which framework residues to substitute based on a comparison of heavy chain sequences.

Once aligned, substitutable positions in the VH sequences are identified. If the identity of an amino acid at a position in the isolated VH sequence varies when compared to the other human VH sequences, that position is evaluated for the suitability of a substitution at that position of the isolated VH sequence. Therefore, any position in the isolated VH sequence that varies with the other related human VH sequence(s) to which it is being compared can potentially serve as a position that could be substituted with the amino acid at the corresponding position found in one or any of the other related human VH sequences. Positions that share identity with the other related human VH sequences, i.e., those that do not demonstrate variability, are determined to be non-substitutable positions. In various embodiments, the above methods are employed to provide a consensus human heavy chain antibody sequence.

A humanized heavy chain antibody for the purposes described herein is an immunoglobulin heavy chain amino acid sequence variant or fragment thereof that is capable of binding to a predetermined antigen and that comprises a FR region having a substantially similar or an identical amino acid sequence as compared with a human FR amino acid sequence, and a CDR having a substantially similar or an identical amino acid sequence to a non-human CDR amino acid sequence. In general, a humanized heavy chain antibody has one or more amino acid residues that are derived from a non-human source. Such residues are typically derived from a heavy chain variable domain. Further, these residues may have associated characteristics such as, for example, affinity and/or specificity as well as other desirable biological activity associated with antibody function.

In various embodiments, the humanized heavy chain antibody comprises substantially all of at least one, and in other embodiments at least two, VH domains in which all or substantially all of the CDR regions correspond to those of a non-human VH domain and all or substantially all of the FR regions are those of a human VH domain sequence. The humanized heavy chain antibody will comprise a unique immunoglobulin constant region (Fc), that in one embodiment lacks at least the CH1 domain, and in one embodiment also lacks the hinge region of a human Fc. In one embodiment, the heavy chain antibody will not comprise a light chain and will comprise the CH2 and CH3 regions of an immunoglobulin G (IgG) heavy chain constant region. In one embodiment, the constant region of the heavy chain antibody will include the hinge, CH2 and CH3 regions of the IgG heavy chain Fc. In one embodiment, the constant region of the heavy chain antibody will include a CH1 region of an IgM.

The humanized heavy chain antibody will be selected from any class of IgGs, including IgG1, IgG2, IgG3 and IgG4. In various embodiments, the constant region may comprise sequences from more than one class of IgG, and selecting particular constant regions to optimize desired effector functions is within the ordinary skill in the art.

In general, the heavy chain FR and heavy chain CDR regions of the humanized heavy chain antibody need not correspond precisely to the parental sequences, e.g., the non-human heavy chain CDR or the human heavy chain FRs may be altered by substitution, insertion or deletion of at least one residue so that the heavy chain CDR or heavy chain FR residue at a given site does not correspond to either the human heavy chain FR sequence or the non-human heavy chain CDR sequence. Such mutations, however, will not be extensive. In one embodiment, at least 75% of the humanized heavy chain antibody residues will correspond to those of the parental heavy chain FR and heavy chain CDR sequences, in another embodiment 90%, and in another embodiment greater than 95%.

Humanized heavy chain antibodies as disclosed herein are, in one embodiment, prepared by a process of analyzing parental sequences and various conceptual humanized composite sequences in silico, using computer programs available and known to those skilled in the art. Sequence modifications to make humanized versions and/or for changing characteristics such as immunogenicity, affinity, etc. are made employing methods known in the art (e.g., U.S. Pat. No. 5,565,332 Hoogenboom et al.; U.S. Pat. No. 5,639,641 Pedersen et al.; U.S. Pat. No. 5,766,886 Studnicka et al.; U.S. Pat. No. 5,859,205 Adair et al.; U.S. Pat. No. 6,054,297 Carter et al.; U.S. Pat. No. 6,407,213 Carter et al.; U.S. Pat. No. 6,639,055 Carter et al.; U.S. Pat. No. 6,849,425 Huse et al.; U.S. Pat. No. 6,881,557 Foote; U.S. Pat. No. 7,098,006 Gorman et al.; U.S. Pat. No. 7,175,996 Watkins et al.; U.S. Pat. No. 7,235,643 Nicolaides et al.; U.S. Pat. No. 7,393,648 Rother et al.; U.S. Pat. No. 7,462,697 Couto et al.).

In various embodiments, desired substitutions to a parental heavy chain antibody sequence to make a variant of a parental heavy chain antibody are those that in one embodiment maintain, or in another embodiment increase, the antigen binding activity of the parental heavy chain antibody. In general, a heavy chain antibody variant of a parental heavy chain antibody has an antigen binding affinity that is at least 10%, at least 20%, at least 30%, at least 40%, at least 50%, at least 60%, at least 70%, at least 80%, at least 90% or at least 100% (e.g., at least 150%, at least 200%, at least 500%, at least 1000%, or up to at least 10,000%) of the binding affinity of the parental heavy chain antibody to a particular antigen. In some embodiments, a variant heavy chain antibody will comprise a single substitution as compared to a parental heavy chain antibody. However, in other embodiments, several amino acids, e.g., up to about 5 or 10 or more, are substituted as compared to the parental heavy chain antibody sequence that are derived from other human heavy chain sequences that share identity at a given position. Substitutions in one embodiment are conservative (i.e., an amino acid sharing similar properties to the residue to be replaced), and in another embodiment non-conservative (i.e., an amino acid sharing different properties to the residue to be replaced). In various embodiments, the resultant variant heavy chain antibody is tested to confirm that the desired binding affinity and/or specificity has not been significantly decreased by the replacement residues. In some embodiments, an improved variant heavy chain antibody is produced by the substitution of amino acids from a different human heavy chain sequence.

Naturally occurring heavy chain antibodies (e.g., found in camelids) have been demonstrated to contain unique amino acid residues at positions corresponding to the interface between heavy and light chain variable regions in traditional antibody molecules (i.e., two heavy chains and two light chains). These interface residues are known to affect the proximity or orientation of the two chains relative to one another in traditional antibodies. Although these natural heavy chain antibodies are known to contain replacement of residues that correlate with the absence of light chain variable regions, they retain the residues at other positions in the sequence as compared to traditional antibodies for preserving the characteristic immunoglobulin fold. The substitutions found in natural heavy chain antibodies are L11S, V37F, G44E, L45R or L45C, W47G and additional cysteine residues that contribute to a disulfide bond between the CDR1 and CDR3 of the heavy chain variable region. In some embodiments, heavy chain antibodies of the present invention may retain the residue of the parental antibody at these positions. In other embodiments, the parental antibody may display mutations at these positions that are associated with the residues in natural heavy chain antibodies. In some embodiments, it may be desirable to retain the same residue as is found in the parental heavy chain antibody at least one of these positions or, in one embodiment, all of these positions when making a humanized heavy chain antibody derived from an isolated VH sequence from a genetically modified mouse as described herein. In various embodiments, a person of skill in the art will understand that these interface residues are not reasonably expected to be involved in interchain interactions in heavy chain antibodies made by the genetically modified mouse as described herein.

Making Genetically Modified Animals

Genetic modifications for making an animal that expresses a heavy chain antibody are conveniently described by using the mouse as an illustration. A genetically modified mouse according to the invention can be made in a variety of ways, particular embodiments of which are discussed below.

A schematic illustration (not to scale) of an IgG1 locus is provided in FIG. 1 (top) to show CH domain arrangement at the IgG1 locus. As illustrated, domains CH1, CH2, and CH3 and the hinge region are present in readily identifiable spans of nucleotide downstream of a switch region.

Figure 2:
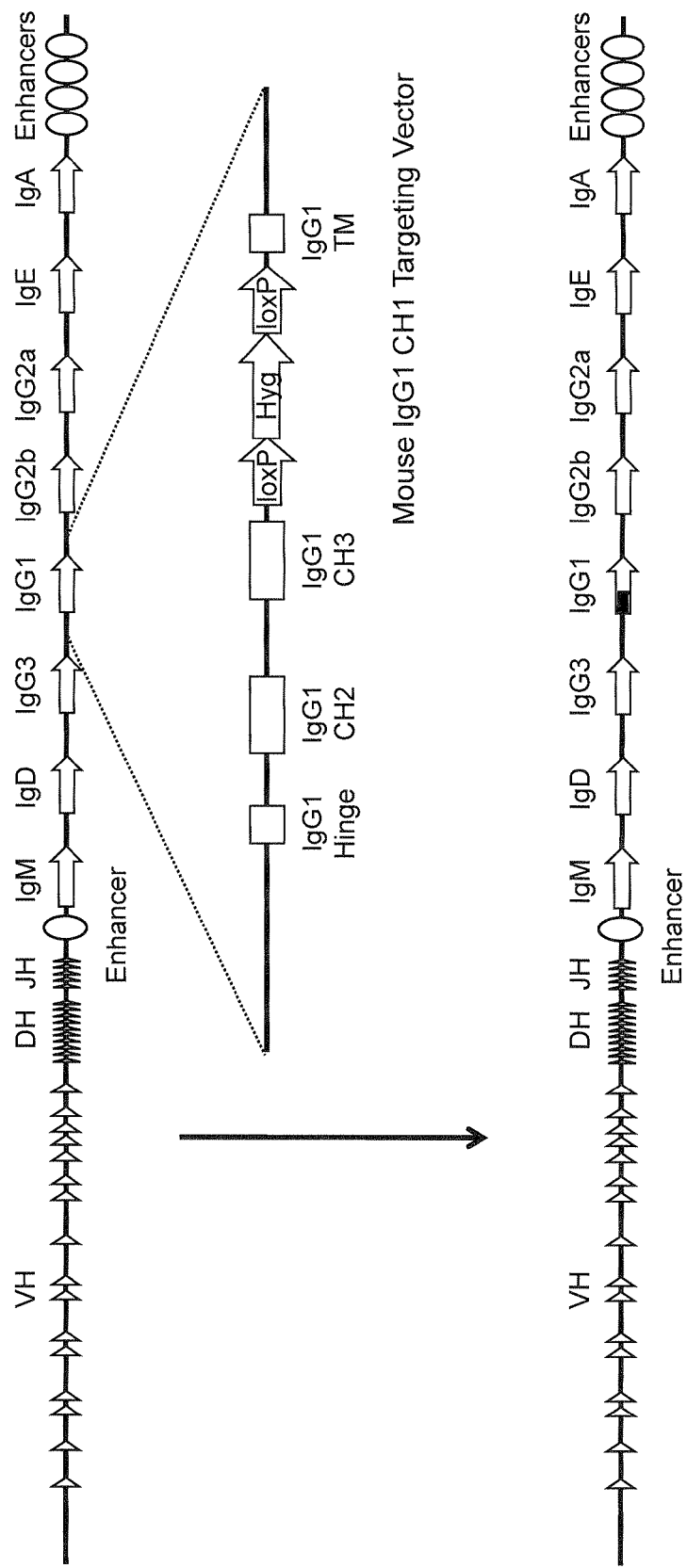
FIG. 2 illustrates targeting a mouse IgG1 gene to make a genetically modified locus that expresses an IgG1 lacking a CH1 domain.

A genetically modified mouse lacking a nucleotide sequence encoding a CH1 domain of an IgG1 but containing a hinge region can be made by any method known in the art. For example, a targeting vector can be made that replaces the IgG1 gene with a truncated IgG1 lacking a CH1 domain but containing the hinge. FIG. 2 illustrates a mouse genome (top) targeted by a targeting construct having a 5' (with respect to the direction of transcription of the genomic IgG1 gene) homology arm containing sequence upstream of the endogenous CH1 domain, followed by nucleotide sequences that encode an IgG1 hinge, an IgG1 CH2 domain, an IgG1 CH3 domain, a drug selection cassette (e.g., a loxed resistance gene), and an IgG1 transmembrane domain, and a 3' homology arm containing sequence 3' with respect to the transmembrane domain. Upon homologous recombination at the locus and removal of the drug selection cassette (e.g., by Cre treatment), the endogenous IgG1 is replaced by an IgG1 that lacks a CH1 domain (bottom of FIG. 2; lox site not shown). FIG. 1 (IgG1ΔCH1, middle) shows the structure of the resulting locus, which will express an IgG1 having a J region sequence fused to the hinge sequence.

Figure 3:
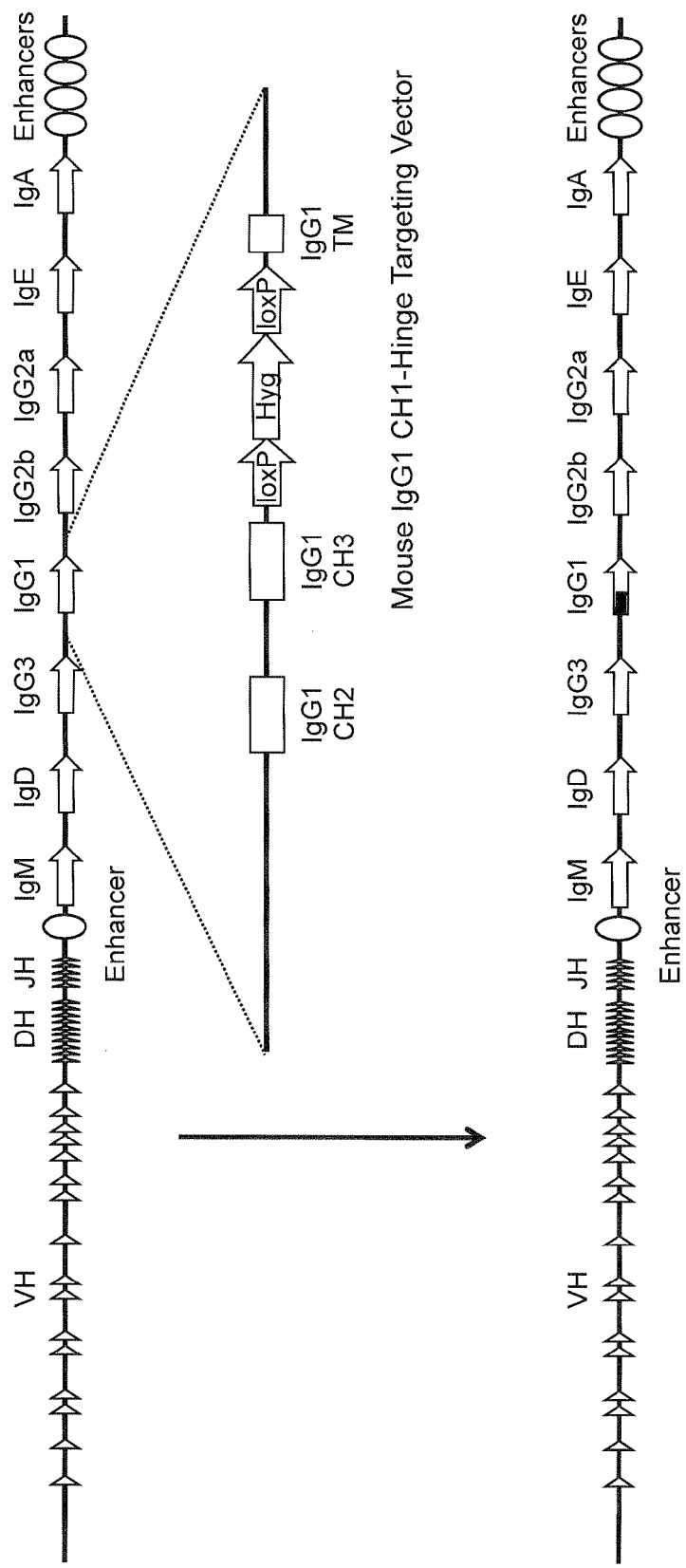
FIG. 3 illustrates targeting a mouse IgG1 gene to make a genetically modified locus that expresses an IgG1 lacking a CH1 domain and lacking a hinge region.

A genetically modified mouse lacking a nucleotide sequence encoding a CH1 domain of an IgG1 and lacking a nucleotide sequence encoding a hinge region can be made by any method known in the art. For example, a targeting vector can be made that replaces the IgG1 gene with a truncated IgG1 lacking a sequence encoding a CH1 domain and lacking a sequence encoding the hinge region. FIG. 3 illustrates a mouse genome (top) targeted by a targeting construct having a 5' (with respect to the direction of transcription of the genomic IgG1 gene) homology arm containing sequence upstream of the endogenous CH1 domain, followed by nucleotide sequences that encode an IgG1 CH2 domain, an IgG1 CH3 domain, a drug selection cassette (e.g., a loxed resistance gene), and an IgG1 transmembrane domain, and a 3' homology arm containing sequence 3' with respect to the transmembrane domain. Upon homologous recombination at the locus and removal of the drug selection cassette (e.g., by Cre treatment), the endogenous IgG1 gene is replaced by an IgG1 gene that lacks a sequence encoding a CH1 domain (bottom of FIG. 3; lox site not shown). FIG. 1 (IgG1ΔCH1-Δhinge, bottom) shows the structure of the resulting locus, which will express an IgG1 having a J region sequence fused to the CH2 domain.

Figure 4:
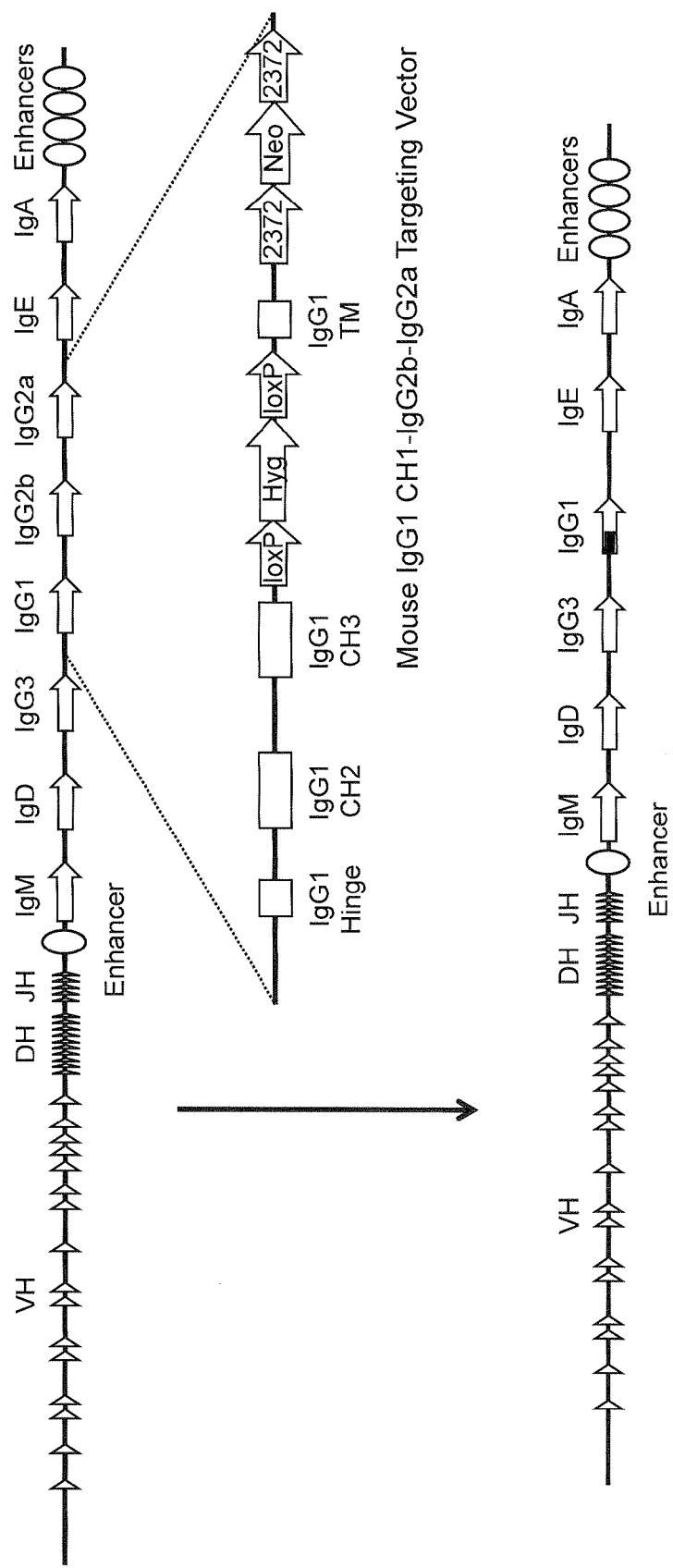
Figure 5:
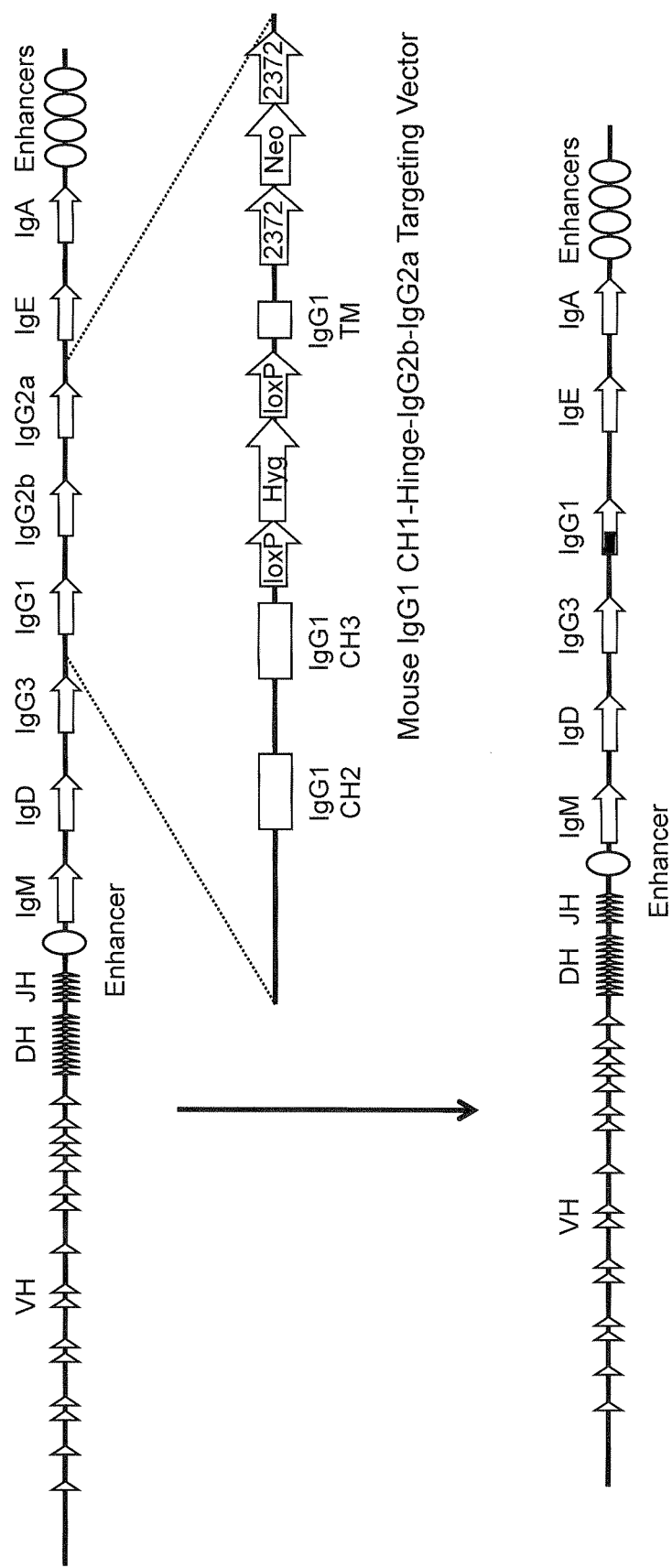
FIG. 5 illustrates a mouse heavy chain constant region targeted with a construct that deletes a CH1 domain and deletes a hinge region and that deletes an IgG2b gene and an IgG2a gene.
Figure 6:
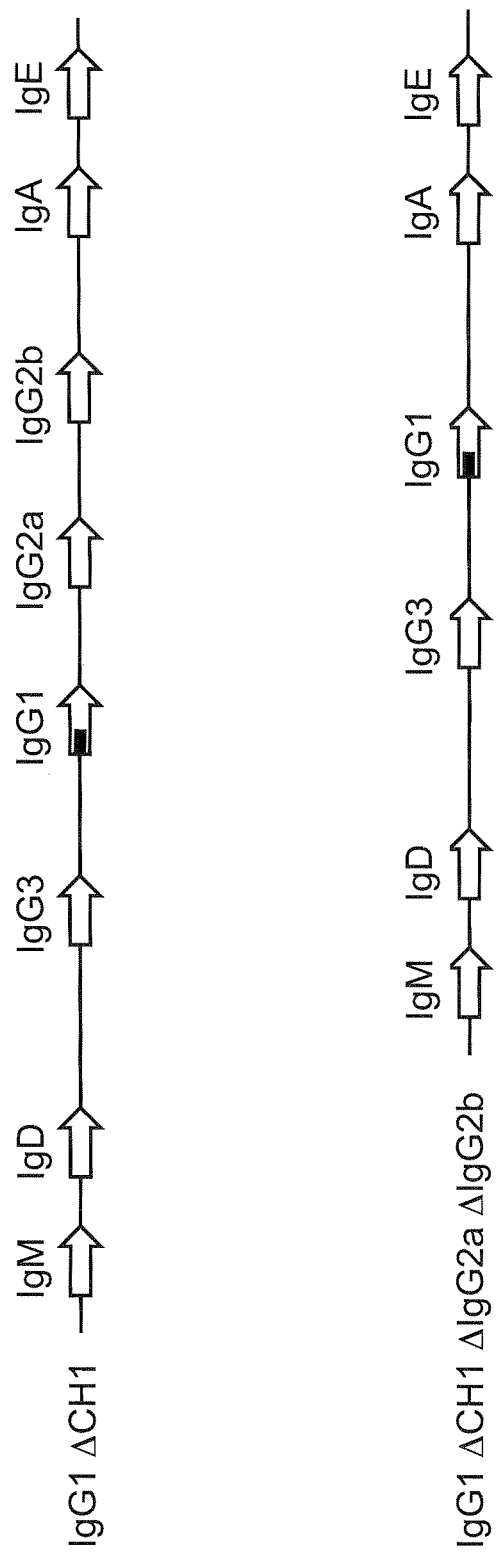
FIG. 6 illustrates a heavy chain constant region of a genetically modified mouse having an IgG1 that lacks a CH1 domain or lacks a CH1 domain and a hinge region (top), and a heavy chain constant region of a genetically modified mouse having an IgG1 that lacks a CH1 domain or lacks a CH1 domain and a hinge region, and that lacks an IgG2a gene and lacks an IgG2b gene (bottom).

A genetically modified mouse lacking an IgG1 CH1 sequence (IgG1ΔCH1), or lacking an IgG1 CH1 sequence and lacking a hinge (IgG1ΔCH1-Δhinge), can be further modified to favor usage of the modified IgG1 isotype by deleting one or more other IgG isotypes, e.g., by deleting or functionally disabling sequences encoding IgG2b and IgG2a. For example, a targeting construct is made having a 5' homology arm containing sequence upstream of the endogenous hinge region sequence (or upstream of the endogenous CH1 domain sequence), sequences that encode the IgG1 CH2 and CH3 domains, a drug selection cassette followed by a sequence encoding the IgG1 transmembrane domain, followed by another drug selection cassette if desired. Upon homologous recombination at the locus and removal of the drug selection cassette(s) (e.g., by Cre treatment), the endogenous heavy chain constant locus contains only two IgG genes: an endogenous IgG3 and the IgG1ΔCH1 (see FIG. 4, bottom; recombinase site(s) not shown; see FIG. 6, bottom) or IgG1ΔCH1-Δhinge (see FIG. 5, bottom; recombinase site(s) not shown; see FIG. 6, bottom).

Figure 10:
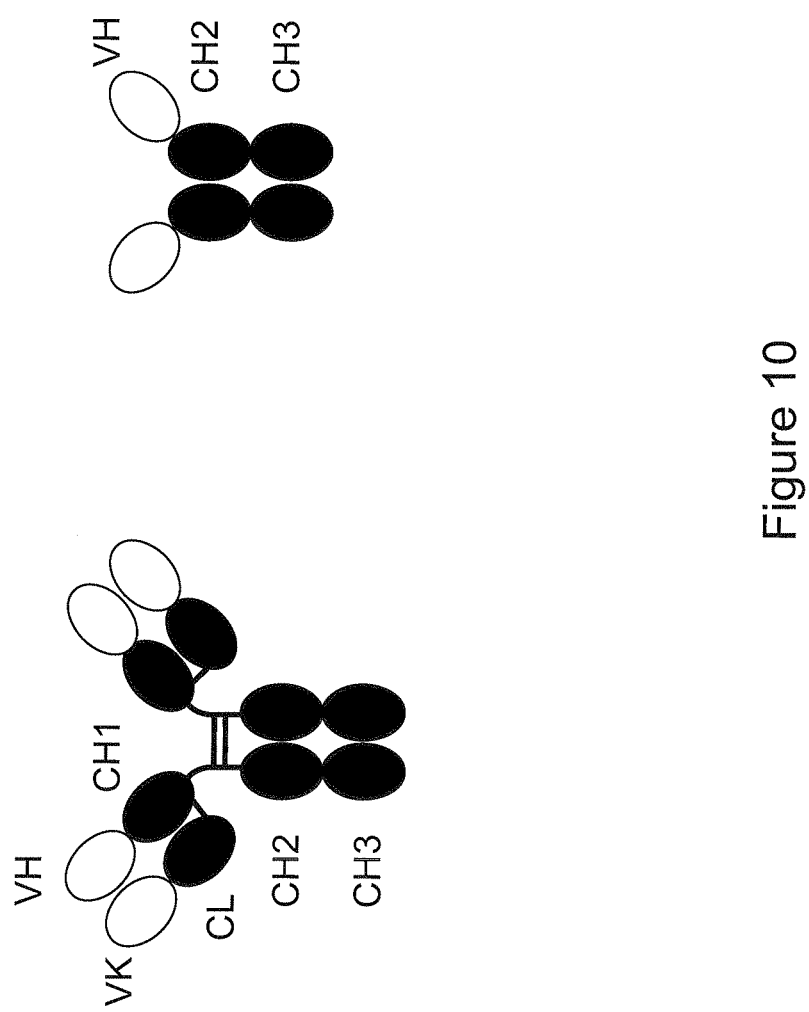
FIG. 10 provides a schematic diagram of a normal IgG1 antibody (left) and a heavy chain antibody that lacks a CH1 domain and lacks a hinge region.

An IgG1 expressed in a genetically modified mouse having an IgG1ΔCH1-Δhinge or an IgG1ΔCH1ΔIgG2aΔIgG2b allele will have a structure as shown on the right panel of FIG. 10, i.e., the VH domain will be fused to the CH2 domain. The left panel of FIG. 10 provides, for comparison, a wild-type IgG1 antibody, showing its CH1 domain linked via a hinge region to the CH2 domain, and linked by disulfide linkage to the light chain constant domain CL. In contrast, the antibody made by the genetically modified mouse lacks the hinge and CH1 domains and thus lacks any CL domain.

Genetically modified mice as described above, and others, are made by introducing a suitable targeting construct into a suitable mouse ES cell (in one or more independent targetings), and positive clones comprising a marker or selection cassette of the targeting construct are identified and grown. Clones are then employed as donor ES cells in a host embryo under conditions suitable for making a chimeric mouse or a fully ES cell-derived mouse. The marker or selection cassette can be optionally removed, either at the ES cell stage or in the chimeric or ES cell-derived mouse, e.g., by employing a loxed cassette and breeding to a Cre-containing strain, or by electroporating the ES cell with a Cre expression vector.

A genetically modified mouse having an IgG1ΔCH1-Δhinge allele (heterozygous) was made in accordance with an embodiment of the invention. Serum was isolated from the mouse and blotted in a Western (reducing conditions) using an anti-mouse IgG1 antibody to detect heavy chain. In contrast to a wild-type mouse, which displayed a band corresponding in size to a wild-type IgG1 heavy chain, the mouse genetically modified to contain the IgG1ΔCH1-Δhinge allele also expressed a heavy chain that reacted with anti-mouse IgG1 antibody that had the expected size of a heavy chain antibody consisting of the VH, CH2, and CH3 domains (see FIG. 8).

EXAMPLES

Example 1

In Vitro Expression of Heavy Chain Antibodies

Chimeric heavy chain constructs were made using molecular biology techniques (e.g., see Maniatis et al. 1982. Molecular Cloning: A Laboratory Manual. Cold Spring Harbor Laboratory) to fuse human variable regions with a murine IgG2b (mIgG2b) constant region. The human variable gene segment for each construct was a full-length human variable gene segment containing both exons (i.e., leader sequence plus mature sequence), identified from an hVR of an IgM isolated from a naive RAG mouse that contained a replacement of the endogenous mouse immunoglobulin heavy chain locus with three hVR gene segments, all hDH gene segments, and all hJH gene segments. The light chain of the IgM antibody was a mouse light chain.

Two versions of the mIgG2b sequence were used; one with and one without a CH1 domain. Several other constructs were also made to serve as transfection and expression controls. A first control construct was made using a cytokine receptor fused to the CH2 and CH3 domains of mouse IgG2a (mIgG2a) constant region (Control I). Two other controls were constructed by fusing a murine ROR signal sequence to a murine IgG2a sequence with and without CH1 domains (Control II and III, respectively).

Camelized versions of each human variable region were also made using PCR site-directed mutagenesis techniques (e.g., see Hutchinson et al. 1978. Mutagenesis at a specific position in a DNA sequence. J. Biol. Chem. 253(18):6551-60). Two specific primer sets were used for each variable region to create specific mutations within the human variable region sequence resulting in a human variable region sequence containing camel-like features. Primers L1 (SEQ ID NO:1) and HH1.2 mut BOT (SEQ ID NO:2) were used to amplify one product comprising the 5' half of the variable region while primers HH1.2 mut TOP (SEQ ID NO:3) and m18.3.1 (SEQ ID NO:4) were used to amplify the 3' half of the variable region. These products were purified and mixed together to serve as a template for a third PCR reaction using primers L1 and m18.3.1. The resulting camelized human variable region PCR product was cloned, purified and confirmed by sequencing.

The full length heavy chain constructs (variable and constant) were made by amplifying the human variable regions (camelized and non-camelized) and constant regions with primers containing restriction enzyme sites to allow for subsequent ligation together via cohesive ends. All full length heavy chain constructs were cloned into expression vectors, purified and confirmed again by sequencing. Table 1 sets forth each heavy chain construct, their SEQ ID NOs and a short description for each construct.

TABLE 1

| Construct | Description | SEQ ID NO (DNA/Protein) |
|---|---|---|
| hVR-mFc | Non-camelized human variable region fused to mouse IgG2b | 5/6 |
| hVR*-mFc | Camelized human variable region fused to mouse IgG2b | 7/8 |
| hVR-mFcΔCH1 | Non-camelized human variable region fused to mouse IgG2b lacking a CH1 domain | 9/10 |
| hVR*-mFcΔCH1 | Camelized human variable region fused to mouse IgG2b lacking a CH1 domain | 11/12 |

Figure 7:
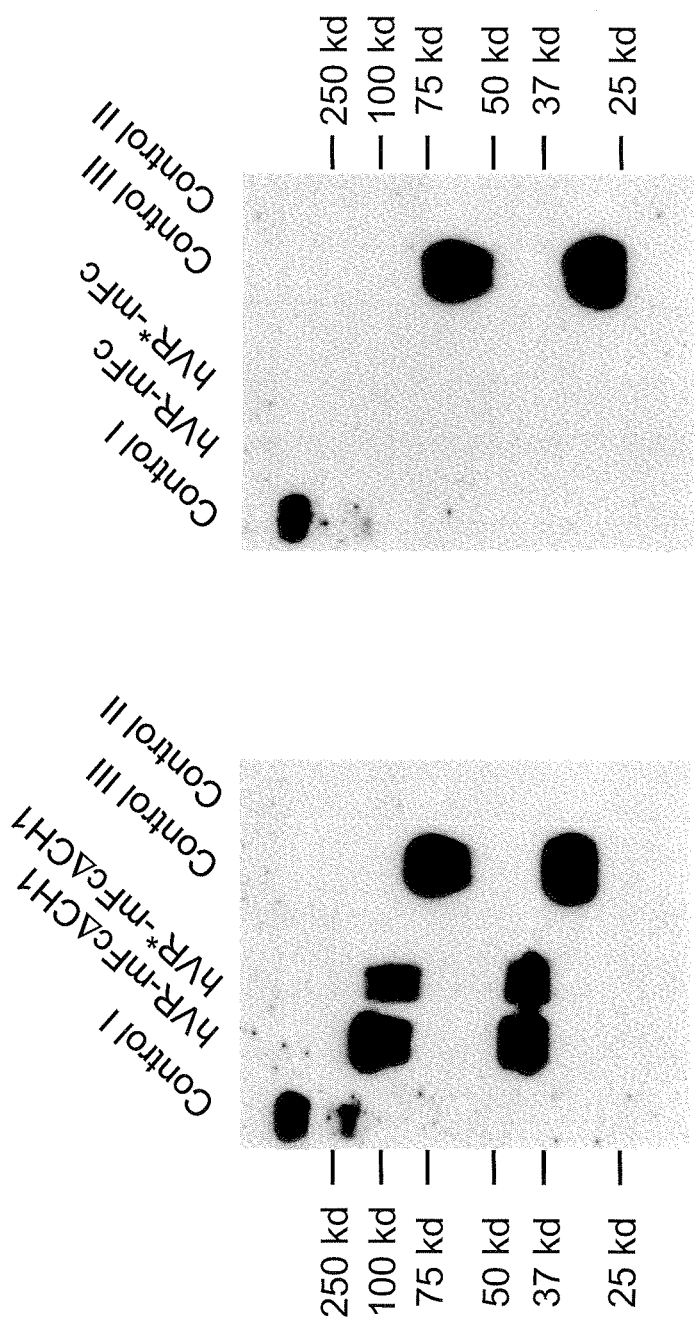
FIG. 7 shows Western blots of CHO cell supernatants from CHO cells engineered to independently express control (cytokine ectodomain fusion with a mouse Fc), chimeric (human VR)/(mouse Fc) heavy chain antibody lacking a CH1 domain (hVR-mFcΔCH1), camelized chimeric (human VR)/(mouse Fc) heavy chain antibody lacking a CH1 domain (hVR*-mFcΔCH1), chimeric (human VR)/(mouse Fc) heavy chain antibody (hVR-mFc), camelized chimeric (human VR)/(mouse Fc) heavy chain antibody (hVR*-mFc), mFc with (mFc) or without (mFcΔCH1) a CH1 domain.

Chimeric heavy chain constructs were transiently transfected into Chinese Hamster Ovary cells (CHO-K1) to analyze expression in the absence of immunoglobulin light chain. Supernatants and cell lysates were examined by Western blot to detect presence of heavy chain using horseradish peroxidase (HRP) conjugated anti-mouse IgG antibody (Promega) by chemilumescence. All the chimeric heavy chain constructs were transiently transfected six (6) independent times. A representative Western blot of the transfections is shown in FIG. 7.

All chimeric heavy chain constructs, with and without the CH1 domain, as well as the control constructs, were detected in the cell lysate. Only constructs lacking a CH1 domain were observed in the supernatants (FIG. 7, left). Control I and Control III (mouse Fc protein lacking a CH1 domain) were also detected (FIG. 7), but mouse Fc protein containing a CH1 domain was not detected. Both non-camelized and camelized heavy chain constructs containing a CH1 domain were not detected in the supernatant for any transfection (FIG. 7, right). However, both non-camelized and camelized human heavy chain constructs lacking a CH1 domain were detected in the supernatant for all transfections. Together, the results establish that hVRs (normal or camelized) that lack a CH1 domain can be expressed and secreted from transiently transfected CHO cells in the absence of immunoglobulin light chain, whereas hVRs (normal or camelized) that contain a CH1 domain could not be secreted in the absence of light chain.

Example 2

Modification of the Mouse Heavy Chain IgG1 Constant Region

A. Preparation of a mouse IgG1-CH1-Hinge Targeting Vector (FIG. 3)

A targeting construct for introducing a deletion of the CH1 and hinge regions of the mouse IgG1 constant domain for the C57BL/6 allele from an ES cell of a VELOCIMMUNE® mouse (described below) was constructed.

The targeting construct was made using VELOCIGENE® technology (see, e.g., U.S. Pat. No. 6,586,251 and Valenzuela et al. (2003) High-throughput engineering of the mouse genome coupled with high-resolution expression analysis, Nature Biotech. 21(6):652-659) to modify the Bacterial Artificial Chromosome (BAC) BMQ 70p08. BMQ 70p08 BAC DNA was modified to delete the CH1 and hinge regions of the IgG1 constant domain while leaving the remainder of the IgG1 gene intact (e.g., CH2, CH3 and transmembrane exons).

Briefly, upstream and downstream homology arms were made employing primers m102 (SEQ ID NO:13) and m104 (SEQ ID NO:14) and m100 (SEQ ID NO:15) and m99 (SEQ ID NO:16), respectively. These homology arms were used to make a cassette that deleted the CH1 and hinge regions of the IgG1 constant domain while retaining the CH2, CH3 and transmembrane regions of the IgG1 constant domain (see, e.g., FIG. 3). The targeting construct included a loxed hygromycin resistance gene positioned between the CH3 and transmembrane domain exons of the IgG1 gene. Genes upstream of the CH1 and hinge exons (e.g., IgG3, IgD, IgM) and downstream of the IgG1 transmembrane exon (e.g., IgG2b, IgG21, IgE, IgA, etc.) were unmodified by the targeting construct. Switch regions for all constant domains were unmodified by the targeting construct. The nucleotide sequence across the deletion included the following, which indicates a splice acceptor sequence that is present at the deletion point: TGACAGTGTA ATCACATATA CTTTTTCTTG T(AG)TC-CCAGA AGTATCATC (SEQ ID NO:17). The deletion sequence comprises a splice acceptor (the AG contained within parentheses above) with pre-CH1 sequences 5' of the splice acceptor and CH2 exon sequences 3' of the splice acceptor.

B. Preparation of a Mouse IgG1-CH1 Targeting Vector (FIG. 2)

A second targeting construct for introducing a deletion of the CH1 of the mouse IgG1 constant domain for the 129/SvEvTac allele from an ES cell of a VELOCIMMUNE® mouse (described below) was constructed in a similar fashion as described in section A of this Example.

The targeting construct was made using VELOCIGENE® technology (see, e.g., U.S. Pat. No. 6,586,251 and Valenzuela et al. (2003) High-throughput engineering of the mouse genome coupled with high-resolution expression analysis, Nature Biotech. 21(6):652-659) to modify the Bacterial Artificial Chromosome (BAC) BMQ 70p08. BMQ 70p08 BAC DNA was modified to delete the CH1 region of the IgG1 constant domain while leaving the remainder of the IgG1 gene intact (e.g., hinge, CH2, CH3 and transmembrane exons; see FIG. 2).

The homology arms for the second targeting construct were the same as those for the CH1-Hinge targeting vector (as described above in section A of this Example). These homology arms were used to make a cassette that deleted the CH1 region of the IgG1 constant domain while retaining the hinge, CH2, CH3 and transmembrane regions of the IgG1 constant domain (see, e.g., FIG. 2). The targeting construct included a loxed hygromycin resistance gene positioned between the CH3 and transmembrane domain exons of the IgG1 gene. Genes upstream of the CH1 exon (e.g., IgG3, IgD, IgM) and downstream of the IgG1 transmembrane exon (e.g., IgG2b, IgG21, IgE, IgA, etc.) were unmodified by the targeting construct. Switch regions for all constant domains were unmodified by the targeting construct. The nucleotide sequence across the deletion included the following, which indicates a splice acceptor sequence that is present at the deletion point: TGACAGTGTA ATCACATATA CTTTTTCTTG T(AG)TGCCCAG GGATTGTGGT TGTAAGCCTT GCATATG- TAC AGGTAAGTCA GTAGGCCTTT CACCCTGACC C (SEQ ID NO:64). The deletion sequence comprises a splice acceptor (the AG contained within parentheses above) with pre-CH1 sequences 5' of the splice acceptor and hinge exon sequences 3' of the splice acceptor.

Example 3

Modification of the Mouse Heavy Chain Constant Region in ES Cells

A. Targeting Mouse ES Cells with an IgG1-CH1-Hinge Targeting Vector

A mouse ES cell was targeted with the targeting construct described above (i.e., a targeting construct introducing a deletion of the CH1 and hinge regions of the IgG1 gene). The ES cell was from a VELOCIMMUNE® mouse that was a 50/50 mix of a 129 strain and a C57BL/6 strain, bearing genetic modifications that comprise replacement of mouse heavy and light chain variable region gene segments with unrearranged human heavy and light chain variable region gene segments. The 129 strain employed to cross with C57BL/6 is a strain that comprises a replacement of mouse heavy chain and light chain variable region gene segments with human heavy chain and light chain variable region gene segments.

The heterozygous VELOCIMMUNE® mice bear a single set of endogenous mouse heavy chain constant region genes from the 129 strain at one allele and a single set of endogenous mouse heavy chain constant region genes from the C57BL/6 strain at the other allele. The 129 heavy chain allele is contiguous with a locus of heavy chain variable region gene segments that are human heavy chain variable region gene segments that have replaced the endogenous mouse heavy chain variable region gene segments (i.e., at the endogenous mouse locus). The BL/6 heavy chain allele is contiguous with wild-type mouse heavy chain variable region gene segments. The VELOCIMMUNE® mice also bear wild-type endogenous mouse light chain constant region genes. Thus, by targeting the 129 allele with a construct comprising an IgG, D, E, or A CH1 deletion a chimeric human/mouse heavy chain antibody could be produced, whereas by targeting the C57BL/6 allele with a similar construction, a fully mouse heavy chain antibody lacking a CH1 domain and lacking a hinge could be produced.

ES cells from the VELOCIMMUNE® mice described above were electroporated with linearized targeting vector of section A in Example 2 and selected for the presence of the hygromycin resistance gene.

B. Targeting Mouse ES Cells with an IgG1-CH1 Targeting Vector

In a similar fashion, a mouse ES cell was targeted with the CH1 targeting construct described in section B of Example 2 (see also FIG. 2). The ES cell was from a VELOCIMMUNE® mouse that was a 50/50 mix of a 129/SvEvTac strain and a C57BL/6 strain, bearing genetic modifications that comprise replacement of mouse heavy and light chain variable region gene segments with unrearranged human heavy and light chain variable region gene segments. The 129/SvEvTac strain employed to cross with C57BL/6 is a strain that comprises a replacement of mouse heavy chain and light chain variable region gene segments with human heavy chain and light chain variable region gene segments.

The heterozygous VELOCIMMUNE® mice bear a single set of endogenous mouse heavy chain constant region genes from the 129/SvEvTac strain at one allele and a single set of endogenous mouse heavy chain constant region genes from the C57BL/6 strain at the other allele. The 129/SvEvTac heavy chain allele is contiguous with a locus of heavy chain variable region gene segments that are human heavy chain variable region gene segments that have replaced the endogenous mouse heavy chain variable region gene segments (i.e., at the endogenous mouse locus). The BL/6 heavy chain allele is contiguous with wild-type mouse heavy chain variable region gene segments. The VELOCIMMUNE® mice also bear wild-type endogenous mouse light chain constant region genes. Thus, by targeting the 129/SvEvTac allele with a construct comprising an IgG, D, E, or A CH1 deletion a chimeric human/mouse heavy chain antibody could be produced, whereas by targeting the C57BL/6 allele with a similar construction, a fully mouse heavy chain antibody lacking a CH1 domain and lacking a hinge could be produced.

ES cells from the VELOCIMMUNE® mice described above were electroporated with linearized targeting vector, described in section B in Example 2, and selected for the presence of the hygromycin resistance gene.

Example 4

Generation of Mice Carrying a Modified IgG1 Constant Region

A. Mice Carrying an IgG1-CH1-Hinge Deletion

Targeted ES cells described above were used as donor ES cells and introduced into an 8-cell stage mouse embryo by the VELOCIMOUSE® method (see, e.g., U.S. Pat. No. 7,294, 754 and Poueymirou et al. (2007) F0 generation mice that are essentially fully derived from the donor gene-targeted ES cells allowing immediate phenotypic analyses Nature Biotech. 25(1):91-99. VELOCIMICE® (F0 mice fully derived from the donor ES cell) bearing targeted C57BL/6 IgG1 alleles were identified by genotyping using a modification of allele assay (Valenzuela et al., supra) that detected the presence of sequences positioned upstream and downstream of the deleted hinge and CH1 regions.

Mice genotyped for the IgG1 CH1 and hinge deletion (in the C57BL/6 allele, i.e., the mouse allele) were bred to a Cre deleter mouse strain (see, e.g., International Patent Application Publication No. WO 2009/114400) in order to remove the loxed hyg cassette downstream of the IgG1 CH3 exon and upstream of the IgG1 transmembrane exon, introduced by the targeting construct (see, e.g., FIG. 3). Pups were genotyped and a pup heterozygous for the IgG1 CH1 and hinge deletion was selected to examine IgG1 heavy chain expressed from the C57BL/6 allele in the pup's serum.

B. Mice Carrying an IgG1-CH1 Deletion

In a similar fashion, targeted ES cells carrying a deletion of the IgG1 CH1 region were used as donor ES cells and introduced into an 8-cell stage mouse embryo by the VELOCIMOUSE® method (see, e.g., U.S. Pat. No. 7,294,754 and Poueymirou et al. (2007) F0 generation mice that are essentially fully derived from the donor gene-targeted ES cells allowing immediate phenotypic analyses Nature Biotech. 25(1):91-99. VELOCIMICE® (F0 mice fully derived from the donor ES cell) bearing targeted 129SvEv/Tac alleles were identified by genotyping using a modification of allele assay (Valenzuela et al., supra) that detected the presence of sequences positioned upstream and downstream of the deleted CH1 region.

Mice genotyped for the IgG1 CH1 deletion (in the 129/SvEvTac allele, i.e., the human allele) were bred to a Cre deleter mouse strain (see, e.g., International Patent Application Publication No. WO 2009/114400) in order to remove the loxed hyg cassette downstream of the IgG1 CH3 exon and upstream of the IgG1 transmembrane exon, introduced by the targeting construct (see, e.g., FIG. 2). Pups were genotyped and a pup homozygous for the IgG1 CH1 deletion was selected to examine modified IgG1 heavy chain expression.

Example 5

Heavy Chain Antibodies from Mice Carrying a Modified IgG1 Gene

A. IgG1-ΔCH1-ΔHinge Mice

A mouse pup identified above as containing the CH1 and hinge deletion, and a wild-type pup, were bled and sera from the bled mice were prepared for Western blotting to identify any expressed IgG in the sera using an anti-mIgG1 antibody. Briefly, 10 μL of a 1:100 dilution of mouse sera was used in reducing SDS-PAGE, and the gel was transferred to a PVDF membrane. The blot was blocked overnight with 5% nonfat milk in Tris-Buffered Saline with 0.05% Tween-20 (TBST; Sigma), washed 4 times for 5 minutes per wash with TBST, and then exposed to primary antibody (goat anti-mIgG1 conjugated to HRP, Southern Biotech) diluted 1:1,000 in 1% nonfat milk in TBST for two hours at room temperature. The blot was washed 6 times for 5 minutes per wash. The blot was developed for 5 minutes with SUPERSIGNAL™ West Pico Chemiluminescent Substrate (Thermo Scientific) and then exposed to film for 1 minute.

Figure 8:
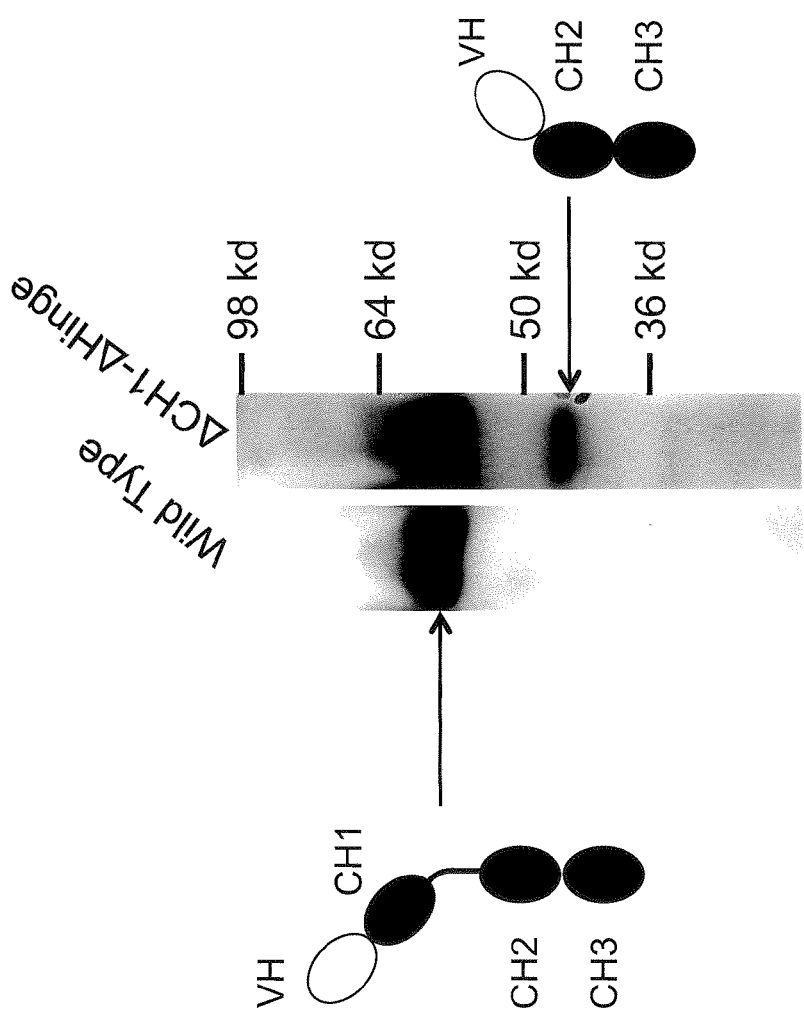
FIG. 8 shows Western blot images from a reducing SDS-PAGE of mouse sera from a wild-type mouse (left) and from a genetically modified mouse whose IgG1 lacks a CH1 domain and lacks a hinge region (heterozygous) (right), blotted with anti-mouse IgG; schematics of the heavy chains are provided, as are molecular weight marker positions.

Serum from the VELOCIMOUSE® (50% wild-type BL/6; 50% ΔCH1-Δhinge BL/6) derived from the targeted donor ES cell revealed a mixture of bands: one band of about 57.5 kD, the expected size for a wild-type IgG, and one band at about 45 kD, the expected size for an IgG lacking a CH1 domain and a hinge (FIG. 8). The results are consistent with the VELOCIMOUSE® expressing a normal mouse heavy chain from the wild-type BL/6 allele and a ΔCH1/Δhinge mouse heavy chain from its ΔCH1-Δhinge BL/6 allele. This result establishes that genetically modified mice bearing a functional IgM gene and an IgG gene that lacks a CH1 domain and a hinge domain are capable of expressing heavy chain antibodies in serum.

B. IgG1-ΔCH1 Mice

In a similar fashion, mouse pups homozygous for the CH1 deletion, and wild-type pups, were bled. Plasma and serum (for five homozygotes; two wild-type) from the bled mice were prepared for Western blotting to identify any expressed IgG in the sera using an anti-mIgG1 antibody (described above). Western blots of serum and plasma from mice homozygous for the IgG1-ΔCH1 deletion revealed a mixture of bands: one band of about 45 kD, the expected size for a single chain IgG1 lacking a CH1 domain, and one band at about 75 kD, the expected size for a dimer IgG lacking a CH1 domain (data not shown). The results are consistent with the homozygous VELOCIMICE® expressing an IgG1-ΔCH1 heavy chain from either one or both heavy chain loci. This result establishes that genetically modified mice bearing a functional IgM gene and an IgG gene that lacks a CH1 domain are capable of expressing heavy chain antibodies in the peripheral lymphocyte compartment of the animals' immune system.

Example 6

Characterization of Mice Homozygous for IgG1-CH1-Hinge Deletion

Figure 9:
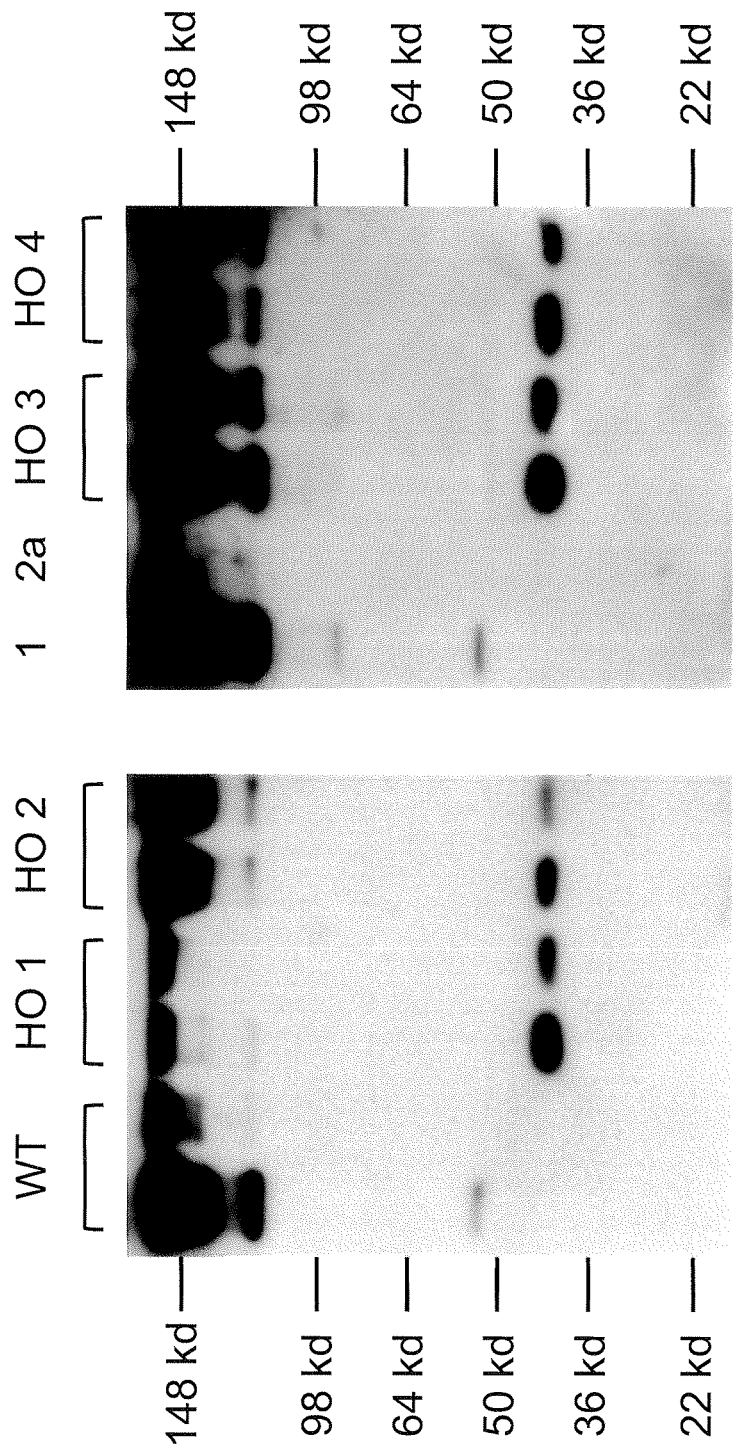
FIG. 9 shows Western blots images from a non-reducing SDS-PAGE of mouse sera from a wild-type mouse (WT) and four genetically modified mice whose IgG1 lacks a CH1 domain and lacks a hinge region (homozygous; noted as HO 1, HO 2, HO 3, HO 4, respectively), blotted with anti-mouse IgG; each mouse (WT or HO) is represented by two lanes indicated by brackets above the lanes corresponding to 1:5 and 1:10 dilutions of serum for each animal (consecutive lanes from left to right for each).

VELOCIMICE® heterozygous for the CH1-hinge deletion were bred together to obtain mice homozygous for the deletion. Four mouse pups were identified as homozygous for IgG1 ΔCH1-Δhinge. These four mice and a wild-type mouse were bled and sera from the bled mice were prepared for Western blotting to identify any expressed IgG in the sera using an anti-mIgG1 antibody (as described above). FIG. 9 shows the film developed from the PVDF-membrane used in this experiment. Serum was diluted 1:5 and 1:10 and 10 μL of each dilution was loaded onto the gel side-by-side for each mouse. On the top portion of the gel images, the lanes are labeled for each mouse as well as IgG1 (1) and IgG2a (2a) controls.

Serum from the wild-type mouse showed an expected pattern for a wild-type mouse that expresses normal antibodies comprising two heavy chains and two light chains (approximately 150 kD). All four mice (homozygous for IgG1 ΔCH1-Δhinge) each showed a mixture of bands: one band of about 150 kD, the expected size for a wild-type IgG other than IgG1 (e.g., IgG2a, IgG2b or IgG3), and one band at about 45 kD, the expected size for an IgG lacking a CH1 domain and a hinge (FIG. 9). These results are consistent with the mice expressing an IgG1 heavy chain antibody lacking a CH1 domain and a hinge region and lacking a light chain. This result further establishes that genetically modified mice bearing a functional IgM gene and an IgG gene that lacks a CH1 domain and a hinge region are capable of expressing heavy chain antibodies in serum.

Figure 11:
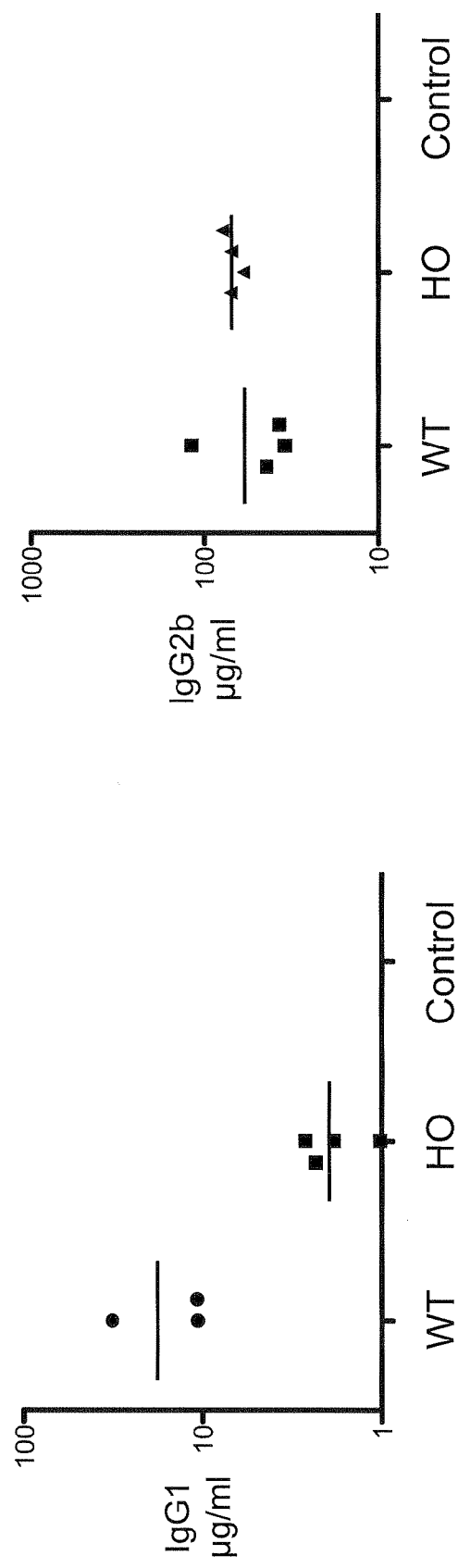
FIG. 11 shows separate IgG1 and IgG2b serum immunoglobulin assays from wild type mice (WT) and genetically modified mice that contain an IgG1 lacking a CH1 domain and lacking a hinge region (HO; homozygous mouse that expresses a heavy chain antibody that lacks a CH1 domain and lacks a hinge region). Control is pooled human serum.

In another experiment, serum expression of IgG was determined from mice homozygous for the IgG1 ΔCH1-Δhinge using an ELISA assay. Briefly, antibodies specific for either mIgG1 or mIgG2b (Pharmingen) were separately diluted and 100 μl/well was coated onto plates at 2 μg/mL in 1×PBS (Irvine Scientific) and incubated at 4° C. overnight. The following day the plates were washed four times with PBS with 0.05% Tween-20 (PBST; Sigma). After the fourth wash, plates were blocked with 250 µL/well of PBST with 5% BSA (Sigma) and incubated at room temperature for one hour. Serum and standards were serially diluted (dilution factor of 0.316) in PBST in 0.5% BSA down the plate (from top to bottom) at a starting concentration of 400 ng/mL (mIgG1) or 600 ng/mL (mIgG2b). After blocking, the plates were washed again four times with PBST. Following the fourth wash, 100 µL of serum or standard was added to the plates and incubated for one hour at room temperature. The plates were again washed four times with PBST. Following the washes, 100 µL of a biotinylated detection antibody (10 ng/mL of rat anti-mIgG1 or 250 ng/mL of anti-mIgG2b; Pharmingen) was added to the plates and incubated for one hour at room temperature. The plates were again washed as described above. Following the wash, 100 µL/well of a 1:20,000 dilution of horseradish peroxidase conjugated to streptavidin (HRP-SA) in PBST was added to the plates and the plates were incubated for 30 minutes at room temperature. The plates were then washed six times with PBST, after which 100 µL/well of a 1:1 dilution of Substrate A and B (BD OPTEIA™; BD Biosciences) was added and the plates were maintained in the dark. The reaction was developed in the dark and stopped as desired (approx. 15 minutes) with 1N phosphoric acid. Stopped reactions were read on a Wallac 1420 Work Station VICTOR™ Plate Reader at an absorption wavelength of 450 nm (1.0 sec/reading) and the results plotted on graphs (FIG. 11).

Serum from wild-type mice showed normal levels of IgG1 and IgG2b. Mice homozygous for IgG1 ΔCH1-Δhinge were capable of expressing an IgG1 lacking a CH1 domain and a hinge region in the periphery (serum; left side of FIG. 11). Further, serum levels of other IgG isotypes (e.g., IgG2b) were not noticeably reduced from wild-type levels (right side of FIG. 11). This result further establishes that genetically modified mice bearing a functional IgM gene and an IgG gene that lacks a CH1 domain and a hinge region are capable of expressing a modified IgG1 isotype (i.e., lacking a CH1 domain and a hinge) that can be detected in serum.

Example 7

Analysis of V-D-J Rearrangements in IgG1 Modified Mice

A. Mice Homozygous for an IgG1-CH1-Hinge Deletion

Mice homozygous for the IgG1 ΔCH1-Δhinge modification were analyzed for V-D-J recombination and heavy chain gene usage by reverse-transcriptase polymerase chain reaction (RT-PCR) using RNA isolated from splenocytes.

Briefly, spleens were harvested and perfused with 10 mL RPMI-1640 (Sigma) with 5% HI-FBS in sterile disposable bags. Each bag containing a single spleen was then placed in a STOMACHER™ (Seward) and homogenized at a medium setting for 30 seconds. Homogenized spleens were filtered using a 0.7 µm cell strainer and then pelleted with a centrifuge (1000 rpm for 10 minutes) and red blood cells (RBCs) were lysed in BD PHARM LYSE™ (BD Biosciences) for three minutes. Splenocytes were diluted with RPMI-1640 and centrifuged again followed by resuspension in 1 mL of PBS (Irvine Scientific). RNA was isolated from pelleted splenocytes using standard techniques known in the art.

RT-PCR was performed on splenocyte RNA using a set of degenerate primers specific for mouse heavy chain variable region (VH) gene segments (Novagen) and a mouse IgG1 CH2 primer (CGATGGGGGC AGGGAAAGCT GCAC; SEQ ID NO:40). PCR products were gel-purified and cloned into pCR2.1-TOPO TA (Invitrogen) and sequenced with M13 Forward (GTAAAACGAC GGCCAG; SEQ ID NO:41) and M13 Reverse (CAGGAAACAG CTATGAC; SEQ ID NO:42) primers located within the vector sequence at positions flanking the cloning site. Nineteen clones were sequenced to determine heavy chain gene usage and sequence of the junction of the rearranged VH and the CH2 of the IgG1 constant region (Table 2).

TABLE 2

| Clone | Heavy Chain Gene Usage | | |
|---|---|---|---|
| | $V_H$ | $D_H$ | $J_H$ |
| B1 | 1-58 | 3-2 | 2 |
| B2 | 1-26 | 4-1 | 1 |
| B3 | 1-50 | 2-14 | 2 |
| B4 | 1-58 | 3-2 | 2 |
| B5 | 14-2 | 4-1 | 4 |
| D2 | 3-6 | 1-1 | 4 |
| D5 | 14-1 | 3-3 | 2 |
| D6 | 14-2 | 4-1 | 3 |
| D7 | 3-6 | 1-1 | 4 |
| E2 | 7-1 | 3-1 | 4 |
| E3 | 1-50 | 2-14 | 2 |
| E4 | 1-50 | 2-14 | 2 |
| E7 | 1-50 | 2-14 | 2 |
| E8 | 1-72 | 1-1 | 4 |
| E10 | 1-42 | 1-1 | 1 |
| F6 | 5-6 | 1-1 | 1 |
| F7 | 5-6 | 1-1 | 1 |
| F8 | 5-6 | 1-1 | 1 |
| F10 | 5-6 | 1-1 | 1 |

FIG. 12 shows the sequence alignment of the VH domains rearranged to the CH2 of the IgG1 constant region for eleven of the nineteen RT-PCR clones. The sequences shown in FIG. 12 illustrate unique rearrangements involving different mouse heavy chain V, D and J gene segments and mouse IgG1 devoid of CH1 and hinge regions. Mice homozygous for a deletion of the CH1 and hinge regions of the endogenous IgG1 constant region gene were able to produce heavy chains containing mouse VH domains operably linked to a CH2-CH3 region from a mouse IgG1 constant region devoid of CH1 and hinge regions and produce B cells that expressed mouse IgG1 heavy chains devoid of CH1 and hinge regions and lacking a light chain (FIGS. 8 and 9). These rearrangements demonstrate that the modified loci were able to independently rearrange mouse heavy chain gene segments in multiple, independent B cells in these mice to produce heavy chain antibodies that are similar to those normally found in camels. Further, this Example demonstrates that the deletion of the endogenous IgG1 CH1 and hinge regions did not render the locus inoperable or prevent recombination involving the modified IgG1 constant region. These mice made functional heavy chain antibodies containing an IgG1 devoid of CH1 and hinge regions as part of the endogenous repertoire without any detectable defect in B cell development.

B. Mice Homozygous for an IgG1-CH1 Deletion

In a similar fashion, mice homozygous for the IgG1 ΔCH1 modification were analyzed for V-D-J recombination and human heavy chain gene usage by reverse-transcriptase polymerase chain reaction (RT-PCR) using RNA isolated from splenocytes.

Briefly, spleens were isolated from two homozygous IgG1-ΔCH1 mice as described above in section A of this Example. CD19⁺ B cells were isolated using magnetic cell sorting (MACS, Miltenyi Biotec) from pooled splenocytes. RNA was extracted from the sorted CD19⁺ B cells using Qiagen ALL-PREP™ DNA/RNA mini kit (Qiagen). First-strand cDNA was synthesized with SUPERSCRIPT™ III Reverse Transcriptase and Oligo (dT) 20 primers (Invitrogen). The cDNA was then used as a template for PCR performed with a 3' mouse IgG1 hinge specific primer and 5' degenerate primers designed to bind human heavy variable leader sequences (Table 3). PCR products were cloned into pCR2.1 TOPO™ TA vector (Invitrogen) and sequenced with M13 Forward and M13 Reverse primers (as described above in section A of this Example).

TABLE 3

| Primer | Sequence (5'-3') | SEQ ID NO: |
|---|---|---|
| hVHL-1 | TCACCATGGA CTGSACCTGG A | 43 |
| hVHL-2 | CCATGGACAC ACTTTGYTCC AC | 44 |
| hVHL-3 | TCACCATGGA GTTTGGGCTG AGC | 45 |
| hVHL-4 | AGAACATGAA ACAYCTGTGG TTCTT | 46 |
| hVHL-5 | ATGGGGTCAA CCGCCATCCT | 47 |
| hVHL-6 | ACAATGTCTG TCTCCTTCCT CAT | 48 |
| 3' mIgG1 Hinge | GCAAGGCTTA CAACCACAAT C | 49 |

To determine heavy chain gene usage in mice homozygous for IgG1 ΔCH1, twenty-eight RT-PCR clones were sequenced. Within these clones, seven unique rearrangements of human V, D and J gene segments were observed (Table 4).

TABLE 4

| | Heavy Chain Gene Usage | | |
|---|---|---|---|
| Clone | $V_H$ | $D_H$ | $J_H$ |
| A2 | 1-69 | 6-19 | 6 |
| A5 | 1-69 | 6-7 | 4 |
| A8 | 1-8 | 4-4 | 4 |

TABLE 4-continued

| | Heavy Chain Gene Usage | | |
|---|---|---|---|
| Clone | $V_H$ | $D_H$ | $J_H$ |
| C2 | 1-18 | 6-6 | 2 |
| C4 | 1-18 | 3-16 | 6 |
| D9 | 1-18 | 6-6 | 4 |
| H8 | 1-18 | 1-7 | 4 |

FIG. 13 shows the sequence alignment of the VH domains rearranged to the hinge-CH2-CH3 of the IgG1 constant region for the seven rearrangements shown in Table 4. The sequences shown in FIG. 13 illustrate unique rearrangements involving different human heavy chain V, D and J gene segments and mouse IgG1 devoid of the CH1 region. Mice homozygous for a deletion of the CH1 region of the endogenous IgG1 constant region gene were able to produce heavy chains containing human VH domains operably linked to a hinge-CH2-CH3 region from a mouse IgG1 constant region devoid of CH1 and produce B cells that expressed mouse IgG1 heavy chains devoid of CH1 regions and lacking a light chain (data not shown). These rearrangements demonstrate that either one or both modified loci (IgG1 ΔCH1-Δhinge and IgG1 ΔCH1) were able to independently rearrange heavy chain gene segments (mouse and human) in multiple, independent B cells in these mice to produce heavy chain antibodies that are similar to those normally found in camels. Further, this Example demonstrates that the deletion of the endogenous IgG1 CH1 did not render the locus inoperable or prevent recombination involving human heavy chain V, D and J gene segments and the modified mouse IgG1 constant region. These mice made functional heavy chain antibodies containing human heavy chain V domains and a mouse IgG1 devoid of CH1 as part of the endogenous repertoire without any detectable defect in B cell development.

We claim:

1. A transgenic mouse comprising a germline modification, which modification comprises:
   (a) a deletion of a nucleic acid sequence encoding a CH1 domain of an endogenous IgG constant region gene; and
   (b) an inclusion of one or more human heavy chain variable region gene segments, wherein the one or more human heavy chain variable region gene segments is operably linked to the endogenous IgG constant region of (a);
   wherein the mouse comprises an intact IgM constant region gene and wherein the mouse expresses an IgG heavy chain antibody comprising a human variable domain, lacking a CH1 domain, in whole or in part, and lacking a cognate light chain and secretes said IgG heavy chain antibody into its serum.

2. The mouse of claim 1, wherein the IgG constant region gene is selected from the group consisting of an IgG1 constant region gene, an IgG2b constant region gene, a IgG2a constant region gene, and combinations thereof.

3. The mouse of claim 2, wherein the IgG constant region gene is an IgG1 constant region gene.

4. The mouse of claim 3, characterized in that the mouse additionally expresses:
   a) wild-type IgG3 protein;
   b) wild-type IgG2a protein; and
   c) wild-type IgG2b protein.

5. The mouse of claim 4, further characterized in that the mouse expresses:
   e) wild-type IgM protein;
   f) wild-type IgD protein;
   g) wild-type IgA protein; and
   h) wild-type IgE protein.

6. The mouse of claim 1, characterized in that the IgG heavy chain antibody lacks the CH1 domain in whole.

7. The mouse of claim 1, wherein the IgG heavy chain antibody comprises the human variable domain, an IgG1 hinge, a CH2 domain, and a CH3 domain.

8. The mouse of claim 1, wherein the mouse comprises a functional immunoglobulin light chain gene locus.

9. The mouse of claim 8, wherein the immunoglobulin light chain gene locus is a κ light chain gene locus.

10. The mouse of claim 8, wherein the immunoglobulin light chain gene locus is a λ light chain gene locus.

11. The mouse of claim 1, wherein the mouse is from a strain selected from the group consisting of a 129 strain, a C57BL/6 strain, and a mixed 129×C57BL/6 strain.

12. The mouse of claim 11, wherein the mouse is 50% 129 and 50% C57BL/6.

13. An isolated cell of the mouse of claim 1.

14. The isolated cell of claim 13, wherein the cell is an embryonic stem (ES) cell.

* * * * *

UNITED STATES PATENT AND TRADEMARK OFFICE
CERTIFICATE OF CORRECTION

PATENT NO. : 8,754,287 B2
APPLICATION NO. : 12/965050
DATED : June 17, 2014
INVENTOR(S) : Lynn Macdonald, Sean Stevens and Andrew J. Murphy Page 1 of 1

It is certified that error appears in the above-identified patent and that said Letters Patent is hereby corrected as shown below:

Title Page,
Item (12), "United States Patent MacDonald et al."
should read --United States Patent Macdonald et al.--

Title Page,
Item (75), Inventors: "Lynn MacDonald, White Plains, NY (US); Sean Stevens, San Francisco, CA (US); Andrew J. Murphy, Croton-on-Hudson, NY (US)"
should read --Lynn Macdonald, White Plains, NY (US); Sean Stevens, San Francisco, CA (US); Andrew J. Murphy, Croton-on-Hudson, NY (US)--

Title Page,
Item (74) Attorney, Agent, or Firm: "Chaote Hall & Stewart LLP; Kevin J. Pobursky; Tor E. Smeland" should read --Choate Hall & Stewart LLP; Kevin J. Pobursky; Tor E. Smeland--

In the Claims:
Column 79
Claim 2, line 52, please delete "region gene, an IgG2b constant region gene, a IgG2a constant" and replace with --region gene, an IgG2b constant region gene, an IgG2a constant--

Signed and Sealed this
Sixteenth Day of September, 2014

Michelle K. Lee
*Deputy Director of the United States Patent and Trademark Office*